US 11,413,341 B2

(12) United States Patent
Robinson et al.

(10) Patent No.: US 11,413,341 B2
(45) Date of Patent: *Aug. 16, 2022

(54) VACCINIA VIRAL VECTORS ENCODING CHIMERIC VIRUS LIKE PARTICLES

(71) Applicant: GeoVax, Inc., Smyrna, GA (US)

(72) Inventors: Harriet Robinson, Palo Alto, CA (US); Arban Domi, Atlanta, GA (US); Michael Hellerstein, Marietta, GA (US); Farshad Guirakhoo, Atlanta, GA (US); Nathanael Paul McCurley, Decatur, GA (US)

(73) Assignee: Geovax, Inc., Smyrna, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/796,350

(22) Filed: Feb. 20, 2020

(65) Prior Publication Data
US 2020/0289633 A1    Sep. 17, 2020

Related U.S. Application Data

(63) Continuation of application No. 16/068,527, filed as application No. PCT/US2017/012704 on Jan. 9, 2017, now Pat. No. 11,278,607.

(60) Provisional application No. 62/301,885, filed on Mar. 1, 2016, provisional application No. 62/276,479, filed on Jan. 8, 2016.

(51) Int. Cl.
*C12N 15/86* (2006.01)
*A61K 39/00* (2006.01)

(52) U.S. Cl.
CPC ........ *A61K 39/00117* (2018.08); *C12N 15/86* (2013.01); *A61K 2039/5158* (2013.01); *A61K 2039/53* (2013.01); *A61K 2039/55522* (2013.01); *C12N 2710/24134* (2013.01); *C12N 2710/24143* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,603,112 A | 7/1986 | Paoletti et al. | |
| 4,722,848 A | 2/1988 | Paoletti et al. | |
| 4,769,330 A | 9/1988 | Paoletti et al. | |
| 5,445,953 A | 8/1995 | Dorner et al. | |
| 6,103,244 A | 8/2000 | Dorner et al. | |
| 6,440,422 B1 | 8/2002 | Sutter et al. | |
| 6,696,281 B1 | 2/2004 | Chambers et al. | |
| 6,998,252 B1 | 2/2006 | Moss et al. | |
| 7,015,024 B1 | 3/2006 | Moss et al. | |
| 7,045,136 B1 | 5/2006 | Moss et al. | |
| 7,045,313 B1 | 5/2006 | Moss et al. | |
| 7,795,017 B2 | 9/2010 | Robinson et al. | |
| 8,288,125 B2 | 10/2012 | Howley et al. | |
| 8,309,326 B2 | 11/2012 | Howley et al. | |
| 8,414,900 B2 | 4/2013 | Howley et al. | |
| 8,435,543 B2 | 5/2013 | Howley et al. | |
| 8,623,379 B2 | 1/2014 | Robinson et al. | |
| 8,859,495 B2 | 10/2014 | Bamdad et al. | |
| 8,916,172 B2 | 12/2014 | Moss et al. | |
| 9,133,478 B2 | 9/2015 | Moss et al. | |
| 9,133,480 B2 | 9/2015 | Moss et al. | |
| 9,295,702 B2 | 3/2016 | Malarme et al. | |
| 9,453,239 B2 | 9/2016 | Moss et al. | |
| 9,683,020 B2 | 6/2017 | Compans et al. | |
| 9,879,231 B2 | 1/2018 | Moss et al. | |
| 10,072,058 B2 | 9/2018 | Wang et al. | |
| 10,258,684 B2 | 4/2019 | Van Der Burg et al. | |
| 2003/0215794 A1 | 11/2003 | Kawaoka et al. | |
| 2004/0109876 A1 | 6/2004 | Yamamoto et al. | |
| 2005/0036985 A1 | 2/2005 | Ensoli | |
| 2005/0214256 A1 | 9/2005 | Megede et al. | |
| 2006/0051759 A1 | 3/2006 | Salceda et al. | |
| 2006/0088909 A1 | 4/2006 | Compans et al. | |
| 2006/0099225 A1 | 5/2006 | Bavari et al. | |
| 2006/0127413 A1 | 6/2006 | Sutter et al. | |
| 2006/0216702 A1 | 9/2006 | Compans et al. | |
| 2006/0286074 A1 | 12/2006 | Tang et al. | |
| 2007/0160627 A1 | 7/2007 | Staib et al. | |

(Continued)

FOREIGN PATENT DOCUMENTS

| | | | |
|---|---|---|---|
| EP | 0538496 A1 | 5/1993 | |
| EP | 2402451 A2 | 1/2012 | |

(Continued)

OTHER PUBLICATIONS

GenBank Accession AFV31202, glycoprotein [Marburg marburgvirus], 2013.*
US, 2019/0117758, A1, U.S. Appl. No. 15/543,139, Robinson et al., Apr. 25, 2019.
US 2019/0184009, A1, U.S. Appl. No. 16/305,305, Guirakhoo et al., Jun. 20, 2019.
US 2019/0290745, A1, U.S. Appl. No. 16/068,527, Robinson et al., Sep. 26, 2019.
US. 2019/0382453, A1, U.S. Appl. No. 16/077,215, Robinson Harriet, Dec. 19, 2019.

(Continued)

*Primary Examiner* — Benjamin P Blumel
(74) *Attorney, Agent, or Firm* — Knowles Intellectual Properties Strategies, LLC

(57) ABSTRACT

The compositions and methods are described for generating an immune response to an antigen. The compositions and methods described herein relate to a modified vaccinia Ankara (MVA) vector encoding one or more viral antigens as a fusion product with a viral glycoprotein and matrix protein for generating a protective immune response to a subject to which the vector is administered. The compositions and methods of the present invention are useful both prophylactically and therapeutically and may be used to prevent and/or treat diseases.

14 Claims, 7 Drawing Sheets
Specification includes a Sequence Listing.

(56) References Cited

U.S. PATENT DOCUMENTS

| | | | |
|---|---|---|---|
| 2008/0193483 A1* | 8/2008 | Moss | C07K 14/005 424/232.1 |
| 2008/0199493 A1 | 8/2008 | Picker et al. | |
| 2009/0069367 A1 | 3/2009 | Bamdad | |
| 2009/0092628 A1 | 4/2009 | Mullins et al. | |
| 2010/0047277 A1 | 2/2010 | Compans et al. | |
| 2010/0196419 A1 | 8/2010 | Compans et al. | |
| 2010/0330190 A1 | 12/2010 | Compans et al. | |
| 2012/0052082 A1 | 3/2012 | Compans et al. | |
| 2012/0219576 A1 | 8/2012 | Branco et al. | |
| 2012/0263750 A1 | 10/2012 | Moss et al. | |
| 2012/0289760 A1 | 11/2012 | Hill et al. | |
| 2013/0101618 A1 | 4/2013 | Sullivan et al. | |
| 2013/0280215 A1 | 10/2013 | Robinson | |
| 2014/0050759 A1 | 2/2014 | Falkner et al. | |
| 2014/0322265 A1 | 10/2014 | Chaplin et al. | |
| 2015/0299290 A1 | 10/2015 | Boons et al. | |
| 2016/0040135 A1 | 2/2016 | Moss et al. | |
| 2016/0144011 A1 | 5/2016 | Collins et al. | |
| 2016/0251406 A1 | 9/2016 | Schlom et al. | |
| 2017/0304427 A1* | 10/2017 | Volkmann | A61P 31/12 |
| 2019/0290745 A1* | 9/2019 | Robinson | A61K 39/0011 |

FOREIGN PATENT DOCUMENTS

| | | |
|---|---|---|
| WO | WO 1994/012617 A1 | 6/1994 |
| WO | WO 1998/008539 A1 | 3/1998 |
| WO | WO 1999/063062 A1 | 12/1999 |
| WO | WO 2000/003030 A1 | 1/2000 |
| WO | WO 2002/072754 A2 | 9/2002 |
| WO | WO 2003/078640 A2 | 9/2003 |
| WO | WO 2003/097845 A1 | 11/2003 |
| WO | WO 2004/048582 A2 | 6/2004 |
| WO | WO 2005/048857 A2 | 6/2005 |
| WO | WO 2006/026667 A2 | 3/2006 |
| WO | WO 2006/077161 A1 | 7/2006 |
| WO | WO 2007/012691 A1 | 2/2007 |
| WO | WO 2007/147528 A1 | 12/2007 |
| WO | WO 2008/142479 A2 | 11/2008 |
| WO | WO 2010/062757 A1 | 6/2010 |
| WO | WO 2011/047031 A2 | 4/2011 |
| WO | WO 2011/103417 A2 | 8/2011 |
| WO | WO 2013/059498 A1 | 5/2013 |
| WO | WO 2014/005958 A1 | 1/2014 |
| WO | WO 2015/009946 A1 | 1/2015 |
| WO | WO 2015/066715 A1 | 5/2015 |
| WO | WO 2015/0175340 A1 | 11/2015 |
| WO | WO 2016/034678 A2 | 3/2016 |
| WO | WO 2016/068919 A1 | 5/2016 |
| WO | WO 2016/115116 A1 | 7/2016 |
| WO | WO 2017/120577 A1 | 7/2017 |
| WO | WO 2017/136419 A1 | 8/2017 |
| WO | WO 2017/143016 A1 | 8/2017 |
| WO | WO 2017/210181 A1 | 12/2017 |
| WO | WO 2018/195447 A1 | 10/2018 |
| WO | WO 2019/018501 A1 | 1/2019 |
| WO | WO 2019/040846 A1 | 2/2019 |
| WO | WO 2019/060356 A1 | 3/2019 |
| WO | WO 2020/247547 A1 | 12/2020 |

OTHER PUBLICATIONS

US, 2020/0171141, A1, U.S. Appl. No. 16/631,489, Guirakhoo et al., Jun. 4, 2020.
US, 2020/0282036, A1, U.S. Appl. No. 16/648,693, Guirakhoo et al., Sep. 10, 2020.
U.S. Appl. No. 16/641,728, filed Feb. 25, 2020, Guirakhoo Farshad.
U.S. Appl. No. 17/000,768, filed Aug. 24, 2020, Guirakhoo et al.
Hessel, et al., MVA Vectors Expressing Conserved Influenza Proteins Protect Mice Against Lethal Challenge with H5N1, H942 and H7N1 Viruses, 2014, PLOS One, vol. 9, No. 2.
Adu-Gyamfi, et al. "The Ebola Virus Matrix Protein Penetrates into the Plasma Membrane," J. Infect. Dis., Jan. 7, 2014, vol. 210, No. 1, pp. 99-110.
Alharbi et al., "Enhancing cellular immunogenicity of MVA-vectored vaccines by utilizing the F11 lendogenous promoter", Vaccine, 2015, 34(1), 49-55.
Anderson et al., "Plasmid DNA and viral vector-based vaccines for the treatment of cancer", Vaccine, 2007, 25, 24-34.
Antoine et al., "The complete genomic sequence of the modified vaccinia ankara strain: Comparison with other orthopoxviruses", Virology, 1998, 244, 365-396.
Brault, A.C., Domi, A., McDonald, E. et al., "A Zika Vaccine Targeting NS1 Protein Protects Immunocompetent Adult Mice in a Lethal Challenge Model", Sci Rep., 2017, 7, 14769; https://doi.org/10.1038/s41598-017-15039-8.
Brayman M, Thathiah A, Carson DD., "MUC1: a multifunctional cell surface component of reproductive tissue epithelia", Reprod. Biol Endocrinol., Jan. 7, 2004,2:4. doi: 10.1186/1477-7827-2-4. PMID: 14711375; PMCID: PMC320498.
Domi, A., Feldmann, F., Basu, R. et al., "A Single Dose of Modified Vaccinia Ankara expressing Ebola Virus Like Particles Protects Nonhuman Primates from Lethal Ebola Virus Challenge", Sci Rep.,2018, 8, 864; https://doi.org/10.1038/s41598-017-19041-y.
Earl et al., "Recombinant modified vaccinia virus ankara provides durable protection against disease caused by immunodeficiency virus as well as long term immunity to an orthopoxvirus in a non-human primate", Virology, 2007, 366(1), 84-87.
European Search Report and Written Opinion for EP17736506 dated Jul. 22, 2019.
European Search Report and Written Opinion for EP17736506 dated May 27, 2020.
Fend L., et al., "Intravenous injection of MVA virus targets CD8+ lymphocytes to tumors to control tumor growth upon combinatorial treatment with a TLR9 agonist", Cancer Immunology Research, 2014, 2(12), 1163-1174.
Gendler SJ, "MUC1, the renaissance molecule", J. Mammary Gland Biol Neoplasia., 2001, 6 (3,: 339-353.
Goepfert PA, et al., National Institutes of Allergy and Infectious Diseases HIV Vaccines Trials Network., "Specificity and 6-month durability of immune responses induced by DNA and recombinant modified vaccinia Ankara vaccines expressing HIV-1 virus-like particles", J Infect Dis. Jul. 1, 2014;210(1):99-110. doi: 10.1093/infdis/jiu003. Epub Jan. 7, 2014. PMID: 24403557; PMCID: PMC4072895.
Goepfert PA,et al., "National Institute of Allergy and Infectious Diseases HIV Vaccine Trials Network. Phase 1 safety and immunogenicity testing of DNA and recombinant modified vaccinia Ankara vaccines expressing HIV-1 virus-like particles", J Infect Dis. Mar. 1, 2011;203(5):610-9. doi: 10.1093/infdis/jiq105. Epub Jan. 31, 2011. PMID: 21282192; PMCID: PMC3072720.
Holmes, Ket al., Assembly Pathway of Hepatitis B Core Vims-like Particles from Genetically 13 Fused Dimers. The Journal of Biological Chemistry, May 7, 2015. vol. 290, No. 26, pp. 16238-16245.
International Search Report from PCT Patent Application No. PCT/US2017/012704, dated Apr. 13, 2017.
Lindén SK, et al., "MUC1 limits Helicobacter pylori infection both by steric hindrance and by acting as a releasable decoy", PLoS Pathog, Oct. 2009, 5(10), e1000617. doi: 10.1371/journal.ppat. 1000617. Epub Oct. 9, 2009. PMID: 19816567; PMCID: PMC2752161.
Lou Ming: "A virus-life particle of HBV preS elicits robust immune responses—5th World Congress on hepatitis and liver diseases 2nd International Conference on Pancreatic Cancer and Liver Diseases", Journal of Liver, 2017, 6; Aug. 10, 2017.
Mackett et al., "Vaccinia virus expression vectors", J. Gen. Virology, 1986, 67, 2067-2082.
Malherbe, Delphine C. et al., "Modified vaccinia Ankara vaccine expressing Marburg virus-like particles protects guinea pigs from lethal Marburg virus infection", Vaccines, 2020, 5(1), 78.
Manuel E.R. et al., "Intergenic region 3 of modified vaccinia ankara is a functional site for insert gene expression and allows for potent antigenA-specific immune responses", Virology, Elsevier, Amsterdam, NL, 2010, 403(2), Aug. 2010 (Aug. 1, 2010), pp. 155-162).
Mascola et al., "Novel vaccine technologies for the 21st century", Natures Review: Immunology, 2020, 20, 87-88.

(56) References Cited

OTHER PUBLICATIONS

Mittler, et al. "The Cytoplasmic Domain of Marburg Virus GP Modulates Early Steps of Viral Infection," Journal of Virology, Jun. 15, 2011, vol. 85, No. 6, pp. 8188-8196.
Moss et al., "Reflections on the early development of poxvirus vectors", Vaccine, 2013, 31(39), 4220-4222.
Orubu et al., "Expression and cellular immunogenicity of a transgenic antigen driven by endogenous poxviral early promoters at their authentic loci in MVA", PLOS One, 2012, 7(6), e40167 doi:10.1371/journal.pone.0040167.
Osborne et al., "An entomopoxvirus homologue of the vaccinia virus D13L-encoded rifampicin resistance protein", Journal of General Virology, 1996, 77, 839-846.
Pejawar-Gaddy et al., "Generation 1-16 of a tumor vaccine candidate based on conjugation of a MUC1 peptide to polyionic papilloma virus virus-like particles", Cancer Immunology, 2010, 59(11), 1685-1696.
Rolland et al., "HIV-1 group M conserved element vaccine", PLoS Pathogens, 2007, 3(11), 1551-1555.
Salvato et al., A "Single Dose of Modified Vaccinia Ankara Expressing Lassa Virus-like Particles Protects Mice from Lethal Intracerebral Virus Challenge", Pathogens, 2019, 8:133.
Singh PK, Hollingsworth MA., "Cell surface-associated mucins in signal transduction", Trends Cell Biol. Sep. 2006;16(9):467-76. doi: 10.1016/j.tcb.2006.07.006. Epub Aug. 9, 2006. PMID: 16904320.
Staib et al., "Transient host range selection for genetic engineering of modified vaccinia virus ankara", Biotechniques, 2000, 28, 1137-1148.
Swenson et al., "Generation of Marburg virus-like particles by co-expression of glycoprotein and matrix protein", FEMS Immunology and Medical Microbiology., 2004, 40(1), pp. 27-31.
Thompson M, et al., "DNA/MVA Vaccination of HIV-1 Infected Participants with Viral Suppression on Antiretroviral Therapy, followed by Treatment Interruption: Elicitation of Immune Responses without Control of Re-Emergent Virus", PLoS One, 2016, 11(10): e0163164. https://doi.org/10.1371/journal.pone.0163164.
Timm et al., "Genetic stability of recombinant MVA-BN", Vaccine, 2006, 24, 4618-4621.
Urata, S.; Yasuda, J., "Cis- and cell-type-dependent trans-requirements for Lassa virus-like particle production", J. Gen. Virol., 2015, 96 Pt 7, 1626-1635.
Vietheer et al., "Immunizations with chimeric hepatitis B virus-like particles to induce potential anti-hepatitis C virus neutralizing antibodies", Antiviral Therapy, 2007, 12, 477-487.
Wang et al., "Modified H5 promoter improves stability of insert genes while maintaining immunogenicity during extended passage of genetically engineered MVA vaccines", Vaccine, Feb. 10, 2010; 28(6): 1547. doi:10.1016/j.vaccine.2009.11.056.
Wyatt et al., "Development of a replication-deficient recombinant vaccinia virus vaccine effective against parainfluenza virus 3 infection in an animal model", Vaccine, 1996, 14(15), 1451-1458.
Xiaodan, Cai, et al., "A virus-like particle of the hepatitis B virus preS antigen elicits robust neutralizing antibodies and T cell responses in mice", Antiviral Research, 2018, 149, 48-57.
US, 2021/0100891, A1, U.S. Appl. No. 17/000,768, Guirakhoo et al., Apr. 8, 2021.
US, 2021/0220469, A1, U.S. Appl. No. 16/641,728, Guirakhoo, Jul. 22, 2021.
U.S. Appl. No. 17/368,761, filed Jul. 6, 2021, Guirakhoo.
U.S. Appl. No. 17/409,574, filed Aug. 23, 2021, Robinson.
GenBank Accession AFV312002, glycoprotein [Marburg Marburgvirus], Protein—NCBI; 3 pages; 2013.

\* cited by examiner

VACCINIA VIRAL VECTORS ENCODING CHIMERIC VIRUS LIKE PARTICLES

CROSS REFERENCE TO RELATED APPLICATIONS

This application is a continuation of U.S. patent application Ser. No. 16/068,527, filed Jul. 6, 2018, which is a National Phase application under 35 U.S.C. § 371 of International Application No. PCT/US2017/012704, filed on Jan. 9, 2017, which claims the benefit of U.S. provisional patent application U.S. 62/276,479 filed Jan. 8, 2016, and U.S. provisional patent application U.S. 62/301,885 filed Mar. 1, 2016, the disclosures of which are hereby incorporated by reference in their entirety.

INCORPORATION BY REFERENCE

The contents of the text file named "19101-002US1CON_SequenceListing" which was created on Feb. 20, 2020 and is 59.6 KB in size, are hereby incorporated by reference in their entirety.

BACKGROUND OF THE INVENTION

In 2016, there will be an estimated 1,685,210 new cancer cases diagnosed and 595,690 cancer deaths in the US (Cancer Facts & Figures 2016, American Cancer Society 2016). Cancer vaccines based on human tumor-associated antigens (TAA) have been tested in patients with advanced or recurrent cancer, in combination with or following standard therapy. The immunogenicity and therapeutic efficacy of cancer vaccines has been difficult to properly evaluate due to the multiple highly suppressive effects of the tumor microenvironment and the actions of standard therapy on the patient's immune system. In animal models of human cancer, vaccines administered in the prophylactic setting are most immunogenic and effectively prevent cancer development and progression.

Vaccines based on human TAAs are immunogenic and safe and capable of eliciting long-term memory that is important for cancer prevention.

One particular TAA is MUC-1 which is a member of the mucin family and encodes a membrane bound, glycosylated phosphoprotein. MUC1 has a core protein mass of 120-225 kDa which increases to 250-500 kDa with glycosylation. It extends 200-500 nm beyond the surface of the cell (Brayman M, Thathiah A, Carson D D, 2004, Reprod Biol Endocrinol. 2: 4). The protein is anchored to the apical surface of many epithelia by a transmembrane domain. These repeats are rich in serine, threonine and proline residues which permits heavy o-glycosylation (Brayman M, Thathiah A, Carson D D, 2004, Reprod Biol Endocrinol. 2: 4). Multiple alternatively spliced transcript variants that encode different isoforms of this gene have been reported.

The cytoplasmic tail of MUC-1 is 72 amino acids long and contains several phosphorylation sites (Singh P K, Hollingsworth M A (August 2006), Trends Cell Biol. 16 (9): 467-476). The protein serves a protective function by binding to pathogens and also functions in a cell signaling capacity (Linden S K et al. 2009, PLoS Pathog. 5 (10): e1000617).

Overexpression, aberrant intracellular localization, and changes in glycosylation of this protein have been associated with carcinomas. Specifically, MUC-1 overexpression is often associated with colon, breast, ovarian, lung and pancreatic cancers (Gendler S J (July 2001), J. Mammary Gland Biol Neoplasia. 6 (3): 339-353).

Currently there is no US approved vaccine for humans against cancer. What is needed are immunogenic vaccine compositions and methods of use to prevent and treat cancer caused by neoplasms.

SUMMARY OF THE INVENTION

The compositions and methods of the invention described herein are useful for generating an immune response to a tumor associated antigen (TAA) in a subject in need thereof. Advantageously, the compositions and methods may be used prophylactically to immunize a subject against cancer-associated antigens, or used therapeutically to treat or ameliorate the onset and severity of disease in a subject in need thereof.

In a first aspect, the present invention is a recombinant modified vaccinia Ankara (MVA) vector comprising a Tumor associated antigen (TAA)-encoding sequence (TAA sequence) and a matrix protein-encoding sequence (matrix protein sequence), wherein both the TAA sequence and matrix protein sequence are under the control of promoters compatible with poxvirus expression systems.

In one embodiment, the TAA sequence and the matrix protein sequence are inserted into one or more deletion sites of the MVA vector.

In one embodiment, the TAA is selected from the group consisting of Oncofetal Antigen/immature Laminin Receptor Protein (OFA/iLRP), Alphafetoprotein (AFP), Carcinoembryonic antigen (CEA), CA-125, MUC-1, Epithelial tumor antigen (ETA), Tyrosinase, Melanoma-associated antigen (MAGE), abnormal products of ras, abnormal products of p53, or immunogenic fragments thereof.

In one embodiment, the TAA is MUC-1.

In one embodiment, the TAA is OFA/iLRP.

In one embodiment, the TAA is CEA.

In one embodiment, the matrix protein is a Marburgvirus matrix protein.

In one embodiment, the matrix protein is a Marburg virus VP40 matrix protein.

In one embodiment, the matrix protein is an Ebola virus matrix protein.

In one embodiment, the matrix protein is a Ebola virus VP40 matrix protein.

In one embodiment, the matrix protein is a Sudan virus matrix protein.

In one embodiment, the matrix protein is a Sudan virus VP40 matrix protein.

In one embodiment, the matrix protein is a human immunodeficiency virus type 1 (HIV-1) matrix protein.

In one embodiment, the matrix protein is a human immunodeficiency virus type 1 (HIV-1) matrix protein encoded by the gag gene.

In one embodiment, the matrix protein is a Lassa virus matrix protein.

In one embodiment, the matrix protein is a Lassa virus Z protein.

In one embodiment, the matrix protein is a fragment of a Lassa virus Z protein.

In one embodiment, the matrix protein is a matrix protein of a virus in the Filoviridae virus family.

In one embodiment, the matrix protein is a matrix protein of a virus in the Retroviridae virus family.

In one embodiment, the matrix protein is a matrix protein of a virus in the Arenaviridae virus family.

In one embodiment, the matrix protein is a matrix protein of a virus in the Flaviviridae virus family.

In one embodiment, the TAA sequence and the matrix protein sequence are inserted into the MVA vector in a natural deletion site, a modified natural deletion site, or between essential or non-essential MVA genes.

In another embodiment, the TAA sequence and the matrix protein sequence are inserted into the same natural deletion site, a modified natural deletion site, or between the same essential or non-essential MVA genes.

In another embodiment, the TAA sequence is inserted into a deletion site selected from I, II, III, IV, V or VI and the matrix protein sequence is inserted into a deletion site selected from I, II, III, IV, V or VI.

In another embodiment, the TAA sequence and the matrix protein sequence are inserted into different natural deletion sites, different modified deletion sites, or between different essential or non-essential MVA genes.

In another embodiment, the TAA sequence is inserted in a first deletion site and matrix protein sequence is inserted into a second deletion site.

In a particular embodiment, the TAA sequence is inserted between two essential and highly conserved MVA genes; and the matrix protein sequence is inserted into a restructured and modified deletion III.

In one embodiment, the deletion III is modified to remove non-essential sequences and insert the matrix protein sequence between essential genes.

In a particular embodiment, the matrix protein sequence is inserted between MVA genes, I8R and G1L.

In a particular embodiment, the TAA sequence is inserted between two essential and highly conserved MVA genes to limit the formation of viable deletion mutants.

In a particular embodiment, the TAA protein sequence is inserted between MVA genes, I8R and G1L.

In one embodiment, the promoter is selected from the group consisting of Pm2H5, Psyn II, and mH5 promoters or combinations thereof.

In one embodiment, the TAA sequence is optimized. In a particular embodiment, the TAA sequence is optimized by changing selected codons to other synonymous codons that are optimal for protein expression by MVA, interrupting homopolymer stretches using silent mutations, interrupting transcription terminator motifs using silent mutations, or leading to expression of the transmembrane (rather than secreted) form of TAA, and combinations thereof.

In one embodiment, the recombinant MVA viral vector expresses TAA and matrix proteins that assemble into VLPs.

In a second aspect, the present invention provides a pharmaceutical composition comprising the recombinant MVA vector of the present invention and a pharmaceutically acceptable carrier.

In one embodiment, the recombinant MVA vector is formulated for intraperitoneal, intramuscular, intradermal, epidermal, mucosal or intravenous administration.

In a third aspect, the present invention provides a pharmaceutical composition comprising two recombinant MVA vectors, wherein each recombination MVA vector comprises a TAA sequence, wherein (i) the TAA sequence of the first recombinant MVA vector is different than the TAA sequence of the second recombinant MVA vector.

In one embodiment, the TAA sequence and the matrix protein sequence are inserted into one or more deletion sites of the MVA vector.

In one embodiment, the TAA is selected from the group consisting of Oncofetal Antigen/immature Laminin Receptor Protein (OFA/iLRP), Alphafetoprotein (AFP), Carcinoembryonic antigen (CEA), CA-125, MUC-1, Epithelial tumor antigen (ETA), Tyrosinase, Melanoma-associated antigen (MAGE), and abnormal products of ras, and p53 or immunogenic fragments thereof.

In one embodiment, the TAA is MUC-1.

In one embodiment, the TAA is Oncofetal Antigen/immature Laminin Receptor Protein (OFA/iLRP).

In one embodiment, the TAA is Carcinoembryonic antigen (CEA).

In one embodiment, the TAA of the first recombinant MVA vector is MUC-1 and the TAA of the second recombinant MVA vector is Oncofetal Antigen/immature Laminin Receptor Protein (OFA/iLRP).

In one embodiment, the TAA of the first recombinant MVA vector is MUC-1 and the TAA of the second recombinant MVA vector is Carcinoembryonic antigen (CEA).

In one embodiment, the TAA of the first recombinant MVA vector is Oncofetal Antigen/immature Laminin Receptor Protein (OFA/iLRP) and the TAA of the second recombinant MVA vector is Carcinoembryonic antigen (CEA).

In one embodiment, the TAA sequence and the matrix protein sequence are inserted into the MVA vector in a natural deletion site, a modified natural deletion site, or between essential or non-essential MVA genes.

In another embodiment, the TAA sequence and the matrix protein sequence are inserted into the same natural deletion site, the same modified natural deletion site, or between the same essential or non-essential MVA genes.

In another embodiment, the TAA sequence is inserted into a deletion site selected from I, II, III, IV, V or VI and the matrix protein sequence is inserted into a deletion site selected from I, II, III, IV, V or VI.

In another embodiment, the TAA sequence and the matrix protein sequence are inserted into different natural deletion sites, different modified deletion sites, or between different essential or non-essential MVA genes.

In another embodiment, the TAA sequence is inserted in a first deletion site and matrix protein sequence is inserted into a second deletion site.

In a particular embodiment, the TAA sequence is inserted between two essential and highly conserved MVA genes; and the matrix protein sequence is inserted into a restructured and modified deletion III.

In one embodiment, the deletion III is modified to remove non-essential sequences and insert the matrix protein sequence between essential genes.

In a particular embodiment, the matrix protein sequence is inserted between MVA genes, I8R and G1L.

In a particular embodiment, the TAA sequence is inserted between two essential and highly conserved MVA genes to limit the formation of viable deletion mutants.

In a particular embodiment, the TAA protein sequence is inserted between MVA genes, I8R and G1L.

In one embodiment, the promoter is selected from the group consisting of Pm2H5, Psyn II, and mH5 promoters or combinations thereof.

In one embodiment, the TAA sequence is optimized. In a particular embodiment, the TAA sequence is optimized by changing selected codons to other synonymous codons that are optimal for protein expression by MVA, interrupting homopolymer stretches using silent mutations, interrupting transcription terminator motifs using silent mutations, or leading to expression of the transmembrane (rather than secreted) form of TAA, and combinations thereof.

In one embodiment, the recombinant MVA viral vector expresses TAA and matrix proteins that assemble into VLPs.

In a second aspect, the present invention provides a pharmaceutical composition comprising the recombinant MVA vector of the present invention and a pharmaceutically acceptable carrier.

In one embodiment, the recombinant MVA vector is formulated for intraperitoneal, intramuscular, intradermal, epidermal, mucosal or intravenous administration.

In a particular embodiment, the TAA sequence of the first recombinant MVA vector is from a different species than the TAA sequence of the second recombinant MVA vector.

In a fourth aspect, the present invention provides a pharmaceutical composition comprising three or more recombinant MVA vectors, wherein each recombinant MVA vector comprises a TAA sequence, wherein (i) the three or more recombinant MVA vectors contain different TAA sequences.

In one embodiment, the TAA sequences are MUC-1, Oncofetal Antigen/immature Laminin Receptor Protein (OFA/iLRP), and Carcinoembryonic antigen (CEA).

In a particular embodiment, the TAA sequences are from the same species.

In a particular embodiment, the TAA sequences are from different species.

In a fifth aspect, the present invention provides a method of inducing an immune response to a neoplasm in a subject in need thereof, said method comprising administering a composition comprising the immunogenic vectors described herein to the subject in an amount sufficient to induce an immune response.

In one embodiment, the immune response is a humoral immune response, a cellular immune response or a combination thereof.

In a particular embodiment, the immune response comprises production of binding antibodies against the TAA.

In a particular embodiment, the immune response comprises production of neutralizing antibodies against the TAA.

In a particular embodiment, the immune response comprises production of non-neutralizing antibodies against the TAA.

In a particular embodiment, the immune response comprises production of a cell-mediated immune response against the TAA.

In a particular embodiment, the immune response comprises production of neutralizing and non-neutralizing antibodies against the TAA.

In a particular embodiment, the immune response comprises production of neutralizing antibodies and cell-mediated immunity against the TAA.

In a particular embodiment, the immune response comprises production of non-neutralizing antibodies and cell-mediated immunity against the TAA.

In a particular embodiment, the immune response comprises production of neutralizing antibodies, non-neutralizing antibodies, and cell-mediated immunity against the TAA.

In one embodiment, the neoplasm is selected from leukemia (e.g. myeloblastic, promyelocytic, myelomonocytic, monocytic, erythroleukemia, chronic myelocytic (granulocytic) leukemia, and chronic lymphocytic leukemia), lymphoma (e.g. Hodgkin's disease and non-Hodgkin's disease), fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilms' tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia.

In another embodiment, the TAA is MUC-1 and the neoplasm is selected from Adenocarcinomas (breast, colorectal, pancreatic, other), Carcinoid tumor, Chordoma, Choriocarcinoma, Desmoplastic small round cell tumor (DSRCT), Epithelioid sarcoma, Follicular dendritic cell sarcoma, interdigitating dendritic cell/reticulum cell sarcoma, Lung: type II pneumocyte lesions (type II cell hyperplasia, dysplastic type II cells, apical alveolar hyperplasia), Anaplastic large-cell lymphoma, diffuse large B cell lymphoma (variable), plasmablastic lymphoma, primary effusion lymphoma, Epithelioid mesotheliomas, Myeloma, Plasmacytomas, Perineurioma, Renal cell carcinoma, Synovial sarcoma (epithelial areas), Thymic carcinoma (often), Meningioma or Paget's disease.

In a sixth aspect, the present invention provides a method of treating cancer comprising administering the recombinant MVA vector of the present invention to a subject in need thereof in an effective amount to treat cancer.

In a seventh aspect, the present invention provides a method of reducing growth of a neoplasm in a subject, said method comprising administering the recombinant MVA vector of the present invention to the subject in an effective amount to reduce growth of a neoplasm.

In an eighth aspect, the present invention provides a method of preventing growth of a neoplasm in a subject, said method comprising administering the recombinant MVA vector of the present invention to the subject in a prophylactically effective amount.

In one embodiment, the subject expresses tumor cell markers, but not yet symptomatic. In a particular embodiment, treatment results in prevention of a symptomatic disease.

In another embodiment, the subject expresses tumor cell markers but exhibits minimal symptoms of cancer.

In another embodiment, the method results in amelioration of at least one symptom of cancer.

In a ninth aspect, the present invention provides a method manufacturing a recombinant modified vaccinia Ankara (MVA) viral vector comprising inserting at least one TAA sequence into the MVA vector wherein the at least one TAA sequence is operably linked to a promoter compatible with poxvirus expression systems.

In one embodiment, the method comprises inserting at least one matrix protein sequence into the MVA vector wherein the at least one TAA sequence is operably linked to a promoter compatible with poxvirus expression systems.

DETAILED DESCRIPTION OF THE INVENTION

Figure 1:
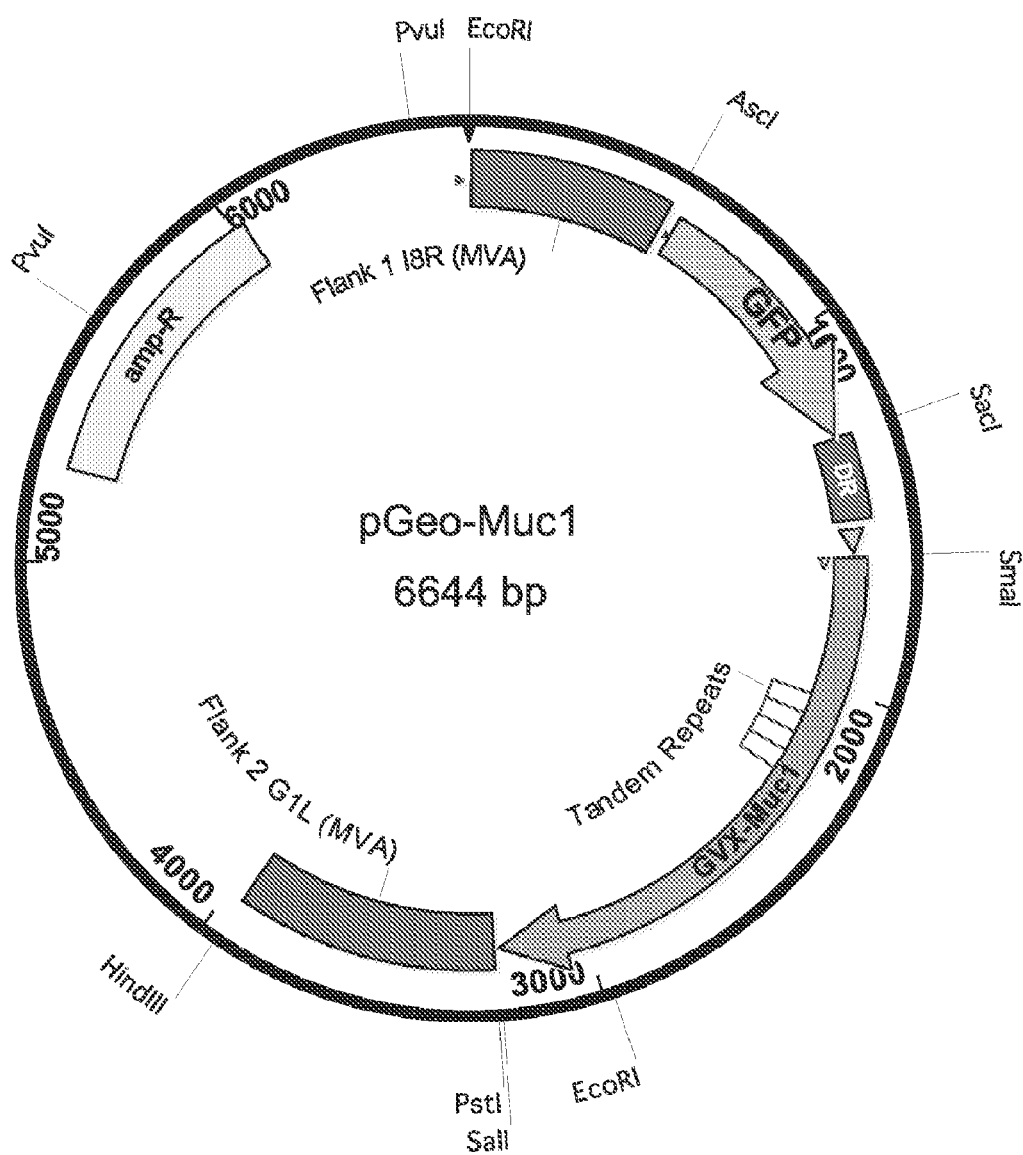
FIG. 1 is a schematic for the shuttle vector for MUC1 (pGeo-Muc1).

Compositions and methods are provided to produce an immune response to a tumor associated antigen (TAA), in a subject in need thereof. The compositions and methods of the present invention can be used to prevent or delay formation of neoplasm or to treat neoplasm or disease associated therewith (such as cancer) in a subject in need thereof. In one embodiment, treatment limits neoplasm development, growth and/or the severity of neoplasm-associated disease such as cancer.

Ideal immunogenic compositions or vaccines have the characteristics of safety, efficacy, scope of protection and longevity, however, compositions having fewer than all of these characteristics may still be useful in preventing neoplasm growth or limiting symptoms or disease progression in an exposed subject treated prior to the development of symptoms. In one embodiment the present invention provides a vaccine that permits at least partial, if not complete, protection after a single immunization.

In one embodiment, the composition is a recombinant vaccine or immunogenic vector that comprises one or more nucleic acid sequences encoding Tumor associated antigens (TAA) or immunogenic fragments thereof.

In one embodiment, the composition is a recombinant vaccine or immunogenic vector that comprises an extracellular fragment of MUC-1.

In one embodiment, the composition is a recombinant vaccine or immunogenic vector that comprises an intracellular fragment of MUC-1.

In one embodiment, the composition is a recombinant vaccine or immunogenic vector that comprises an extracellular and an intracellular fragment of MUC-1.

In one embodiment, the composition is a recombinant vaccine or immunogenic vector that comprises an extracellular fragment of MUC-1, an intracellular fragment of MUC-1, and a transmembrane domain of a glycoprotein (GP) of Marburg virus.

In one embodiment, the composition is a recombinant vaccine or immunogenic vector that comprises an extracellular fragment of a TAA, an intracellular fragment of a TAA, and a transmembrane domain of a GP of a virus in the Filoviridae virus family.

In one embodiment, the vector expresses proteins that form VLPs and generate and immune response to a TAA or immunogenic fragment thereof.

In exemplary embodiments, the immune responses are long-lasting and durable so that repeated boosters are not required, but in one embodiment, one or more administrations of the compositions provided herein are provided to boost the initial primed immune response.

I. Definitions

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a peptide" includes a plurality of peptides. Thus, for example, a reference to "a method" includes one or more methods, and/or steps of the type described herein and/or which will become apparent to those persons skilled in the art upon reading this disclosure.

The term "antigen" refers to a substance or molecule, such as a protein, or fragment thereof, that is capable of inducing an immune response.

The term "binding antibody" or "bAb" refers to an antibody which either is purified from, or is present in, a body fluid (e.g., serum or a mucosal secretion) and which recognizes a specific antigen. As used herein, the antibody can be a single antibody or a plurality of antibodies. Binding antibodies comprise neutralizing and non-neutralizing antibodies.

The term "cancer" refers to a malignant neoplasm that has undergone characteristic anaplasia with loss of differentiation, increase rate of growth, invasion of surrounding tissue, and is capable of metastasis.

The term "cell-mediated immune response" refers to the immunological defense provided by lymphocytes, such as the defense provided by sensitized T cell lymphocytes when they directly lyse cells expressing foreign antigens and secrete cytokines (e.g., IFN-gamma.), which can modulate macrophage and natural killer (NK) cell effector functions and augment T cell expansion and differentiation. The cellular immune response is the $2^{nd}$ branch of the adaptive immune response.

The term "conservative amino acid substitution" refers to substitution of a native amino acid residue with a non-native residue such that there is little or no effect on the size, polarity, charge, hydrophobicity, or hydrophilicity of the amino acid residue at that position, and without resulting in substantially altered immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

The term "deletion" in the context of a polypeptide or protein refers to removal of codons for one or more amino acid residues from the polypeptide or protein sequence, wherein the regions on either side are joined together. The term deletion in the context of a nucleic acid refers to removal of one or more bases from a nucleic acid sequence, wherein the regions on either side are joined together.

The term "Ebola virus" refers to a virus of species Zaire ebolavirus and has the meaning given to it by the International Committee on Taxonomy of Viruses as documented in (Kuhn, J. H. et al. 2010 Arch Virol 155:2083-2103).

The term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment the fragment constitutes at least 10%, 20%, 30%, 40%, 50%, 60%, 70%, 80%, or 90% of the entire length of the reference polypeptide. In one embodiment, a fragment of a full-length protein retains activity of the full-length protein. In another embodiment, the fragment of the full-length protein does not retain the activity of the full-length protein.

The term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In one embodiment the fragment constitutes at least 10%, 20%, 30%, 40%, 50%, 60%, 70%, 80%, or 90% of the entire length of the reference nucleic acid sequence. In a preferred embodiment, a fragment of a nucleic acid encodes a peptide or polypeptide that retains activity of the full-length protein. In another embodiment, the fragment encodes a peptide or polypeptide that of the full-length protein does not retain the activity of the full-length protein.

As used herein, the term "growth inhibitory amount" refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

As used herein, the phrase "heterologous sequence" refers to any nucleic acid, protein, polypeptide or peptide sequence which is not normally associated in nature with another nucleic acid or protein, polypeptide or peptide sequence of interest.

As used herein, the phrase "heterologous gene insert" refers to any nucleic acid sequence that has been, or is to be inserted into the recombinant vectors described herein. The heterologous gene insert may refer to only the gene product encoding sequence or may refer to a sequence comprising a promoter, a gene product encoding sequence (such as GP, VP or Z), and any regulatory sequences associated or operably linked therewith.

The term "homopolymer stretch" refers to a sequence comprising at least four of the same nucleotides uninterrupted by any other nucleotide, e.g., GGGG or TTTTTTT.

The term "humoral immune response" refers to the stimulation of Ab production. Humoral immune response also refers to the accessory proteins and events that accompany antibody production, including T helper cell activation and cytokine production, affinity maturation, and memory cell generation. The humoral immune response is one of two branches of the adaptive immune response.

The term "humoral immunity" refers to the immunological defense provided by antibody, such as neutralizing Ab that can directly bind a neoplasm; or, binding Ab that identifies a neoplastic cell for killing by such innate immune responses as complement (C')-mediated lysis, phagocytosis, and natural killer cells.

The term "immunogenic composition" is a composition that comprises an antigenic molecule where administration of the composition to a subject results in the development in the subject of a humoral and/or a cellular immune response to the antigenic molecule of interest.

The term "immune response" refers to any response to an antigen or antigenic determinant by the immune system of a subject (e.g., a human). Exemplary immune responses include humoral immune responses (e.g., production of antigen-specific antibodies) and cell-mediated immune responses (e.g., production of antigen-specific T cells). Assays for assessing an immune response are known in the art and may comprise in vivo assays, such as assays to measure antibody responses and delayed type hypersensitivity responses. In an embodiment, the assay to measure antibody responses primarily may measure B-cell function as well as B-cell/T-cell interactions. For the antibody response assay, antibody titers in the blood may be compared following an antigenic challenge. As used herein, "antibody titers" can be defined as the highest dilution in post-immune sera that resulted in a value greater than that of pre-immune samples for each subject. The in vitro assays may comprise determining the ability of cells to divide, or to provide help for other cells to divide, or to release lymphokines and other factors, express markers of activation, and lyse target cells. Lymphocytes in mice and man can be compared in in vitro assays. In an embodiment, the lymphocytes from similar sources such as peripheral blood cells, splenocytes, or lymph node cells, are compared. It is possible, however, to compare lymphocytes from different sources as in the non-limiting example of peripheral blood cells in humans and splenocytes in mice. For the in vitro assay, cells may be purified (e.g., B-cells, T-cells, and macrophages) or left in their natural state (e.g., splenocytes or lymph node cells). Purification may be by any method that gives the desired results. The cells can be tested in vitro for their ability to proliferate using mitogens or specific antigens. The ability of cells to divide in the presence of specific antigens can be determined using a mixed lymphocyte reaction (MLR) assay. Supernatant from the cultured cells can be tested to quantitate the ability of the cells to secrete specific lymphokines. The cells can be removed from culture and tested for their ability to express activation antigens. This can be done by any method that is suitable as in the non-limiting example of using antibodies or ligands which bind to the activation antigen as well as probes that bind the RNA coding for the activation antigen.

The term "improved therapeutic outcome" relative to a subject diagnosed as having a neoplasm or cancer refers to a slowing or diminution in the growth of a tumor, or detectable symptoms associated with tumor growth.

The term "inducing an immune response" means eliciting a humoral response (e.g., the production of antibodies) or a cellular response (e.g., the activation of T cells) directed against a TAA in a subject to which the composition (e.g., a vaccine) has been administered.

The term "insertion" in the context of a polypeptide or protein refers to the addition of one or more non-native amino acid residues in the polypeptide or protein sequence. Typically, no more than about from 1 to 6 residues (e.g. 1 to 4 residues) are inserted at any one site within the polypeptide or protein molecule.

The term "Marburg virus" refers to a virus of species Marburg marburgvirus and has the meaning given to it by the International Committee on Taxonomy of Viruses as documented in (Kuhn, J. H. et al. 2010 Arch Virol 155: 2083-2103).

The term "marker" refers to is meant any protein or polynucleotide having an alteration in expression level or activity that is associated with a disease or disorder.

The term "modified vaccinia Ankara," "modified vaccinia ankara," "Modified Vaccinia Ankara," or "MVA" refers to a highly attenuated strain of vaccinia virus developed by Dr. Anton Mayr by serial passage on chick embryo fibroblast cells; or variants or derivatives thereof. MVA is reviewed in (Mayr, A. et al. 1975 Infection 3:6-14; Swiss Patent No. 568,392).

The term "neoplasm" as used herein means a new or abnormal growth of tissue in some part of the body especially as a characteristic of cancer.

The term "neutralizing antibody" or "NAb" refers to an antibody which either is purified from, or is present in, a body fluid (e.g., serum or a mucosal secretion) and which recognizes a specific antigen and inhibits the effect(s) of the antigen in the subject (e.g., a human). As used herein, the antibody can be a single antibody or a plurality of antibodies.

The term "non-neutralizing antibody" or "nnAb" refers to a binding antibody that is not a neutralizing antibody.

"Operably linked." A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "prevent", "preventing" and "prevention" refers to the inhibition of the development or onset of a condition (e.g., a tumor or a condition associated therewith), or the prevention of the recurrence, onset, or development of one or more symptoms of a condition in a subject resulting from the administration of a therapy or the administration of a combination of therapies.

The term "promoter" refers to a polynucleotide sufficient to direct transcription.

The term "prophylactically effective amount" refers to the amount of a composition (e.g., the recombinant MVA vector or pharmaceutical composition) which is sufficient to result in the prevention of the development, recurrence, or onset of a condition or a symptom thereof (e.g., a tumor or a condition or symptom associated therewith or to enhance or improve the prophylactic effect(s) of another therapy.

The term "recombinant" means a polynucleotide of semisynthetic, or synthetic origin that either does not occur in nature or is linked to another polynucleotide in an arrangement not found in nature.

The term "recombinant," with respect to a viral vector, means a vector (e.g., a viral genome that has been manipulated in vitro, e.g., using recombinant nucleic acid techniques to express heterologous viral nucleic acid sequences.

The term "regulatory sequence" "regulatory sequences" refers collectively to promoter sequences, polyadenylation signals, transcription termination sequences, upstream regulatory domains, origins of replication, internal ribosome entry sites ("IRES"), enhancers, and the like, which collectively provide for the transcription and translation of a coding sequence. Not all of these control sequences need always be present so long as the selected gene is capable of being transcribed and translated.

The term "shuttle vector" refers to a genetic vector (e.g., a DNA plasmid) that is useful for transferring genetic material from one host system into another. A shuttle vector can replicate alone (without the presence of any other vector) in at least one host (e.g., E. coli). In the context of MVA vector construction, shuttle vectors are usually DNA plasmids that can be manipulated in E. coli and then introduced into cultured cells infected with MVA vectors, resulting in the generation of new recombinant MVA vectors.

The term "silent mutation" means a change in a nucleotide sequence that does not cause a change in the primary structure of the protein encoded by the nucleotide sequence, e.g., a change from AAA (encoding lysine) to AAG (also encoding lysine).

The term "subject" means any mammal, including but not limited to, humans, domestic and farm animals, and zoo, sports, or pet animals, such as dogs, horses, cats, cows, rats, mice, guinea pigs and the like. Determination of those subjects "at risk" can be made by any objective or subjective determination by a diagnostic test or opinion of a subject or health care provider (e.g., genetic test, enzyme or protein marker, marker history, and the like).

The term "Sudan virus" refers to a virus of species Sudan ebolavirus and has the meaning given to it by the International Committee on Taxonomy of Viruses as documented in (Kuhn, J. H. et al. 2010 Arch Virol 155:2083-2103).

The term "surrogate endpoint" means a clinical measurement other than a measurement of clinical benefit that is used as a substitute for a measurement of clinical benefit.

The term "surrogate marker" means a laboratory measurement or physical sign that is used in a clinical or animal trial as a substitute for a clinically meaningful endpoint that is a direct measure of how a subject feels, functions, or survives and is expected to predict the effect of the therapy (Katz, R., NeuroRx 1:189-195 (2004); New drug, antibiotic, and biological drug product regulations; accelerated approval-FDA. Final rule. Fed Regist 57: 58942-58960, 1992.) The term "surrogate marker for protection" means a surrogate marker that is used in a clinical or animal trial as a substitute for the clinically meaningful endpoint of reduction or prevention of neoplasm growth.

The term "synonymous codon" refers to the use of a codon with a different nucleic acid sequence to encode the same amino acid, e.g., AAA and AAG (both of which encode lysine). Codon optimization changes the codons for a protein to the synonymous codons that are most frequently used by a vector or a host cell.

The term "therapeutically effective amount" means the amount of the composition (e.g., the recombinant MVA vector or pharmaceutical composition) that, when administered to a mammal for treating a neoplasm, is sufficient to effect such treatment for the neoplasm.

The term "treating" or "treat" refer to the eradication or control of a neoplasm, the reduction or amelioration of the progression, severity, and/or duration of a condition or one or more symptoms caused by the neoplasm resulting from the administration of one or more therapies.

The term "vaccine" means material used to provoke an immune response and confer immunity after administration of the material to a subject. Such immunity may include a cellular or humoral immune response that occurs when the subject is exposed to the immunogen after vaccine administration.

The term "vaccine insert" refers to a nucleic acid sequence encoding a heterologous sequence that is operably linked to a promoter for expression when inserted into a recombinant vector. The heterologous sequence may encode a glycoprotein or matrix protein described here.

The term "virus-like particles" or "VLP" refers to a structure which resembles the native virus antigenically and morphologically.

II. Tumor Associated Antigens

The compositions of the present invention are useful for inducing an immune response to a Tumor associated antigen.

In a particular embodiment, the vectors express MUC-1. In one embodiment, the vectors express a hypoglycosylated form of MUC-1. MUC1 is found on nearly all epithelial cells, but it is over expressed in cancer cells, and its associated glycans are shorter than those of non-tumor-associated MUC1 (Gaidzik N et al. 2013, Chem Soc Rev. 42 (10): 4421-42).

The transmembrane glycoprotein Mucin 1 (MUC1) is aberrantly glycosylated and overexpressed in a variety of epithelial cancers, and plays a crucial role in progression of the disease. Tumor-associated MUC1 differs from the MUC1 expressed in normal cells with regard to its biochemical features, cellular distribution, and function. In cancer cells, MUC1 participates in intracellular signal transduction pathways and regulates the expression of its target genes at both the transcriptional and post-transcriptional levels (Nath, S., Trends in Mol Med., Volume 20, Issue 6, p 332-342, June 2014).

A. Immunogenic Fragments of TAA

In various embodiments, immunogenic fragments of TAAs may be expressed by the MVA vectors described herein.

In certain embodiments, immunogenic fragments such as those recited in Table 1 may be expressed by the MVA vectors described herein.

TABLE 1

Immunogenic fragments of tumor associated antigens

| Antigen | Protein Accession # | Fragment | Position (amino acids) |
| --- | --- | --- | --- |
| MUC1 | NP_001191214 | Extracellular Domain | 20-376 |
| MUC1 | NP_001191214 | Intracellular Domain | 407-475 |
| OFA/iLRP | NP_001291217 | Laminin-binding Domains | 166-300 |
| 5T4 | NP_001159864 | Extracellular Domain | 61-345 |
| 5T4 | NP_001159864 | Intracellular Domain | 377-420 |
| CEA | NP_001278413 | Ig Domains | 36-659 |

In one embodiment, the vectors express an immunogenic extracellular domain fragment of MUC1.

In one embodiment, the vectors express an extracellular domain fragment of MUC1 consisting of the sequence AHGVTSAPDTRPAPGSTAPP (SEQ ID NO:1).

In one embodiment, the vectors express an extracellular domain fragment of MUC1 consisting of the sequence AHGVTSAPDNRPALGSTAPP (SEQ ID NO:2).

In one embodiment, the vectors express an extracellular domain fragment of MUC1 consisting of the sequence AHGVTSAPDTRPAPGSTAPPAHGVTSAPDNRPALGSTAPP (SEQ ID NO:3).

In one embodiment, the vectors express an extracellular domain fragment of MUC1 consisting of the sequence AHGVTSAPDTRPAPGSTAPPAHGVTSAPDTRPAPGSTAPPAHGVTSAPDTRPAPGSTAPP AHGVTSAPDTRPAPGSTAPPAHGVTSAPDNRPALGSTAPP (SEQ ID NO:4).

In one embodiment, the vectors express an intracellular domain fragment of MUC1.

In one embodiment, vectors express an extracellular fragment of MUC-1, an intracellular fragment of MUC-1, and a transmembrane domain of a glycoprotein (GP) of Marburg-virus.

In one embodiment, vectors express an extracellular fragment of a TAA, an intracellular fragment of a TAA, and a transmembrane domain of a glycoprotein (GP) of Marburg-virus.

III. Recombinant Viral Vectors

In one aspect, the present invention is a recombinant viral vector comprising one or more nucleic acid sequences encoding tumor associated antigens or immunogenic fragments thereof. In certain embodiments, the recombinant viral vector is a vaccinia viral vector, and more particularly, an MVA vector, comprising one or more nucleic acid sequences encoding tumor associated antigens or immunogenic fragments thereof.

Vaccinia viruses have also been used to engineer viral vectors for recombinant gene expression and for the potential use as recombinant live vaccines (Mackett, M. et al 1982 PNAS USA 79:7415-7419; Smith, G. L. et al. 1984 Biotech Genet Engin Rev 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385). The recombinant vaccinia viruses prepared in this way can be used, on the one hand, as live vaccines for the prophylaxis of infectious diseases, on the other hand, for the preparation of heterologous proteins in eukaryotic cells.

Several such strains of vaccinia virus have been developed to avoid undesired side effects of smallpox vaccination. Thus, a modified vaccinia Ankara (MVA) has been generated by long-term serial passages of the Ankara strain of vaccinia virus (CVA) on chicken embryo fibroblasts (for review see Mayr, A. et al. 1975 Infection 3:6-14; Swiss Patent No. 568,392). The MVA virus is publicly available from American Type Culture Collection as ATCC No.: VR-1508. MVA is distinguished by its great attenuation, as demonstrated by diminished virulence and reduced ability to replicate in primate cells, while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 J Gen Virol 72:1031-1038). The resulting MVA virus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr A. et al. 1978 Zentralbl Bakteriol [B] 167:375-390; Stickl et al. 1974 Dtsch Med Wschr 99:2386-2392). During these studies in over 120,000 humans, including high-risk patients, no side effects were associated with the use of MVA vaccine.

MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. 1992 PNAS USA 89:10847-10851). Additionally, novel vaccinia vector vaccines were established on the basis of MVA having foreign DNA sequences inserted at the site of deletion III within the MVA genome (Sutter, G. et al. 1994 Vaccine 12:1032-1040).

Recombinant MVA vaccinia viruses can be prepared as set out hereinafter. A DNA-construct which contains a DNA-sequence which codes for a foreign polypeptide flanked by MVA DNA sequences adjacent to a predetermined insertion site (e.g. between two conserved essential MVA genes such as I8R/G1L; in restructured and modified deletion III; or at other non-essential sites within the MVA genome) is introduced into cells infected with MVA, to allow homologous recombination. Once the DNA-construct has been introduced into the eukaryotic cell and the foreign DNA has recombined with the viral DNA, it is possible to isolate the desired recombinant vaccinia virus in a manner known per se, preferably with the aid of a marker. The DNA-construct to be inserted can be linear or circular. A plasmid or polymerase chain reaction product is preferred. Such methods of making recombinant MVA vectors are described in PCT publication WO/2006/026667 incorporated by reference herein. The DNA-construct contains sequences flanking the left and the right side of a naturally occurring deletion. The foreign DNA sequence is inserted between the sequences flanking the naturally occurring deletion. For the expression of a DNA sequence or gene, it is necessary for regulatory sequences, which are required for the transcription of the gene, to be present on the DNA. Such regulatory sequences (called promoters) are known to those skilled in the art, and include for example those of the vaccinia 11 kDa gene as are described in EP-A-198,328, and those of the 7.5 kDa gene (EP-A-110,385). The DNA-construct can be introduced into the MVA infected cells by transfection, for example by means of calcium phosphate precipitation (Graham et al. 1973 Virol 52:456-467; Wigler et al. 1979 Cell 16:777-785), by means of electroporation (Neumann et al. 1982 EMBO J. 1:841-845), by microinjection (Graessmann et al. 1983 Meth Enzymol 101:482-492), by means of liposomes (Straubinger et al. 1983 Meth Enzymol 101:512-527), by means of spheroplasts (Schaffher 1980 PNAS USA 77:2163-2167) or by other methods known to those skilled in the art.

The MVA vectors described and tested herein were unexpectedly found to be effective after a single prime or a homologous prime/boost regimen. Other MVA vector designs require a heterologous prime/boost regimen while still other published studies have been unable to induce effective immune responses with MVA vectors. Conversely, the present MVA vector design and methods of manufacture are useful in producing effective MVA vaccine vectors for eliciting effective T-cell and antibody immune responses. Furthermore, the utility of an MVA vaccine vector capable of eliciting effective immune responses and antibody production after a single homologous prime boost is significant for considerations such as use, commercialization and transport of materials especially to affected third world locations.

In one embodiment, the present invention is a recombinant viral vector (e.g., an MVA vector) comprising one or more nucleic acid sequences encoding tumor associated antigens or immunogenic fragments thereof. The viral vector (e.g., an MVA vector) may be constructed using conventional techniques known to one of skill in the art. The one or more heterologous gene inserts encode a polypeptide having desired immunogenicity, i.e., a polypeptide that can induce an immune reaction, cellular immunity and/or humoral immunity, in vivo by administration thereof. The gene region of the viral vector (e.g., an MVA vector) where the gene encoding a polypeptide having immunogenicity is introduced is flanked by regions that are indispensable. In the introduction of a gene encoding a polypeptide having immunogenicity, an appropriate promoter may be operatively linked upstream of the gene encoding a polypeptide having desired immunogenicity.

The one or more nucleic acid sequences encoding tumor associated antigens or immunogenic fragments thereof may be selected from any TAAs. In one embodiment, the one more TAA or immunogenic fragments thereof are selected from the group consisting of MUC1, an extracellular fragment of MUC1, an intracellular fragment of MUC1, Oncofetal Antigen/immature Laminin Receptor Protein (OFA/iLRP), an extracellular fragment of OFA/iLRP, an intracellular fragment of OFA/iLRP, Carcinoembryonic antigen (CEA), an extracellular fragment of CEA, an intracellular fragment of CEA, or a combination thereof. In exemplary embodiments, the gene encodes a polypeptide or protein capable of inducing an immune response in the subject to which it is administered, and more particularly, an immune response capable of providing a protective and/or therapeutic benefit to the subject.

In one embodiment, the nucleic acid sequence encodes MUC1. The heterologous gene inserts are inserted into one or more deletion sites of the vector under the control of promoters compatible with poxvirus expression systems.

In another embodiment, the nucleic acid sequence encodes an immunogenic fragment of MUC1.

In one embodiment, the vectors express an immunogenic extracellular domain fragment of MUC1.

In one embodiment, the vectors express an extracellular domain fragment of MUC1 consisting of the sequence AHGVTSAPDTRPAPGSTAPP (SEQ ID NO:1).

In one embodiment, the vectors express an extracellular domain fragment of MUC1 consisting of the sequence AHGVTSAPDNRPALGSTAPP (SEQ ID NO:2).

In one embodiment, the vectors express an extracellular domain fragment of MUC1 consisting of the sequence AHGVTSAPDTRPAPGSTAPPAHGVTSAPDNRPALG-STAPP (SEQ ID NO:3).

In one embodiment, the vectors express an extracellular domain fragment of MUC1 consisting of the sequence AHGVTSAPDTRPAPGSTAPPAHGVTSAPDTRPAPG-STAPPAHGVTSAPDTRPAPGSTAPP AHGVTSAPDTR-PAPGSTAPPAHGVTSAPDNRPALGSTAPP (SEQ ID NO:4).

In one embodiment, the vectors express an intracellular domain fragment of MUC1.

In one embodiment, the nucleic acid sequence encodes an extracellular fragment of MUC1 and an intracellular fragment of MUC1.

In one embodiment, the nucleic acid sequence encodes a transmembrane domain of the glycoprotein (GP) of Marburgvirus.

In one embodiment, the nucleic acid sequence encodes an immunogenic extracellular domain sequence of MUC1 and a transmembrane domain of the glycoprotein (GP) of Marburgvirus.

In one embodiment, the nucleic acid sequence encodes an immunogenic extracellular domain sequence of MUC1 and a transmembrane domain of the glycoprotein (GP) of Marburgvirus and an intracellular domain sequence of MUC1.

In one embodiment, the nucleic acid sequence encodes an immunogenic extracellular domain sequence of MUC1 comprising a fragment of MUC1 having the sequence AHGVTSAPDTRPAPGSTAPPAHGVTSAPDTRPAPG-STAPPAHGVTSAPDTRPAPGSTAPP AHGVTSAPDTR-PAPGSTAPPAHGVTSAPDNRPALGSTAPP (SEQ ID NO:4) and a transmembrane domain of the glycoprotein (GP) of Marburgvirus and an intracellular domain sequence of MUC1.

In one embodiment, the deletion III site is restructured and modified to remove non-essential flanking sequences.

In exemplary embodiments, the vaccine is constructed to express a TAA for example MUC1, which is inserted between two conserved essential MVA genes (I8R and G1L) using shuttle vector pGeo-MUC1; and to express MUC1, which is inserted into deletion III using shuttle vector pGeo-MUC1. pGeo-MUC1 is constructed with an ampicillin resistance marker, allowing the vector to replicate in bacteria; with two flanking sequences, allowing the vector to recombine with a specific location in the MVA genome; with a green fluorescent protein (GFP) selection marker, allowing the selection of recombinant MVAs; with a sequence homologous to part of Flank 1 of the MVA sequence, enabling removal of the GFP sequence from the MVA vector after insertion of MUC1 into the MVA genome; with a modified H5 (mH5) promoter, which enables transcription of the inserted heterologous gene insert; and with a TAA sequence.

In certain embodiments, the polypeptide, or the nucleic acid sequence encoding the polypeptide, may have a mutation or deletion (e.g., an internal deletion, truncation of the amino- or carboxy-terminus, or a point mutation).

The one or more genes introduced into the recombinant viral vector are under the control of regulatory sequences that direct its expression in a cell.

The nucleic acid material of the viral vector may be encapsulated, e.g., in a lipid membrane or by structural proteins (e.g., capsid proteins), that may include one or more viral polypeptides.

In exemplary embodiments, the present invention is a recombinant viral vector (e.g., a recombinant MVA vector) comprising one or more genes, or one or more polypeptides encoded by the gene or genes, from a TAA.

The nucleic acid sequences of many TAAs are published and are available from a variety of sources, including, e.g., GenBank and PubMed. Exemplary GenBank references including MUC1 include those corresponding to accession numbers NM_001204285.

In certain embodiments, the one or more genes encodes a polypeptide, or fragment thereof, that is substantially identical (e.g., at least 60%, 65%, 70%, 75%, 80%, 85%, 90%, 95%, 98%, 99%, or even 100% identical) to the selected TAA over at least 20, 25, 30, 35, 40, 45, 50, 55, 60, 65, or 70 contiguous residues of the selected TAA or immunogenic fragment thereof that retain immunogenic activity.

In one embodiment, the sequence encoding a TAA or immunogenic fragment thereof is inserted into deletion site I, II, III, IV, V or VI of the MVA vector.

In one embodiment, the sequence encoding a TAA or immunogenic fragment thereof is inserted between I8R and G1L of the MVA vector, or into restructured and modified deletion III of the MVA vector; and a second sequence encoding a TAA or immunogenic fragment thereof is inserted between I8R and G1L of the MVA vector, or into restructured and modified deletion site III of the MVA vector.

In one embodiment, the recombinant vector comprises in a first deletion site, a nucleic acid sequence encoding a TAA or immunogenic fragment thereof operably linked to a promoter compatible with poxvirus expression systems, and in a second deletion site, a nucleic acid sequence encoding a VLP-forming protein operably linked to a promoter compatible with poxvirus expression systems.

In exemplary embodiments, the present invention is a recombinant MVA vector comprising at least one heterologous nucleic acid sequence (e.g., one or more sequences) encoding a TAA or immunogenic fragment thereof which is under the control of regulatory sequences that direct its expression in a cell. The sequence may be, for example, under the control of a promoter selected from the group consisting of Pm2H5, Psyn II, or mH5 promoters.

The recombinant viral vector of the present invention can be used to infect cells of a subject, which, in turn, promotes the translation into a protein product of the one or more heterologous sequence of the viral vector (e.g., a TAA or immunogenic fragment thereof). As discussed further herein, the recombinant viral vector can be administered to a subject so that it infects one or more cells of the subject, which then promotes expression of the one or more viral genes of the viral vector and stimulates an immune response that is therapeutic or protective against a neoplasm.

In one embodiment, the recombinant MVA vaccine expresses proteins that assemble into virus-like particles (VLPs) comprising the TAA or immunogenic fragment thereof. While not wanting to be bound by any particular theory, it is believed that the TAA is provided to elicit a protective immune response and the matrix protein is provided to enable assembly of VLPs and as a target for T cell immune responses, thereby enhancing the protective immune response and providing cross-protection.

In one embodiment, the matrix protein is a Marburg virus matrix protein.

In one embodiment, the matrix protein is an Ebola virus matrix protein.

In one embodiment, the matrix protein is a Sudan virus matrix protein.

In one embodiment, the matrix protein is a human immunodeficiency virus type 1 (HIV-1) matrix protein.

In one embodiment, the matrix protein is a human immunodeficiency virus type 1 (HIV-1) matrix protein encoded by the gag gene.

In one embodiment, the matrix protein is a Lassa virus matrix protein.

In one embodiment, the matrix protein is a Lassa virus Z protein.

In one embodiment, the matrix protein is a fragment of a Lassa virus Z protein.

In one embodiment, the matrix protein is a matrix protein of a virus in the Filoviridae virus family.

In one embodiment, the matrix protein is a matrix protein of a virus in the Retroviridae virus family.

In one embodiment, the matrix protein is a matrix protein of a virus in the Arenaviridae virus family.

In one embodiment, the matrix protein is a matrix protein of a virus in the Flaviviridae virus family.

One or more nucleic acid sequences may be optimized for use in an MVA vector. Optimization includes codon optimization, which employs silent mutations to change selected codons from the native sequences into synonymous codons that are optimally expressed by the host-vector system. Other types of optimization include the use of silent mutations to interrupt homopolymer stretches or transcription terminator motifs. Each of these optimization strategies can improve the stability of the gene, improve the stability of the transcript, or improve the level of protein expression from the sequence. In exemplary embodiments, the number of homopolymer stretches in the TAA sequence will be reduced to stabilize the construct. A silent mutation may be provided for anything similar to a vaccinia termination signal. An extra nucleotide may be added in order to express the transmembrane, rather than the secreted, form of any TAA.

In exemplary embodiments, the sequences are codon optimized for expression in MVA; sequences with runs of ≥5 deoxyguanosines, ≥5 deoxycytidines, ≥5 deoxyadenosines, and ≥5 deoxythymidines are interrupted by silent mutation to minimize loss of expression due to frame shift mutations; and the GP sequence is modified through addition of an extra nucleotide to express the transmembrane, rather than the secreted, form of the protein.

In one embodiment, the present invention provides a vaccine vector composition that is monovalent. As used herein the term monovalent refers to a vaccine vector composition that contains sequences from one TAA.

In another embodiment, the present invention provides a vaccine that is bivalent. As used herein the term bivalent refers to a vaccine vector composition that contains two vectors having sequences from different TAAs.

In another embodiment, the present invention provides a vaccine that is trivalent. As used herein the term trivalent refers to a vaccine vector composition that contains three vectors having sequences from different TAAs.

In another embodiment, the present invention provides a vaccine that is quadrivalent. As used herein the term quadrivalent refers to a vaccine vector composition that contains four vectors having sequences from different TAAs. As used herein, the terms tetravalent and quadrivalent are synonymous.

The present invention also extends to host cells comprising the recombinant viral vector described above, as well as isolated virions prepared from host cells infected with the recombinant viral vector.

In one embodiment, the TAA is overexpressed with an siRNA directed to Core 1 α3galactosyltransferase (T Synthase) or COSMC. COSMC is a molecular chaperone thought to be required for expression of active T-synthase, the only enzyme that galactosylates the Tn antigen (GalNAcα1-Ser/Thr-R) to form core 1 Galβ1-3GalNAcα1-Ser/Thr (T antigen) during mucin type O-glycan biosynthesis (Wang et al. Proc Natl Acad Sci USA. 2010 May 18; 107(20): 9228-9233).

In another embodiment, the TAA is overexpressed with sialiyl transerase 1. Sialyltransferases are key enzymes that regulate the cellular levels of sialic acid-containing molecules.

In particular embodiment, the sialyltransferase is ST6GALNAC1.

In another embodiment, the TAA is overexpressed with sialiyl transerase land an siRNA directed to Core 1 β3galactosyltransferase (T Synthase) or COSMC (T synthase-specific chaperone; C1GALT1C1).

IV. Pharmaceutical Composition

The recombinant viral vectors of the present invention are readily formulated as pharmaceutical compositions for veterinary or human use, either alone or in combination. The pharmaceutical composition may comprise a pharmaceutically acceptable diluent, excipient, carrier, or adjuvant.

In one embodiment, the present invention is a vaccine effective to protect and/or treat a neoplasm comprising a recombinant MVA vector that expresses at least one TAA polypeptide (e.g., a TAA) or an immunogenic fragment thereof. The vaccine composition may comprise one or more additional therapeutic agents.

The pharmaceutical composition may comprise 1, 2, 3, 4 or more than 4 different recombinant MVA vectors.

In one embodiment, the present invention provides a vaccine vector composition that is monovalent. As used herein the term monovalent refers to a vaccine vector composition that contains one TAA sequence.

In another embodiment, the present invention provides a vaccine that is bivalent. As used herein the term bivalent refers to a vaccine vector composition that contains two vectors having sequences from different TAAs.

In another embodiment, the present invention provides a vaccine that is trivalent. As used herein the term trivalent refers to a vaccine vector composition that contains three vectors having sequences from different TAAs.

In another embodiment, the present invention provides a vaccine that is quadrivalent. As used herein the term quadrivalent refers to a vaccine vector composition that contains four vectors having sequences from different TAAs. As used herein, the terms tetravalent and quadrivalent are synonymous.

As used herein, the phrase "pharmaceutically acceptable carrier" encompasses any of the standard pharmaceutical carriers, such as those suitable for parenteral administration, such as, for example, by intramuscular, intraarticular (in the joints), intravenous, intradermal, intraperitoneal, and subcutaneous routes. Examples of such formulations include aqueous and non-aqueous, isotonic sterile injection solutions, which contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. One exemplary pharmaceutically acceptable carrier is physiological saline.

Other physiologically acceptable diluents, excipients, carriers, or adjuvants and their formulations are known to those skilled in the art.

In one embodiment, adjuvants are used as immune response enhancers. In various embodiments, the immune response enhancer is selected from the group consisting of alum-based adjuvants, oil based adjuvants, Specol, RIBI, TiterMax, Montanide ISA50 or Montanide ISA 720, GM-CSF, nonionic block copolymer-based adjuvants, dimethyl dioctadecyl ammoniumbromide (DDA) based adjuvants AS-1, AS-2, Ribi Adjuvant system based adjuvants, QS21, Quil A, SAF (Syntex adjuvant in its microfluidized form (SAF-m), dimethyl-dioctadecyl ammonium bromide (DDA), human complement based adjuvants m. vaccae, ISCOMS, MF-59, SBAS-2, SBAS-4, Enhanzyn®, RC-529, AGPs, MPL-SE, QS7, Escin; Digitonin; and *Gypsophila, Chenopodium quinoa* saponins.

The compositions utilized in the methods described herein can be administered by a route selected from, e.g., parenteral, intramuscular, intraarterial, intravascular, intravenous, intraperitoneal, subcutaneous, dermal, transdermal, ocular, inhalation, buccal, sublingual, perilingual, nasal, topical administration, and oral administration. The preferred method of administration can vary depending on various factors (e.g., the components of the composition being administered and the severity of the condition being treated). Formulations suitable for oral administration may consist of liquid solutions, such as an effective amount of the composition dissolved in a diluent (e.g., water, saline, or PEG-400), capsules, sachets or tablets, each containing a predetermined amount of the vaccine. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen).

For the purposes of this invention, pharmaceutical compositions suitable for delivering a therapeutic or biologically active agent can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, Remington: The Science and Practice of Pharmacy ($21^{st}$ ed.), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

The immunogenicity of the composition (e.g., vaccine) may be significantly improved if the composition of the present invention is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM-Matrix, DC-Chol, DDA, cytokines, and other adjuvants and derivatives thereof.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastrointestinal tract; or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

Formulations suitable for oral administration can consist of (a) liquid solutions, such as an effective amount of the vaccine dissolved in diluents, such as water, saline or PEG 400; (b) capsules, sachets or tablets, each containing a predetermined amount of the vaccine, as liquids, solids, granules or gelatin; (c) suspensions in an appropriate liquid; (d) suitable emulsions; and (e) polysaccharide polymers such as chitins. The vaccine, alone or in combination with other suitable components, may also be made into aerosol formulations to be administered via inhalation, e.g., to the bronchial passageways. Aerosol formulations can be placed into pressurized acceptable propellants, such as dichlorodifluoromethane, propane, nitrogen, and the like.

Suitable formulations for rectal administration include, for example, suppositories, which consist of the vaccine with a suppository base. Suitable suppository bases include natural or synthetic triglycerides or paraffin hydrocarbons. In addition, it is also possible to use gelatin rectal capsules which consist of a combination of the vaccine with a base, including, for example, liquid triglycerides, polyethylene glycols, and paraffin hydrocarbons.

The vaccines of the present invention may also be co-administered with cytokines to further enhance immunogenicity. The cytokines may be administered by methods known to those skilled in the art, e.g., as a nucleic acid molecule in plasmid form or as a protein or fusion protein.

This invention also provides kits comprising the vaccines of the present invention. For example, kits comprising a vaccine and instructions for use are within the scope of this invention.

V. Combination with Checkpoint Inhibitors and Chemotherapy

In one embodiment, the above methods can further involve administering a standard of care therapy to the subject. In embodiments, the standard of care therapy is surgery, radiation, radio frequency, cryogenic, ultranoic ablation, systemic chemotherapy, or a combination thereof.

The vector compositions described herein may be provided as a pharmaceutical composition in combination with other active ingredients. The active agent may be, without limitation, including but not limited to radionuclides, immunomodulators, anti-angiogenic agents, cytokines, chemokines, growth factors, hormones, drugs, prodrugs, enzymes, oligonucleotides, siRNAs, pro-apoptotic agents, photoactive therapeutic agents, cytotoxic agents, chemotherapeutic agents, toxins, other antibodies or antigen binding fragments thereof.

In another embodiment, the pharmaceutical composition includes a TAA-expressing vector described herein and a checkpoint inhibitor to activate CD4+, CD8+ effector T-cells to increase tumor clearance.

In various embodiments, the checkpoint inhibitor is an antibody.

Antibodies are a key component of the adaptive immune response, playing a central role in both recognizing foreign antigens and stimulating an immune response. Many immunotherapeutic regimens involve antibodies. There are a number of FDA-approved antibodies useful as combination therapies. These antibodies may be selected from Alemtuzumab, Atezolizumab, Ipilimumab, Nivolumab, Ofatumumab, Pembrolizumab, or Rituximab.

Monoclonal antibodies that target either PD-1 or PD-L1 can boost the immune response against cancer cells and have shown a great deal of promise in treating certain cancers. Examples of antibodies that target PD-1 include Pembrolizumab and Nivolumab. An example of an antibody that targets PD-L1 is Atezolizumab.

CTLA-4 is another protein on some T cells that acts as a type of "off switch" to keep the immune system in check. Ipilimumab is a monoclonal antibody that attaches to CTLA-4 to block activity and boost an immune response against a neoplasm.

In another embodiment, the immunogenic vector compositions are administered with adjuvant chemotherapy to increase dendritic cell ability to induce T cell proliferation.

In various embodiments, the vector compositions are administered, before, after or at the same time as chemotherapy.

In certain embodiments, the composition of the present invention is able to reduce the need of a subject having a tumor or a cancer to receive chemotherapeutic or radiation treatment. In other embodiments, the composition is able to reduce the severity of side effects associated with radiation or chemotherapy in a subject having a tumor or cancer.

The pharmaceutical compositions of the present invention can be administered alone or in combination with other types of cancer treatment strategies (e.g., radiation therapy, chemotherapy, hormonal therapy, immunotherapy and antitumor agents as described herein.

Suitable chemotherapeutic agents useful with these methods include sorafenb, regorafenib, imatinib, eribulin, gemcitabine, capecitabine, pazopani, lapatinib, dabrafenib, sutinib malate, crizotinib, everolimus, torisirolimus, sirolimus, axitinib, gefitinib, anastrole, bicalutamide, fulvestrant, ralitrexed, pemetrexed, goserilin acetate, erlotininb, vemurafenib, visiodegib, tamoxifen citrate, paclitaxel, docetaxel, cabazitaxel, oxaliplatin, ziv-aflibercept, bevacizumab, trastuzumab, pertuzumab, pantiumumab, taxane, bleomycin, melphalen, plumbagin, camptosar, mitomycin-C, mitoxantrone, SMANCS, doxorubicin, pegylated doxorubicin, Folfori, 5-fluorouracil, temozolomide, pasireotide, tegafur, gimeracil, oteraci, itraconazole, bortezomib, lenalidomide, irintotecan, epirubicin, and romidepsin. Preferred chemotherapeutic agents are Carboplatin, Fluorouracil, Vinblastine, Gemcitabine, Cyclophosphamide, Doxorubicin, Methotrexate, Paclitaxel, Topotecan, Etoposide, Methotrexate, Sorafenib, Irinotecan, and Tarceva.

Generic names of cancer chemotherapeutic drugs that have been typically used in cancer patients include: doxorubicin, epirubicin; 5-fluorouracil, paclitaxel, docetaxel, cisplatin, bleomycin, melphalen, plumbagin, irinotecan, mitomycin-C, and mitoxantrone. By way of example, some other cancer chemotherapeutic drugs that may be used and may be in stages of clinical trials include: resminostat, tasquinimod, refametinib, lapatinib, Tyverb, Arenegyr, pasireotide, Signifor, ticilimumab, tremelimumab, lansoprazole, PrevOnco, ABT-869, linifanib, tivantinib, Tarceva, erlotinib, Stivarga, regorafenib, fluoro-sorafenib, brivanib, liposomal doxorubicin, lenvatinib, ramucirumab, peretinoin, Ruchiko, muparfostat, Teysuno, tegafur, gimeracil, oteracil, and orantinib.

Manufacturer brand names for some cancer drugs that may be used in the present invention include: NEXAVAR (sorafenb), STIVARGA (regorafenib), AFFINITOR (everolimus), GLEEVEC (imatinib), HALAVEN (eribulin), ALIMTA (pemetrexed), GEMZAR (gemcitabine), VOTRIENT (pazopanib), TYKERB (lapatinib), TAFINIAR (dabrafenib), SUTENT (sutinib malate), XALKORI (crizotinib), TORISEL (torisirolimus), INLYTA (axitinib), IRESSA (gefitinib), ARIMEDEX (anastrole), CASODEX (bicalutamide), FASLODEX (fulvestrant), TOMUDEX (ralitrexed), ZOLADEX (goserilin acetate), TARCEVA (erlotininb), XELODA (capecitabine), ZELBROF (vemurafenib), ERIVEDGE (visiodegib), PERJETA (pertuzumab), HERCEPTIN (trastuzumab), TAXOTERE (docetaxel), JEVTANA (cabazitaxel), ELOXATIN (oxaliplatin), ZALTRAP (ziv-aflibercept), AVASTIN (bevacizumab) Nolvadex, Istubal, and VALODEX (tamoxifen citrate), TEMODAR (temozolomide), SIGNIFOR (pasireotide), VECTIBIX (pantiumumab), ADRIAMYCIN (doxorubicin), DOXIL (pegylated doxorubicin), ABRAXANE (Paclitaxel), TEYSUNO (tegafur, gimeracil, oteracil), BORTEZOMIB (Velcade) and with lenalidomide, ISTODAX (romidepsin).

It is believed that one way that Doxorubicin (ADRIAMYCIN) and DOXIL (pegylated doxorubicin in liposomes) can act to kill cancer cells is by intercalating DNA. It is also thought that doxorubicin can become a nitroxide free radical and/or thereby increase cellular levels of free radicals in cancer cells and thereby trigger cellular damage and programmed death. There are potentially serious adverse systemic effects of doxorubicin such as heart damage which limit its use.

5-Fluorouracil (5-FU, Efudex) is a pyrimidine analog which is used in the treatment of cancer. It is a suicide inhibitor and works through irreversible inhibition of thymidylate synthase. Like many anti-cancer drugs, 5-FU's effects are felt system wide but fall most heavily upon rapidly dividing cells that make more frequent use of their nucleotide synthesis machinery, such as cancer cells. 5-FU kills non-cancer cells in parts of the body that are rapidly dividing, for example, the cells lining the digestive tract. Folfori is a treatment with 5-FU, Camptosar, and Irinotecan (leucovorin). The 5-FU incorporates into the DNA molecule and stops synthesis and Camptosar is a topoisomerase inhibitor, which prevents DNA from uncoiling and duplicating. Irinotecan (folinic acid, leucovorin) is a vitamin B derivative used as a "rescue" drug for high doses of the drug methotrexate and that modulates/potentiates/reduces the side effects of the 5-FU (fluorouracil). Mitomycin C is a potent DNA cross-linker. Prolonged use may result in permanent bone-marrow damage. It may also cause lung fibrosis and renal damage.

Taxanes agents include paclitaxel (Taxol) and docetaxel (Taxotere). Taxanes disrupt cell microtubule function. Microtubules are essential to cell division. Taxanes stabilize GDP-bound tubulin in the microtubule, thereby inhibiting the process of cell division. Cancer cells can no longer divide. However, taxanes may inhibit cell division of non-cancer cells as well.

Cisplatin(s) which includes carboplatin and oxaliplatin are organic platinum complexes which react in vivo, binding to and causing crosslinking of DNA. The cross-linked DNA triggers apoptosis (programmed cell death) of the cancer cells. However, cisplatins can also trigger apoptosis of non-cancer cells.

Bleomycin induces DNA strand breaks. Some studies suggest bleomycin also inhibits incorporation of thymidine into DNA strands. Bleomycin will also kill non-cancer cells. Melphalen (Alkeran) is a nitrogen mustard alkylating agents which adds an alkyl group to the guanine base of DNA. Major adverse effects of mephalen include vomiting, oral ulceration, and bone marrow suppression.

Plumbagin has been shown to induce cell cycle arrest and apoptosis in numerous cancer cell lines. It triggers autophagy via inhibition of the Akt/mTOR pathway. It induces G2/M cell cycle arrest and apoptosis through JNK-dependent p53 Ser15 phosphorylation. It promotes autophagic cell death. It inhibits Akt/mTOR signaling. It induces intracellular ROS generation in a PI 5-kinase-dependent manner. To non-cancer cells plumbagin is a toxin, a genotoxin, and a mutagen.

A chemotherapeutic agent may be selected based upon its specificity and potency of inhibition of a cellular pathway target to which cancer cells in the patient may be susceptible. In practicing the invention, the chemotherapeutic agent may be selected by its ability to inhibit a cellular pathway target selected from the group consisting of mTORC, RAF kinase, MEK kinase, Phosphoinositol kinase 3, Fibroblast growth factor receptor, multiple tyrosine kinase, Human epidermal growth factor receptor, vascular endothelial growth factor, other angiogenesis, heat shock protein; Smo (smooth) receptor, FMS-like tyrosine kinase 3 receptor, Apoptosis protein inhibitor, cyclin dependent kinases, deacetylase, ALK tyrosine kinase receptor, serine/threonine-protein kinase Pim-1, Porcupine acyltransferase, hedgehog pathway, protein kinase C, mDM2, Glypciin3, ChK1, Hepatocyte growth factor MET receptor, Epidermal growth factor domain-like 7, Notch pathway, Src-family kinase, DNA methyltransferase, DNA intercalators, Thymidine synthase, Microtubule function disruptor, DNA cross-linkers, DNA strand breakers, DNA alkylators, JNK-dependent p53 Ser15 phosphorylation inducer, DNA topoisomerase inhibitors, Bcl-2, and free radical generators.

In one embodiment, the vector compositions are administered, before, after or at the same time as epigenetic modulators.

In one embodiment, the vector compositions are administered, before, after or at the same time as an epigenetic modulator selected from the group consisting of inhibitors of DNA methyltransferases, inhibitors of histone methyltransferases, inhibitors of histone acetyltransferases, inhibitors of histone deacetylases, and inhibitors of lysine demethylases.

In one embodiment, the vector compositions are administered, before, after or at the same time as an inhibitor of DNA methyltransferases.

In one embodiment, the vector compositions are administered, before, after or at the same time as an inhibitor of histone deacetylases.

VI. Method of Use

The compositions of the invention can be used as vaccines for inducing an immune response to a TAA.

In exemplary embodiments, the present invention provides a method of inducing an immune response to a TAA in a subject in need thereof, said method comprising administering a recombinant viral vector that encodes at least one TAA or immunogenic fragment thereof. to the subject in an effective amount to generate and immune response to the TAA. The result of the method is that the subject is partially or completely immunized against the TAA.

In one embodiment, invention provides methods for activating an immune response in a subject using the compositions described herein. In some embodiments, the invention provides methods for promoting an immune response in a subject using a composition described herein. In some embodiments, the invention provides methods for increasing an immune response in a subject using a composition described herein. In some embodiments, the invention provides methods for enhancing an immune response in a subject using a composition described herein.

In exemplary embodiments, the present invention provides a method of treating, reducing, preventing or delaying the growth of a neoplasm in a subject in need thereof, said method comprising administering the composition of the present invention to the subject in a therapeutically effective amount. The result of treatment is a subject that has an improved therapeutic profile for a disease associated with the neoplasm.

In exemplary embodiments, the present invention provides a method of treating, cancer in a subject in need thereof, said method comprising administering the composition of the present invention to the subject in a therapeutically effective amount. The result of treatment is a subject that has an improved therapeutic profile for a cancer.

In one embodiment the methods may reduce the growth of the one or more tumors, shrink the one or more tumors, or eradicate the one or more tumors. For example, the tumor mass does not increase. In certain embodiments, the tumor shrinks by 10%, 25%, 50%, 75%, 85%, 90%, 95%, or 99% or more (or any number therebetween) as compared to its original mass. In certain embodiments, the shrinkage is such that an inoperable tumor is sufficient to permit resection if desired. The concept of substantial shrinkage may also be referred to as "regression," which refers to a diminution of a bodily growth, such as a tumor. Such a diminution may be determined by a reduction in measured parameters such as, but not limited to, diameter, mass (i.e., weight), or volume. This diminution by no means indicates that the size is completely reduced, only that a measured parameter is quantitatively less than a previous determination.

In one embodiment, the methods may prevent tumor metastasis.

In exemplary embodiments, the present invention provides a method of treating a proliferative disorder in a subject in need thereof, said method comprising administering the composition of the present invention to the subject in a therapeutically effective amount. As used herein, the term "proliferative disorder" refers to a disorder wherein the growth of a population of cells exceeds, and is uncoordinated with, that of the surrounding cells. In certain instances, a proliferative disorder leads to the formation of a tumor. In some embodiments, the tumor is benign, pre-malignant, or malignant. In other embodiments, the proliferative disorder is an autoimmune diseases, vascular occlusion, restenosis, atherosclerosis, or inflammatory bowel disease. In one embodiment, the autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus), systemic lupus erythematosus (SLE), chronic polyarthritis, Basedow's disease, autoimmune forms of chronic hepatitis, colitis ulcerosa, allergy type I diseases, allergy type II diseases, allergy type III diseases, allergy type IV diseases, fibromyalgia, hair loss, Bechterew's disease, Crohn's disease, Myasthenia gravis, neuroclermitis, Polymyalgia rheumatica, progressive systemic sclerosis (PSS), psoriasis, Reiter's syndrome, rheumatic arthritis, psoriasis, vasculitis, etc, or type II diabetes.

In one embodiment, the immune response is a humoral immune response, a cellular immune response or a combination thereof.

In a particular embodiment, the immune response comprises production of binding antibodies against the TAA.

In a particular embodiment, the immune response comprises production of neutralizing antibodies against the TAA.

In a particular embodiment, the immune response comprises production of non-neutralizing antibodies against the TAA.

In a particular embodiment, the immune response comprises production of a cell-mediated immune response against the TAA.

In a particular embodiment, the immune response comprises production of neutralizing and non-neutralizing antibodies against the TAA.

In a particular embodiment, the immune response comprises production of neutralizing antibodies and cell-mediated immunity against the TAA.

In a particular embodiment, the immune response comprises production of non-neutralizing antibodies and cell-mediated immunity against the TAA.

In a particular embodiment, the immune response comprises production of neutralizing antibodies, non-neutralizing antibodies, and cell-mediated immunity against the TAA.

In certain embodiments, the compositions of the invention can be used as vaccines for treating a subject at risk of developing a neoplasm, or a subject already having a neoplasm. The recombinant viral vector comprises genes or sequences encoding TAAs, viral proteins to promote assembly of virus-like particles (VLPs) or additional enzymes to facilitate expression and glycosylation of the TAA.

Typically the vaccines will be in an admixture and administered simultaneously, but may also be administered separately.

A subject to be treated according to the methods described herein may be one who has been diagnosed by a medical practitioner as having such a condition. (e.g. a subject having a neoplasm). Diagnosis may be performed by any suitable means. One skilled in the art will understand that a subject to be treated according to the present invention may have been identified using standard tests or may have been identified, without examination, as one at high risk due to the presence of one or more risk factors.

Prophylactic treatment may be administered, for example, to a subject not yet having a neoplasm but who is susceptible to, or otherwise at risk of developing a neoplasm.

Therapeutic treatment may be administered, for example, to a subject already a neoplasm in order to improve or stabilize the subject's condition. The result is an improved therapeutic profile. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique.

For example, depending upon the type of cancer, an improved therapeutic profile may be selected from alleviation of one or more symptoms of the cancer, diminishment of extent of disease, stabilized (i.e., not worsening) state of disease, delay or slowing of disease progression, amelioration or palliation of the disease state, remission (whether partial or total), whether detectable or undetectable, tumor regression, inhibition of tumor growth, inhibition of tumor metastasis, reduction in cancer cell number, inhibition of cancer cell infiltration into peripheral organs, improved time to disease progression (TTP), improved response rate (RR), prolonged overall survival (OS), prolonged time-to-next-treatment (TNTT), or prolonged time from first progression to next treatment, or a combination of two or more of the foregoing.

In other embodiments, treatment may result in amelioration of one or more symptoms of a disease associated with a neoplasm (e.g. cancer). According to this embodiment, confirmation of treatment can be assessed by detecting an improvement in or the absence of symptoms.

In one embodiment, the present invention is a method of inducing an immune response in a subject (e.g., a human) by administering to the subject a recombinant viral vector that encodes at least one TAA or immunogenic fragment thereof. The immune response may be a cellular immune response or a humoral immune response, or a combination thereof.

The composition may be administered, e.g., by injection (e.g., intramuscular, intraarterial, intravascular, intravenous, intraperitoneal, or subcutaneous).

It will be appreciated that more than one route of administering the vaccines of the present invention may be employed either simultaneously or sequentially (e.g., boosting). In addition, the vaccines of the present invention may be employed in combination with traditional immunization approaches such as employing protein antigens, vaccinia virus and inactivated virus, as vaccines. Thus, in one embodiment, the vaccines of the present invention are administered to a subject (the subject is "primed" with a vaccine of the present invention) and then a traditional vaccine is administered (the subject is "boosted" with a traditional vaccine). In another embodiment, a traditional vaccine is first administered to the subject followed by administration of a vaccine of the present invention. In yet another embodiment, a traditional vaccine and a vaccine of the present invention are co-administered.

While not to be bound by any specific mechanism, it is believed that upon inoculation with a pharmaceutical composition as described herein, the immune system of the host responds to the vaccine by producing antibodies, both secretory and serum, specific for one or more TAA or immunogenic fragments thereof; and by producing a cell-mediated immune response specific for one or more TAA or immunogenic fragments thereof. As a result of the vaccination, the host becomes at least partially or completely immune to one or more TAA or immunogenic fragments thereof, or resistant to developing moderate or severe diseases caused by neoplasm.

In one aspect, methods are provided to alleviate, reduce the severity of, or reduce the occurrence of, one or more of the symptoms associated with a neoplasm comprising administering an effective amount of a pharmaceutical composition comprising a recombinant MVA viral vector that comprises TAA and matrix protein sequences optionally co-expressing sequences that facilitate expression of and desired glycosylation the TAA.

In another aspect, the invention provides methods of providing anti-TAA immunity comprising administering an effective amount of a pharmaceutical composition comprising a recombinant MVA vaccine expressing TAA and a viral matrix protein to permit the formation of VLPs.

It will also be appreciated that single or multiple administrations of the vaccine compositions of the present invention may be carried out. For example, subjects who are at particularly high risk of developing a neoplasm may require multiple immunizations to establish and/or maintain protective immune responses. Levels of induced immunity can be monitored by measuring amounts of binding and neutralizing secretory and serum antibodies as well as levels of T cells, and dosages adjusted or vaccinations repeated as necessary to maintain desired levels of protection.

In one embodiment, administration is repeated at least twice, at least 3 times, at least 4 times, at least 5 times, at least 6 times, at least 7 times, at least 8 times, or more than 8 times.

In one embodiment, administration is repeated twice.

In one embodiment, about 2-8, about 4-8, or about 6-8 administrations are provided.

In one embodiment, about 1-4-week, 2-4 week, 3-4 week, 1 week, 2 week, 3 week, 4 week or more than 4 week intervals are provided between administrations.

In one specific embodiment, a 4-week interval is used between 2 administrations.

In one embodiment, the invention provides a method of monitoring treatment progress. In exemplary embodiments, the monitoring is focused on biological activity, immune response and/or clinical response.

In one embodiment, the biological activity is a T-cell immune response, regulatory T-cell activity, molecule response (MRD), cytogenic response or conventional tumor response for example, in both the adjuvant or advanced disease setting.

In one embodiment, immune response is monitored for example, by an immunse assay such as a cytotoxicity assay, an intracellular cytokine assay, a tetramer assay or an ELISPOT assay.

In one embodiment, clinical response is monitored for example by outcome using established definitions such as response (tumor regression), progression-free, recurrence-free, or overall survival.

In one embodiment, the method includes the step of determining a level of diagnostic marker marker (e.g., any target delineated herein modulated by a compound herein, a protein or indicator thereof, etc.) or diagnostic measurement (e.g., screen, assay) in a subject having received a therapeutic amount of a compound herein sufficient to treat the disease or symptoms thereof. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to this invention; this pre-treatment level of marker can then be compared to the level of marker in the subject after the treatment commences, to determine the efficacy of the treatment.

In one embodiment, upon improvement of a subject's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

A. Dosage

The vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $5.0 \times 10^6$ $TCID_{50}$ to about $5.0 \times 10^9$ $TCID_{50}$. The dosage may also depend, without limitation, on the route of administration, the patient's state of health and weight, and the nature of the formulation.

The pharmaceutical compositions of the invention are administered in such an amount as will be therapeutically effective, immunogenic, and/or protective against a neoplasm that expresses a TAA. The dosage administered depends on the subject to be treated (e.g., the manner of administration and the age, body weight, capacity of the immune system, and general health of the subject being treated). The composition is administered in an amount to provide a sufficient level of expression that elicits an immune response without undue adverse physiological effects. Preferably, the composition of the invention is a heterologous viral vector that includes one or TAAs or immunogenic fragments thereof and large matrix protein; and is administered at a dosage of, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$ pfu, more preferably between $1.0 \times 10^6$ and $1.0 \times 10^{10}$ $TCID_{50}$ pfu, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). A physician or researcher can decide the appropriate amount and dosage regimen.

The composition of the method may include, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$ pfu, more preferably between $1.0 \times 10^6$ and $1.0 \times 10^{10}$ $TCID_{50}$ pfu, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). The method may include, e.g., administering the composition to the subject two or more times.

The term "effective amount" is meant the amount of a composition administered to improve, inhibit, or ameliorate a condition of a subject, or a symptom of a disorder, in a clinically relevant manner (e.g., improve, inhibit, or ameliorate disease associated with a neoplasm (e.g. cancer) or provide an effective immune response to a neoplasm). Any improvement in the subject is considered sufficient to achieve treatment. Preferably, an amount sufficient to treat is an amount that prevents the occurrence or one or more symptoms of disease associated with a neoplasm or is an amount that reduces the severity of, or the length of time during which a subject suffers from, one or more symptoms of disease associated with a neoplasm (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of the pharmaceutical composition used to practice the methods described herein (e.g., the treatment of disease associated with a neoplasm) varies depending upon the manner of administration and the age, body weight, and general health of the subject being treated.

It is important to note that the value of the present invention may never be demonstrated in terms of actual clinical benefit. Instead, it is likely that the value of the invention will be demonstrated in terms of success against a surrogate marker for protection. For an indication such as disease associated with a neoplasm, in which it is impractical or unethical to attempt to measure clinical benefit of an intervention, the FDA's Accelerated Approval process allows approval of a new vaccine based on efficacy against a surrogate endpoint. Therefore, the value of the invention may lie in its ability to induce an immune response that constitutes a surrogate marker for protection.

Similarly, FDA may allow approval of vaccines against TAAs based on its Animal Rule. In this case, approval is achieved based on efficacy in animals.

The composition of the method may include, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$ pfu, more preferably between $1.0 \times 10^6$ and $1.0 \times 10^{10}$ $TCID_{50}$ pfu, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). The method may include, e.g., administering the composition two or more times.

In some instances it may be desirable to combine the TAA vaccines of the present invention with vaccines which induce protective responses to other agents, particularly other TAAs. For example, the vaccine compositions of the present invention can be administered simultaneously, separately or sequentially with other genetic immunization vaccines such as those for influenza (Ulmer, J. B. et al., Science 259:1745-1749 (1993); Raz, E. et al., PNAS (USA) 91:9519-9523 (1994)), malaria (Doolan, D. L. et al., J. Exp. Med. 183:1739-1746 (1996); Sedegah, M. et al., PNAS (USA) 91:9866-9870 (1994)), and tuberculosis (Tascon, R. C. et al., Nat. Med. 2:888-892 (1996)).

B. Indications

In specific embodiments, the immunogenic vectors useful in the present methods may be administered to a subject with a neoplasm or a subject diagnosed with prostate, breast, lung, liver, endometrial, bladder, colon or cervical carcinoma; adenocarcinoma; melanoma; lymphoma; glioma; or sarcomas such as soft tissue and bone sarcomas.

In a further embodiment the invention is directed to the vectors of the invention for the treatment or prevention of cancer, including, but not limited to, neoplasms, tumors, metastases, or any disease or disorder characterized by uncontrolled cell growth, and particularly multidrug resistant forms thereof. The cancer can be a multifocal tumor. Examples of types of cancer and proliferative disorders to be treated with the therapeutics of the invention include, but are not limited to, leukemia (e.g. myeloblastic, promyelocytic, myelomonocytic, monocytic, erythroleukemia, chronic myelocytic (granulocytic) leukemia, and chronic lymphocytic leukemia), lymphoma (e.g. Hodgkin's disease and non-Hodgkin's disease), fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilms' tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia. In a particular embodiment, therapeutic compounds of the invention are administered to patients having prostate cancer (e.g., prostatitis, benign prostatic hypertrophy, benign prostatic hyperplasia (BPH), prostatic paraganglioma, prostate adenocarcinoma, prostatic intraepithelial neoplasia, prostato-rectal fistulas, and atypical prostatic stromal lesions). In an especially preferred embodiment the medicaments of the present invention are used for the treatment of cancer, glioma, liver carcinoma and/or colon carcinoma. The treatment and/or prevention of cancer includes, but is not limited to, alleviating symptoms associated with cancer, the inhibition of the progression of cancer, the promotion of the regression of cancer, and the promotion of the immune response.

As used herein, the term neoplasm refers to an abnormal growth of tissue. A neoplasm may be benign or malignant. Generally, a malignant neoplasm is referred to as a cancer. Cancers differ from benign neoplasms in the ability of malignant cells to invade other tissues, either by direct growth into adjacent tissue through invasion or by implantation into distant sites by metastasis (i.e., transport through the blood or lymphatic system). The methods of the present invention are suitable for the treatment of benign and malignant neoplasms (cancer).

As defined herein a superficial neoplasm is one located on the outer surface of the body that has confined itself and not spread to surrounding tissues or other parts of the body. An internal neoplasms located on an internal organ or other internal part of the body. An invasive neoplasm is a neoplasm that has started to break through normal tissue barriers and invade surrounding areas, e.g., an invasive breast cancer that has spread beyond the ducts and lobules.

A non-exclusive list of the types of neoplasms contemplated for treatment by the method disclosed herein includes the following categories: (a) abdominal neoplasms including peritonealneoplasms and retroperitoneal neoplasms; (b) bone neoplasms including femoral neoplasms, skull neoplasms, jaw neoplasms, manibular neoplasms, maxillary neoplasms, palatal neoplasms, nose neoplasms, orbital neoplasms, skull base neoplasms, and spinal neoplasms; c) breast neoplasms including male breast neoplasms, breast ductal carcinoma, and phyllodes tumor; (d) digestive system neoplasms including biliary tract neoplasms, bile duct neoplasms, common bile duct neoplasms, gall bladder neoplasms, gastrointestinal neoplasms, esophegeal neoplasms, intestinal neoplasms, cecal neoplasms, appendiceal neoplasms, colorectal neoplasms, colorectal adenomatous polyposis coli, colorectal Gardner Syndrome, colonic neoplasms, colonic adenomatous polyposis coli, colonic Gardner Syndrome, sigmoid neoplasms, hereditary nonpolyposis colorectal neoplasms, rectal neoplasms, anus neoplasms, duodenal neoplasms, ileal neoplasms, jejunal neoplasms, stomach neoplasms, liver neoplasms, liver cell adenoma, hepatocellular carcinoma, pancreatic neoplasms, islet cell adenoma, insulinoma, islet cell carcinoma, gastrinoma, glucagonoma, somatostatinoma, vipoma, pancreatic ductal carcinoma, and peritoneal neoplasms; (e) endocrine gland neoplasms including adrenal gland neoplasms, adrenal cortex neoplasms, adrenocortical adenoma, adrenocortical carcinoma, multiple endocrine neoplasia, multiple endocrine neoplasia type 1, multiple endocrine neoplasia type 2a, multiple endocrine neoplasia type 2b, ovarian neoplasms, granulosa cell tumor, luteoma, Meigs' Syndrome, ovarian Sertoli-Leydig cell tumor, thecoma, pancreatic neoplasms, paraneoplastic endocrine syndromes, parathyroid neoplasms, pituitary neoplasms, Nelson Syndrome, testicular neoplasms, testicular Sertoli-Leydig cell tumor, and thyroid neoplasms (f) eye neoplasms including conjunctival neoplasms, orbital neoplasms, retinal neoplasms, retinoblastoma, uveal neoplasms, choroid neoplasms, and iris neoplasms; (g) brain, head and neck neoplasms including esophageal neoplasms, facial neoplasms, eyelid neoplasms, mouth neoplasms, gingival neoplasms, oral leukoplakia, hairy leukoplakia, lip neoplasms, palatal neoplasms, salivary gland neoplasms, parotid neoplasms, sublingual gland neoplasms, submandibular gland neoplasms, tongue neoplasms, otorhinolaryngologic neoplasms, ear neoplasms, laryngeal neoplasms, nose neoplasms, paranasal sinus neoplasms, maxillary sinus neoplasms, pharyngeal neoplasms, hypopharyngeal neoplasms, nasopharyngeal neoplasms, nasopharyngeal neoplasms, oropharyngeal neoplasms, tonsillar neoplasms, parathyroid neoplasms, thyroid neoplasms, and tracheal neoplasms; (h) hematologic neoplasms including bone marrow neoplasms; (i) nervous system neoplasms including central nervous system neoplasms, brain neoplasms, cerebral ventricle neoplasms, choroid plexus neoplasms, choroid plexus papilloma, infratentorial neoplasms, brain stem neoplasms, cerebellar neoplasms, neurocytoma, pinealoma, supratentorial neoplasms, hypothalamic neoplasms, pituitary neoplasms, Nelson Syndrome, cranial nerve neoplasms, optic nerve neoplasms, optic nerve glioma, acoustic neuroma, neurofibromatosis 2, nervous system paraneoplastic syndromes, Lambert-Eaton myasthenic syndrome, limbic encephalitis, transverse myelitis, paraneoplastic cerebellar degeneration, paraneoplastic polyneuropathy, peripheral nervous system neoplasms, cranial nerve neoplasms, acoustic neuroma, and optic nerve neoplasms; (j) pelvic neoplasms; (k) skin neoplasms including acanthoma, sebaceous gland neoplasms, sweat gland neoplasms and basal cell carcinoma; (l) soft tissue neoplasms including muscle neoplasms and vascular neoplasms; (m) splenic neoplasms; (n) thoracic neoplasms including heart neoplasms, mediastinal neoplasms, respiratory tract neoplasms, bronchial neoplasms, lung neoplasms, bronchogenic carcinoma, non-small-cell lung carcinoma, pulmonary coin lesion, Pancoasts's Syndrome, pulmonary blastoma, pulmonary sclerosing hemangioma, pleural neoplasms, malignant pleural effusion, tracheal neoplasms, thymus neoplasms, and thymoma; (o) urogenital neoplasms including female genital neoplasms, fallopian tube neoplasms, uterine neoplasms, cervix neoplasms, endometrial neoplasms, endometrioid carcinoma, endometrial stromal tumors, endometrial stromal sarcoma, vaginal neoplasms, vulvar neoplasms, male genital neoplasms, penile neoplasms, prostatic neoplasms, testicular neoplasms, urologic neoplasms, bladder neoplasms, kidney neoplasms, renal cell carcinoma, nephroblastoma, Denys-Drash Syndrome, WAGR Syndrome, mesoblastic nephroma, ureteral neoplasms and urethral neoplasms; (p) and additional cancers including renal carcinoma, lung cancer, melanoma, leukemia, Barrett's esophagus, metaplasia pre-cancer cells.

In one embodiment, the immune response stimulating vectors described herein express MUC1 or an immunogenic fragment thereof and are particularly useful for treating Adenocarcinomas (breast, colorectal, pancreatic, other), Carcinoid tumor, Chordoma, Choriocarcinoma, Desmoplastic small round cell tumor (DSRCT), Epithelioid sarcoma, Follicular dendritic cell sarcoma, interdigitating dendritic cell/reticulum cell sarcoma, Lung: type II pneumocyte lesions (type II cell hyperplasia, dysplastic type II cells, apical alveolar hyperplasia), Anaplastic large-cell lymphoma, diffuse large B cell lymphoma (variable), plasmablastic lymphoma, primary effusion lymphoma, Epithelioid mesotheliomas, Myeloma, Plasmacytomas, Perineurioma, Renal cell carcinoma, Synovial sarcoma (epithelial areas), Thymic carcinoma (often), Meningioma or Paget's disease.

C. Administration

As used herein, the term "administering" refers to a method of giving a dosage of a pharmaceutical composition of the invention to a subject. The compositions utilized in the methods described herein can be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, intraarterial, intravascular, and intramuscular administration. The preferred method of administration can vary depending on various factors (e.g., the components of the composition being administered and the severity of the condition being treated).

Administration of the pharmaceutical compositions (e.g., vaccines) of the present invention can be by any of the routes known to one of skill in the art. Administration may be by, e.g., intramuscular injection. The compositions utilized in the methods described herein can also be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. The preferred method of administration can vary depending on various factors, e.g., the components of the composition being administered and the severity of the condition being treated.

In addition, single or multiple administrations of the compositions of the present invention may be given to a subject. For example, subjects who are particularly susceptible to developing a neoplasm may require multiple treatments to establish and/or maintain protection against the neoplasm. Levels of induced immunity provided by the pharmaceutical compositions described herein can be monitored by, e.g., measuring amounts of neutralizing secretory and serum antibodies. The dosages may then be adjusted or repeated as necessary to maintain desired levels of protection against development of a neoplasm or to reduce growth of a neoplasm.

Increased vaccination efficacy can be obtained by timing the administration of the vector. Any of the priming and boosting compositions described above are suitable for use with the methods described here.

In one embodiment, MVA vectors are used for both priming and boosting purposes. Such protocols include but are not limited to MM, MMM, and MMMM.

In some embodiments, one, two, three, four, five, six, seven, eight, nine, ten or more than ten MVA boosts are administered.

Vectors can be administered alone (i.e., a plasmid can be administered on one or several occasions with or without an alternative type of vaccine formulation (e.g., with or without administration of protein or another type of vector, such as a viral vector)) and, optionally, with an adjuvant or in conjunction with (e.g., prior to) an alternative booster immunization (e.g., a live-vectored vaccine such as a recombinant modified vaccinia Ankara vector (MVA)) comprising an insert that may be distinct from that of the "prime" portion of the immunization or may be a related vaccine insert(s). For example, GM-CSF or other adjuvants known to those of skill in the art. The adjuvant can be a "genetic adjuvant" (i.e., a protein delivered by way of a DNA sequence).

In exemplary embodiments, the present invention is an immunization method comprising (i) administering a priming composition comprising a DNA plasmid comprising one or more sequences encoding a TAA or immunogenic fragment thereof; (ii) administering a first dose of a boosting composition comprising a modified vaccinia Ankara viral vector comprising one or more genes encoding a TAA or immunogenic fragment thereof; and (iii) administering a second dose of a boosting composition between about 12 and 20 weeks after the first dose, more particularly between about 14 and about 18 weeks after the first dose, even more particularly, about 16 weeks after the first dose.

In a particular embodiment, the TAA are the same in step (i)-(iii). Optionally, the method further comprises one or more additional steps, including, for example, the administration of one or more additional doses of the priming composition or a different priming composition (i.e., a second priming composition) and/or one or more additional doses of the boosting composition or a different boosting composition (i.e., a second boosting composition).

The claimed invention is further describe by way of the following non-limiting examples. Further aspects and embodiments of the present invention will be apparent to those of ordinary skill in the art, in view of the above disclosure and following experimental exemplification, included by way of illustration and not limitation, and with reference to the attached figures.

EXAMPLES

Example 1. MVA Vaccine Vectors

This Example provides information on exemplary MVA vaccine vectors. An MVA vaccine is constructed using MVA strain 1974/NIH that has been genetically modified to express two other genes: the VP40 protein of Marburgvirus and a chimeric protein consisting of portions of the human MUC1 protein and of the Marburgvirus glycoprotein (GP). The chimeric MUC1/GP gene has more a particular construction of encoding transmembrane protein with an extracellular domain derived from the human MUC1 gene, a transmembrane domain derived from the glycoprotein of Marburgvirus, and the intracellular domain of human MUC1 gene. The methods for creating the MUC1/GP chimeric protein are given in detail in EXAMPLE 2 below. The methods for generating an MVA vaccine genetically modified to express the MUC1/GP and VP40 proteins and the characterization of the hypoglycosylation status of the MUC1 thereby encoded are given in detail in EXAMPLE 3 below.

Table 2. Lists the accession numbers for the GenBank sequences used for design of the MVA vaccine vectors of this invention

TABLE 2

MVA vaccine vectors of this invention, source of sequences

| Design element | GenBank accession numbers for source sequence |
| --- | --- |
| MUC1 | NM_001204285 |
| Marburgvirus GP | JX458834 |
| Marburgvirus VP40 | JX458834 |

Example 2. Sequence Optimization

Example 2 illustrates the process for optimization of MUC1 sequences for use in an MVA vaccine vector. This Example shows the optimization of MUC1 sequence which is included in GEO-MUC1. The process followed for vaccines against other strains is highly similar, involving the same set of operations.

Muc1/4TR Gene Optimization

1. Start with the natural sequence
*Homo sapiens* mucin 1: NCBI Reference Sequence: NM_001204285.1
Copy/paste the sequence from GenBank and Save as a SeqBuilder file: Muc1-1TR_001204285

Muc1 Sequence containing Only 1 Tandem Repeat (1428 nt)

(SEQ ID NO: 5)

ATGACACCGGGCACCCAGTCTCCTTTCTTCCTGCTGCTGCTCCTCACAGTGCTTACAGTTGTTACGGGTTCTGGTCA

TGCAAGCTCTACCCCAGGTGGAGAAAAGGAGACTTCGGCTACCCAGAGAAGTTCAGTGCCCAGCTCTACTGAGAAGA

ATGCTGTGAGTATGACCAGCAGCGTACTCTCCAGCCACAGCCCCGGTTCAGGCTCCTCCACCACTCAGGGACAGGAT

GTCACTCTGGCCCCGGCCACGGAACCAGCTTCAGGTTCAGCTGCCACCTGGGGACAGGATGTCACCTCGGTCCCAGT

CACCAGGCCAGCCCTGGGCTCCACCACCCCGCCAGCCCACGATGTCACCTCAGCCCCGGACAACAAGCCAGCCCCGG

GCTCCACCGCCCCCCCA GCCCACGGTGTCACCTCGGCCCCGGACACCAGGCCGGCCCCGGGCTCCACCGCCCCCCCA

GCCCATGGTGTCACCTCGGCCCCGGACAACAGGCCCGCCTTGGGCTCCACCGCCCCTCCAGTCCACAATGTCACCTC

GGCCTCAGGCTCTGCATCAGGCTCAGCTTCTACTCTGGTGCACAACGGCACCTCTGCCAGGGCTACCACAACCCCAG

CCAGCAAGAGCACTCCATTCTCAATTCCCAGCCACCACTCTGATACTCCTACCACCCTTGCCAGCCATAGCACCAAG

ACTGATGCCAGTAGCACTCACCATAGCACGGTACCTCCTCTCACCTCCTCCAATCACAGCACTTCTCCCCAGTTGTC

TACTGGGGTCTCTTTCTTTTTCCTGTCTTTTCACATTTCAAACCTCCAGTTTAATTCCTCTCTGGAAGATCCCAGCA

CCGACTACTACCAAGAGCTGCAGAGAGACATTTCTGAAATGTTTTTGCAGATTTATAAACAAGGGGGTTTTCTGGGC

CTCTCCAATATTAAGTTCAGGCCAGGATCTGTGGTGGTACAATTGACTCTGGCCTTCCGAGAAGGTACCATCAATGT

CCACGACGTGGAGACACAGTTCAATCAGTATAAAACGGAAGCAGCCTCTCGATATAACCTGACGATCTCAGACGTCA

GCGTGAGTGATGTGCCATTTCCTTTCTCTGCCCAGTCTGGGGCTGGGGTGCCAGGCTGGGGCATCGCGCTGCTGGTG

CTGGTCTGTGTTCTGGTTGCGCTGGCCATTGTCTATCTCATTGCCTTGGCTGTCTGTCAGTGCCGCCGAAAGAACTA

CGGGCAGCTGGACATCTTTCCAGCCCGGGATACCTACCATCCTATGAGCGAGTACCCCACCTACCACACCCATGGGC

-continued

GCTATGTGCCCCCTAGCAGTACCGATCGTAGCCCCTATGAGAAGGTTTCTGCAGGTAATGGTGGCAGCAGCCTCTCT

TACACAAACCCAGCAGTGGCAGCCACTTCTGCCAACTTGTAG

Muc1/1TR protein (475 aa)

(SEQ ID NO: 6)

MTPGTQSPFFLLLLLTVLTVVTGSGHASSTPGGEKETSATQRSSVPSSTEKNAVSMTSSVLSSHSPGSGSSTTQGQD

VTLAPATEPASGSAATWGQDVTSVPVTRPALGSTTPPAHDVTSAPDNKPAPGSTAPPAHGVTSAPDTRPAPGSTAPP

AHGVTSAPDNRPALGSTAPPVHNVTSASGSASGSASTLVHNGTSARATTTPASKSTPFSIPSHHSDTPTTLASHSTK

TDASSTHHSTVPPLTSSNHSTSPQLSTGVSFFFLSFHISNLQFNSSLEDPSTDYYQELQRDISEMFLQIYKQGGFLG

LSNIKFRPGSVVVQLTLAFREGTINVHDVETQFNQYKTEAASRYNLTISDVSVSDVPFPFSAQSGAGVPGWGIALLV

LVCVLVALAIVYLIALAVCQCRRKNYGQLDIFPARDTYHPMSEYPTYHTHGRYVPPSSTDRSPYEKVSAGNGGSSLS

YTNPAVAATSANL

Sequence Key:
BOX: Signal Peptide
ITALICS BOX: Tandem Repeats
BOLD: Transmembrane Domain
UNDERLINE: Cytoplasmic Tail 2. GeoVax decided to go with a Muc1 gene that contain 4 Tandem Repeats
   Add for extra Tandem Repeats on the Muc1-1TR_001204285.
   Name the new sequence as: GVX-Muc1/4TR.01

GeoVax Muc1/4TR sequence (1608 nt)

(SEQ ID NO: 7)

ATGACACCGGGCACCCAGTCTCCTTTCTTCCTGCTGCTGCTCCTCACAGTGCTTACAGTTGTTACGGGTTCTGGTC

ATGCAAGCTCTACCCCAGGTGGAGAAAAGGAGACTTCGGCTACCCAGAGAAGTTCAGTGCCCAGCTCTACTGAGAA

GAATGCTGTGAGTATGACCAGCAGCGTACTCTCCAGCCACAGCCCCGGTTCAGGCTCCTCCACCACTCAGGGACAG

GATGTCACTCTGGCCCCGGCCACGGAACCAGCTTCAGGTTCAGCTGCCACCTGGGGACAGGATGTCACCTCGGTCC

CAGTCACCAGGCCAGCCCTGGGCTCCACCACCCCGCCAGCCCACGATGTCACCTCAGCCCCGGACAACAAGCCAGC

CCCGGGCTCCACCGCCCCCCCA*GCCCACGGTGTCACCTCGGCCCCGGACACCAGGCCGGCCCCGGGCTCCACCGCC*

*CCCCCAGCCCACGGTGTCACCTCGGCCCCGGACACCAGGCCGGCCCCGGGCTCCACCGCCCCCCCAGCCCCACGGTG*

*TCACCTCGGCCCCGGACACCAGGCCGGCCCCGGGCTCCACCGCCCCCCCAGCCCACGGTGTCACCTCGGCCCCGGA*

*CACCAGGCCGGCCCCGGGCTCCACCGCCCCCCCA*GCCCATGGTGTCACCTCGGCCCCGGACAACAGGCCCGCCTTG

GGCTCCACCGCCCCTCCAGTCCACAATGTCACCTCGGCCTCAGGCTCTGCATCAGGCTCAGCTTCTACTCTGGTGC

ACAACGGCACCTCTGCCAGGGCTACCACAACCCCAGCCAGCAAGAGCACTCCATTCTCAATTCCCAGCCACCACTC

TGATACTCCTACCACCCTTGCCAGCCATAGCACCAAGACTGATGCCAGTAGCACTCACCATAGCACGGTACCTCCT

CTCACCTCCTCCAATCACAGCACTTCTCCCCAGTTGTCTACTGGGGTCTCTTTCTTTTTCCTGTCTTTTCACATTT

CAAACCTCCAGTTTAATTCCTCTCTGGAAGATCCCAGCACCGACTACTACCAAGAGCTGCAGAGAGACATTTCTGA

AATGTTTTTGCAGATTTATAAACAAGGGGGTTTTCTGGGCCTCTCCAATATTAAGTTCAGGCCAGGATCTGTGGTG

GTACAATTGACTCTGGCCTTCCGAGAAGGTACCATCAATGTCCACGACGTGGAGACACAGTTCAATCAGTATAAAA

CGGAAGCAGCCTCTCGATATAACCTGACGATCTCAGACGTCAGCGTGAGTGATGTGCCATTTCCTTTCTCTGCCCA

GTCTGGGGCTGGGGTGCCAGGCTGGGGCATCGCGCTGCTGGTGCTGGTCTGTGTTCTGGTTGCGCTGGCCATTGTC

TATCTCATTGCCTTGGCTGTCTGTCAGTGCCGCCGAAAGAACTACGGGCAGCTGGACATCTTTCCAGCCCGGGATA

CCTACCATCCTATGAGCGAGTACCCCACCTACCACACCCATGGGCGCTATGTGCCCCCTAGCAGTACCGATCGTAG

CCCCTATGAGAAGGTTTCTGCAGGTAATGGTGGCAGCAGCCTCTCTTACACAAACCCAGCAGTGGCAGCCACTTCT

GCCAACTTGTAG

Muc1/4TR protein (535 aa)

(SEQ ID NO: 8)

MTPGTQSPFFLLLLLTVLTVVTGSGHASSTPGGEKETSATQRSSVPSSTEKNAVSMTSSVLSSHSPGSGSSTTQGQ

DVTLAPATEPASGSAATWGQDVTSVPVTRPALGSTTPPAHDVTSAPDNKPAPGSTAPPAHGVTSAPDTRPAPGSTA

PPAHGVTSAPDTRPAPGSTAPP*AHGVTSAPDTRPAPGSTAPP*AHGVTSAPDTRPAPGSTAPPAHGVTSAPDNRPAL

GSTAPPVHNVTSASGSASGSASTLVHNGTSARATTTPASKSTPFSIPSHHSDTPTTLASHSTKTDASSTHHSTVPP

LTSSNHSTSPQLSTGVSFEELSFHISNLQFNSSLEDPSTDYYQELQRDISEMFLQTYKQGGFLGLSNIKFRPGSVV

VQLTLAFREGTINVHDVETQFNQYKTEAASRYNLTISDVSVSDVPFPFSAQSGAGVPGWGIALLVLVCVLVALAIV

YLIALAVCQCRRKNYGQLDIFPARDTYHPMSEYPTYHTHGRYVPPSSTDRSPYEKVSAGNGGSSLSYTNPAVAATS

ANL
Sequence Key:
BOX: Signal Peptide
ITALICS BOX BOLD BOX: Sequential Tandem Repeats
BOLD: Transmembrane Domain
UNDERLINE: Cytoplasmic Tail Align Muc1-1TR_001204285 sequence with GVX-Muc1/4TR.01

| CLUSTAL 2.1 Multiple Sequence Alignments Sequence format is Pearson |
| Sequence: Muc1/1TR 1428 aa (Muc1-1TR_001204285) (SEQ ID NO: 5) |
| Sequence: Muc1/4TR 1608 aa (GVX-Muc1/4TR.01) (SEQ ID NO: 7) |

```
Muc1/1TR     ATGACACCGGGCACCCAGTCTCCTTTCTTCCTGCTGCTGCTCCTCACAGTGCTTACAGTT
Muc1/4TR     ATGACACCGGGCACCCAGTCTCCTTTCTTCCTGCTGCTGCTCCTCACAGTGCTTACAGTT
             ************************************************************

Muc1/1TR     GTTACGGGTTCTGGTCATGCAAGCTCTACCCCAGGTGGAGAAAAGGAGACTTCGGCTACC
Muc1/4TR     GTTACGGGTTCTGGTCATGCAAGCTCTACCCCAGGTGGAGAAAAGGAGACTTCGGCTACC
             ************************************************************

Muc1/1TR     CAGAGAAGTTCAGTGCCCAGCTCTACTGAGAAGAATGCTGTGAGTATGACCAGCAGCGTA
Muc1/4TR     CAGAGAAGTTCAGTGCCCAGCTCTACTGAGAAGAATGCTGTGAGTATGACCAGCAGCGTA
             ************************************************************

Muc1/1TR     CTCTCCAGCCACAGCCCCGGTTCAGGCTCCTCCACCACTCAGGGACAGGATGTCACTCTG
Muc1/4TR     CTCTCCAGCCACAGCCCCGGTTCAGGCTCCTCCACCACTCAGGGACAGGATGTCACTCTG
             ************************************************************

Muc1/1TR     GCCCCGGCCACGGAACCAGCTTCAGGTTCAGCTGCCACCTGGGGACAGGATGTCACCTCG
Muc1/4TR     GCCCCGGCCACGGAACCAGCTTCAGGTTCAGCTGCCACCTGGGGACAGGATGTCACCTCG
             ************************************************************

Muc1/1TR     GTCCCAGTCACCAGGCCAGCCCTGGGCTCCACCACCCCGCCAGCCCACGATGTCACCTCA
Muc1/4TR     GTCCCAGTCACCAGGCCAGCCCTGGGCTCCACCACCCCGCCAGCCCACGATGTCACCTCA
             ************************************************************

Muc1/1TR     GCCCCGGACAACAAGCCAGCCCCGGGCTCCACCGCCCCCCCAGCCCACGGTGTCACCTCG
Muc1/4TR     GCCCCGGACAACAAGCCAGCCCCGGGCTCCACCGCCCCCCCAGCCCACGGTGTCACCTCG
             ************************************************************

Muc1/1TR     GCCCCGGACACCAGGCCGGCCCCGG-----------------------------------
Muc1/4TR     GCCCCGGACACCAGGCCGGCCCCGGGCTCCACCGCCCCCCCAGCCCACGGTGTCACCTCG
             *************************

Muc1/1TR     ------------------------------------------------------------
Muc1/4TR     GCCCCGGACACCAGGCCGGCCCCGGGCTCCACCGCCCCCCCAGCCCACGGTGTCACCTCG

Muc1/1TR     ------------------------------------------------------------
Muc1/4TR     GCCCCGGACACCAGGCCGGCCCCGGGCTCCACCGCCCCCCCAGCCCACGGTGTCACCTCG

Muc1/1TR     ------------------------GCTCCACCGCCCCCCCAGCCCATGGTGTCACCTCG
Muc1/4TR     GCCCCGGACACCAGGCCGGCCCCGGGCTCCACCGCCCCCCCAGCCCATGGTGTCACCTCG
                                     ***********************************
```

-continued

```
Muc1/1TR    GCCCCGGACAACAGGCCCGCCTTGGGCTCCACCGCCCCTCCAGTCCACAATGTCACCTCG
Muc1/4TR    GCCCCGGACAACAGGCCCGCCTTGGGCTCCACCGCCCCTCCAGTCCACAATGTCACCTCG
            ************************************************************

Muc1/1TR    GCCTCAGGCTCTGCATCAGGCTCAGCTTCTACTCTGGTGCACAACGGCACCTCTGCCAGG
Muc1/4TR    GCCTCAGGCTCTGCATCAGGCTCAGCTTCTACTCTGGTGCACAACGGCACCTCTGCCAGG
            ************************************************************

Muc1/1TR    GCTACCACAACCCCAGCCAGCAAGAGCACTCCATTCTCAATTCCCAGCCACCACTCTGAT
Muc1/4TR    GCTACCACAACCCCAGCCAGCAAGAGCACTCCATTCTCAATTCCCAGCCACCACTCTGAT
            ************************************************************

Muc1/1TR    ACTCCTACCACCCTTGCCAGCCATAGCACCAAGACTGATGCCAGTAGCACTCACCATAGC
Muc1/4TR    ACTCCTACCACCCTTGCCAGCCATAGCACCAAGACTGATGCCAGTAGCACTCACCATAGC
            ************************************************************

Muc1/1TR    ACGGTACCTCCTCTCACCTCCTCCAATCACAGCACTTCTCCCCAGTTGTCTACTGGGGTC
Muc1/4TR    ACGGTACCTCCTCTCACCTCCTCCAATCACAGCACTTCTCCCCAGTTGTCTACTGGGGTC
            ************************************************************

Muc1/1TR    TCTTTCTTTTTCCTGTCTTTTCACATTTCAAACCTCCAGTTTAATTCCTCTCTGGAAGAT
Muc1/4TR    TCTTTCTTTTTCCTGTCTTTTCACATTTCAAACCTCCAGTTTAATTCCTCTCTGGAAGAT
            ************************************************************

Muc1/1TR    CCCAGCACCGACTACTACCAAGAGCTGCAGAGAGACATTTCTGAAATGTTTTTGCAGATT
Muc1/4TR    CCCAGCACCGACTACTACCAAGAGCTGCAGAGAGACATTTCTGAAATGTTTTTGCAGATT
            ************************************************************

Muc1/1TR    TATAAACAAGGGGGTTTTCTGGGCCTCTCCAATATTAAGTTCAGGCCAGGATCTGTGGTG
Muc1/4TR    TATAAACAAGGGGGTTTTCTGGGCCTCTCCAATATTAAGTTCAGGCCAGGATCTGTGGTG
            ************************************************************

Muc1/1TR    GTACAATTGACTCTGGCCTTCCGAGAAGGTACCATCAATGTCCACGACGTGGAGACACAG
Muc1/4TR    GTACAATTGACTCTGGCCTTCCGAGAAGGTACCATCAATGTCCACGACGTGGAGACACAG
            ************************************************************

Muc1/1TR    TTCAATCAGTATAAAACGGAAGCAGCCTCTCGATATAACCTGACGATCTCAGACGTCAGC
Muc1/4TR    TTCAATCAGTATAAAACGGAAGCAGCCTCTCGATATAACCTGACGATCTCAGACGTCAGC
            ************************************************************

Muc1/1TR    GTGAGTGATGTGCCATTTCCTTTCTCTGCCCAGTCTGGGGCTGGGGTGCCAGGCTGGGGC
Muc1/4TR    GTGAGTGATGTGCCATTTCCTTTCTCTGCCCAGTCTGGGGCTGGGGTGCCAGGCTGGGGC
            ************************************************************

Muc1/1TR    ATCGCGCTGCTGGTGCTGGTCTGTGTTCTGGTTGCGCTGGCCATTGTCTATCTCATTGCC
Muc1/4TR    ATCGCGCTGCTGGTGCTGGTCTGTGTTCTGGTTGCGCTGGCCATTGTCTATCTCATTGCC
            ************************************************************

Muc1/1TR    TTGGCTGTCTGTCAGTGCCGCCGAAAGAACTACGGGCAGCTGGACATCTTTCCAGCCCGG
Muc1/4TR    TTGGCTGTCTGTCAGTGCCGCCGAAAGAACTACGGGCAGCTGGACATCTTTCCAGCCCGG
            ************************************************************

Muc1/1TR    GATACCTACCATCCTATGAGCGAGTACCCCACCTACCACACCCATGGGCGCTATGTGCCC
Muc1/4TR    GATACCTACCATCCTATGAGCGAGTACCCCACCTACCACACCCATGGGCGCTATGTGCCC
            ************************************************************

Muc1/1TR    CCTAGCAGTACCGATCGTAGCCCCTATGAGAAGGTTTCTGCAGGTAATGGTGGCAGCAGC
Muc1/4TR    CCTAGCAGTACCGATCGTAGCCCCTATGAGAAGGTTTCTGCAGGTAATGGTGGCAGCAGC
            ************************************************************

Muc1/1TR    CTCTCTTACACAAACCCAGCAGTGGCAGCCACTTCTGCCAACTTGTAG
Muc1/4TR    CTCTCTTACACAAACCCAGCAGTGGCAGCCACTTCTGCCAACTTGTAG
            ************************************************
```

```
              CLUSTAL, 2.1 Multiple Sequence Alignments
                    Sequence format is Pearson
      Sequence: Muc1/1TR 475 aa (Muc1-1TR_001204285) (SEQ ID NO: 6)
      Sequence: Muc1/4TR 535 aa (GVX-Muc1/4TR.01) (SEQ ID NO: 8)
                        Alignment Score 2859
```

```
Muc1/1TR    MTPGTQSPFFLLLLLTVLTVVTGSGHASSTPGGEKETSATQRSSVPSSTEKNAVSMTSSV
Muc1/4TR    MTPGTQSPFFLLLLLTVLTVVTGSGHASSTPGGEKETSATQRSSVPSSTEKNAVSMTSSV
            ************************************************************

Muc1/1TR    LSSHSPGSGSSTTQGQDVTLAPATEPASGSAATWGQDVTSVPVTRPALGSTTPPAHDVTS
Muc1/4TR    LSSHSPGSGSSTTQGQDVTLAPATEPASGSAATWGQDVTSVPVTRPALGSTTPPAHDVTS
            ************************************************************
```

```
Muc1/1TR    APDNKPAPGSTAPPAHGVTSAPDTRPAP---------------------------------
Muc1/4TR    APDNKPAPGSTAPPAHGVTSAPDTRPAPGSTAPPAHGVTSAPDTRPAPGSTAPPAHGVTS
            ***************************

Muc1/1TR    ---------------------------GSTAPPAHGVTSAPDNRPALGSTAPPVHNVTS
Muc1/4TR    APDTRPAPGSTAPPAHGVTSAPDTRPAPGSTAPPAHGVTSAPDNRPALGSTAPPVHNVTS
                                       *********************************

Muc1/1TR    ASGSASGSASTLVHNGTSARATTTPASKSTPFSIPSHHSDTPTTLASHSTKTDASSTHHS
Muc1/4TR    ASGSASGSASTLVHNGTSARATTTPASKSTPFSIPSHHSDTPTTLASHSTKTDASSTHHS
            ************************************************************

Muc1/1TR    TVPPLTSSNHSTSPQLSTGVSFFFLSFHISNLQFNSSLEDPSTDYYQELQRDISEMFLQI
Muc1/4TR    TVPPLTSSNHSTSPQLSTGVSFFFLSFHISNLQFNSSLEDPSTDYYQELQRDISEMFLQI
            ************************************************************

Muc1/1TR    YKQGGFLGLSNIKFRPGSVVVQLTLAFREGTINVHDVETQFNQYKTEAASRYNLTISDVS
Muc1/4TR    YKQGGFLGLSNIKFRPGSVVVQLTLAFREGTINVHDVETQFNQYKTEAASRYNLTISDVS
            ************************************************************

Muc1/1TR    VSDVPFPFSAQSGAGVPGWGIALLVLVCVLVALAIVYLIALAVCQCRRKNYGQLDIFPAR
Muc1/4TR    VSDVPFPFSAQSGAGVPGWGIALLVLVCVLVALAIVYLIALAVCQCRRKNYGQLDIFPAR
            ************************************************************

Muc1/1TR    DTYHPMSEYPTYHTHGRYVPPSSTDRSPYEKVSAGNGGSSLSYTNPAVAATSANL
Muc1/4TR    DTYHPMSEYPTYHTHGRYVPPSSTDRSPYEKVSAGNGGSSLSYTNPAVAATSANL
            *******************************************************
```

To increase the efficiency of the incorporation of Muc1 into Marburg VP40-based VLPs, the transmembrane domain of Muc1 was replaced with the transmembrane domain of the Marburg virus glycoprotein.

```
Marburg Glycoprotein Sequence (TM sequence position 1930-2019 on Marburg GP)
                                                              (SEQ ID NO: 9)
ATGTGGACTACATGCTTCTTTATCAGTCTCATCTTGATCCAAGGGATAAAAACTCTCCCTATTTTGGAGATAGCCAG

TAACGATCAACCCCAAAATGTGGATTCGGTATGCTCCGGAACTCTCCAGAAAACAGAAGACGTCCATCTGATGGGAT

TTACACTGAGCGGGCAGAAAGTTGCTGATTCCCCTTTGGAGGCATCCAAGCGATGGGCTTTCAGGACAGGTGTACCT

CCTAAGAATGTTGAGTATACGGAAGGGGAGGAAGCCAAAACATGCTACAATATAAGTGTAACGGATCCCTCTGGAAA

ATCCTTGCTGTTAGATCCTCCCACCAACGTCCGAGACTATCCTAAATGCAAAACTATCCATCACATTCAAGGTCAAA

ACCCTCATGCGCAGGGGATCGCCCTCCATTTGTGGGGAGCATTTTTCCTATATGATCGCATTGCCTCCACAACAATG

TACCGAGGCAAAGTCTTCACTGAAGGGAACATAGCAGCCATGATTGTCAATAAGACAGTGCACAAAATGATTTTCTC

GAGGCAAGGACAAGGGTACCGTCACATGAATCTGACTTCTACTAATAAATATTGGACAAGTAGCAACGGAACGCAAA

CAAATGACACTGGATGCTTTGGTACTCTTCAAGAATACAATTCTACGAAGAACCAAACATGTGCTCCGTCTAAAACA

CCCCCACCACCGCCCACAGCCCATCCGGAGATCAAACCCACAAGCACCCCAACCGATGCCACTAGACTCAACACCAC

AAACCCAAACAGTGATGATGAGGATCTCACAACATCCGGCTCAGGGTCTGGGGAACAGGAACCCTATACGACTTCTG

ATGCGGTCACTAAGCAAGGGCTTTCATCAACAATGCCACCCACTCTCTCACCGCAACCAGGCACGCCACAGCAAGGA

GGAAACAACACAAACCACTCCCAAGACGCTGCAACTGAACTTGACAACACCAATACAACTGCACAACCGCCCATGCC

CTCCCACAACACCACCACAATCTCCACCAACAACACCTCCAAACACAACCTCAGCACCCTCTCCGAACCACCACAAA

ACACCACCAATCCCAACACACAAAGCATGGCCACTGAAAATGAGAAAACCAGTGCCCCCCCGAAAACAACCCTGCCT

CCAACAGAAAGTCCTACCACAGAAAAGAGCACCAACAATACAAAAAGCCCCACCACAATGGAACCAAATACAACAAA

CGGACATTTCACTAGTCCCTCCTCCACCCCCAACTCGACTACTCAACATCTTATATATTTCAGGAGGAAACGAAGTA

TCCTCTGGAGGGAAGGCGACATGTTCCCTTTTCTAGATGGGTTAATAAATGCTCCAATTGATTTTGATCCAGTTCCA

AATACAAAGACAATCTTTGATGAATCTTCTAGTTCTGGTGCTTCAGCCGAGGAAGATCAACATGCATCCTCCAATAT

CAGTTTAACTTTATCTTATCTTCCTCATACAAGTGAAAACACTGCCTACTCTGGAGAAAATGAAAATGATTGTGATG
```

-continued

CAGAGCTAAGAATTTGGAGCGTTCAGGAGGACGACCTGGCAGCAGGGCTCAGTTGGATACCATTTTTTGGCCCTGGA

ATCGAAGGACTTTATACCGCTGGTTTAATTAAAAATCAAAACAATTTGGTCTGCAGGTTGAGGCGTCTAGCCAATCA

AACTGCAAAATCTTTGGAACTCTTACTAAGGGTCACAACCGAGGAAAGAACATTTTCTTTAATCAATAGACATGCTA

TTGACTTTCTACTCACAAGGTGGGGAGGAACATGCAAAGTGCTTGGACCCGATTGTTGCATAGGAATAGAGGACTTG

TCCAGAAATATTTCAGAACAGATTGACCAAATCAAGAAGGACGAACAAAAAGAGGGGACTGGTTGGGGTCTGGGTGG

TAAATGGTGGACATCCGACTGGGGTGTTCTTACTAACTTGGGCATCTTACTACTATTGTCCATAGCTGTCTTGATTG

CTCTATCCTGTATTTGTCGTATCTTTACTAAATATATTGGATAG

Marburg Glycoprotein (TM sequence position 644-673 on Marburg GP)

(SEQ ID NO: 10)

MWTTCFFISLILIQGIKTLPILEIASNDQPQNVDSVCSGTLQKTEDVHLMGFTLSGQKVADSPLEASKRWAFRTGVP

PKNVEYTEGEEAKTCYNISVTDPSGKSLLLDPPTNVRDYPKCKTIHHIQGQNPHAQGIALHLWGAFFLYDRIASTTM

YRGKVFTEGNIAAMIVNKTVHKMIFSRQGQGYRHMNLTSTNKYWTSSNGTQTNDTGCFGTLQEYNSTKNQTCAPSKT

PPPPPTAHPEIKPTSTPTDATRLNTTNPNSDDEDLTTSGSGSGEQEPYTTSDAVTKQGLSSTMPPTLSPQPGTPQQG

GNNTNHSQDAATELDNTNTTAQPPMPSHNTTTISTNNTSKHNLSTLSEPPQNTTNPNTQSMATENEKTSAPPKTTLP

PTESPTTEKSTNNTKSPTTMEPNTTNGHFTSPSSTPNSTTQHLIYFRRKRSILWREGDMFPFLDGLINAPIDFDPVP

NTKTIFDESSSSGASAEEDQHASSNISLTLSYLPHTSENTAYSGENENDCDAELRIWSVQEDDLAAGLSWIPFFGPG

IEGLYTAGLIKNQNNLVCRLRRLANQTAKSLELLLRVTTEERTFSLINRHAIDFLLTRWGGTCKVLGPDCCIGIEDL

SRNISEQIDQIKKDEQKEGTGWGLGGKWWTSDWGVLTNLGILLLLSIAVLIALSCICRIFTKYIG

GeoVax Muc1/4TR sequence (Transmembrane domain sequence: position 1129-1218 on Muc1/1TR)

(SEQ ID NO: 11)

ATGACACCGGGCACCCAGTCTCCTTTCTTCCTGCTGCTGCTCCTCACAGTGCTTACAGTTGTTACGGGTTCTGGTCA

TGCAAGCTCTACCCCAGGTGGAGAAAAGGAGACTTCGGCTACCCAGAGAAGTTCAGTGCCCAGCTCTACTGAGAAGA

ATGCTGTGAGTATGACCAGCAGCGTACTCTCCAGCCACAGCCCCGGTTCAGGCTCCTCCACCACTCAGGGACAGGAT

GTCACTCTGGCCCCGGCCACGGAACCAGCTTCAGGTTCAGCTGCCACCTGGGGACAGGATGTCACCTCGGTCCCAGT

CACCAGGCCAGCCCTGGGCTCCACCACCCCGCCAGCCCACGATGTCACCTCAGCCCCGGACAACAAGCCAGCCCCGG

GCTCCACCGCCCCCCCA⌈GCCCACGGTGTCACCTCGGCCCCGGACACCAGGCCGGCCCCGGGCTCCACCGCCCCCCCA

GCCCACGGTGTCACCTCGGCCCCGGACACCAGGCCGGCCCCGGGCTCCACCGCCCCCCCA⌋*GCCCACGGTGTCACCTC*

*GGCCCCGGACACCAGGCCGGCCCCGGGCTCCACCGCCCCCCCA*GCCCACGGTGTCACCTCGGCCCCGGACACCAGGC

CGGCCCCGGGCTCCACCGCCCCCCCA⌋GCCCATGGTGTCACCTCGGCCCCGGACAACAGGCCCGCCTTGGGCTCCACC

GCCCCTCCAGTCCACAATGTCACCTCGGCCTCAGGCTCTGCATCAGGCTCAGCTTCTACTCTGGTGCACAACGGCAC

CTCTGCCAGGGCTACCACAACCCCAGCCAGCAAGAGCACTCCATTCTCAATTCCCAGCCACCACTCTGATACTCCTA

CCACCCTTGCCAGCCATAGCACCAAGACTGATGCCAGTAGCACTCACCATAGCACGGTACCTCCTCTCACCTCCTCC

AATCACAGCACTTCTCCCCAGTTGTCTACTGGGGTCTCTTTCTTTTTCCTGTCTTTTCACATTTCAAACCTCCAGTT

TAATTCCTCTCTGGAAGATCCCAGCACCGACTACTACCAAGAGCTGCAGAGAGACATTTCTGAAATGTTTTTGCAGA

TTTATAAACAAGGGGGTTTTCTGGGCCTCTCCAATATTAAGTTCAGGCCAGGATCTGTGGTGGTACAATTGACTCTG

GCCTTCCGAGAAGGTACCATCAATGTCCACGACGTGGAGACACAGTTCAATCAGTATAAAACGGAAGCAGCCTCTCG

ATATAACCTGACGATCTCAGACGTCAGCGTGAGTGATGTGCCATTTCCTTTCTCTGCCCAGTCTGGGGCTGGGGTGC

CAGGCTGGGGCATCGCGCTGCTGGTGCTGGTCTGTGTTCTGGTTGCGCTGGCCATTGTCTATCTCATTGCCTTGGCT

GTCTGTCAGTGCCGCCGAAAGAACTACGGGCAGCTGGACATCTTTCCAGCCCGGGATACCTACCATCCTATGAGCGA

-continued

GTACCCCACCTACCACACCCATGGGCGCTATGTGCCCCCTAGCAGTACCGATCGTAGCCCCTATGAGAAGGTTTCTG

CAGGTAATGGTGGCAGCAGCCTCTCTTACACAAACCCAGCAGTGGCAGCCACTTCTGCCAACTTGTAG (Transmembrane domain sequence: position 157-186 on Muc1/1TR)

(SEQ ID NO: 12)

MTPGTQSPFFLLLLLTVLTVVTGSGHASSTPGGEKETSATQRSSVPSSTEKNAVSMTSSVLSSHSPGSGSSTTQGQD

VTLAPATEPASGSAATWGQDVTSVPVTRPALGSTTPPAHDVTSAPDNKPAPGSTAPP*AHGVTSAPDTRPAPGSTAPP*

AHGVTSAPDTRPAPGSTAPP*AHGVTSAPDTRPAPGSTAPP*AHGVTSAPDTRPAPGSTAPPAHGVTSAPDNRPALGST

APPVHNVTSASGSASGSASTLVHNGTSARATTTPASKSTPFSIPSHHSDTPTTLASHSTKTDASSTHHSTVPPLTSS

NHSTSPQLSTGVSFFFLSFHISNLQFNSSLEDPSTDYYQELQRDISEMFLQIYKQGGFLGLSNIKFRPGSVVVQLTL

AFREGTINVHDVETQFNQYKTEAASRYNLTISDVSVSDVPFPFSAQSGAGVPGWGIALLVLVCVLVALAIVYLIALA

VCQCRRKNYGQLDIFPARDTYHPMSEYPTYHTHGRYVPPSSTDRSPYEKVSAGNGGSSLSYTNPAVAATSANL

Replace TM sequence on the GVX-Muc1/4TR.01 with the TM sequence of Marburg GP:

(SEQ ID NO: 13)

WWTSDWGVLTNLGILLLLSIAVLIALSCIC

Name the new sequence as: GVX-Muc1_4TRMTm.02

(SEQ ID NO:14)

ATGACACCGGGCACCCAGTCTCCTTTCTTCCTGCTGCTGCTCCTCACAGTGCTTACAGTTGTTACGGGTTCTGGTCA

TGCAAGCTCTACCCCAGGTGGAGAAAAGGAGACTTCGGCTACCCAGAGAAGTTCAGTGCCCAGCTCTACTGAGAAGA

ATGCTGTGAGTATGACCAGCAGCGTACTCTCCAGCCACAGCCCCGGTTCAGGCTCCTCCACCACTCAGGGACAGGAT

GTCACTCTGGCCCCGGCCACGGAACCAGCTTCAGGTTCAGCTGCCACCTGGGGACAGGATGTCACCTCGGTCCCAGT

CACCAGGCCAGCCCTGGGCTCCACCACCCCGCCAGCCCACGATGTCACCTCAGCCCCGGACAACAAGCCAGCCCCGG

GCTCCACCGCCCCCCCA*GCCCACGGTGTCACCTCGGCCCCGGACACCAGGCCGGCCCCGGGCTCCACCGCCCCCCCA*

GCCCACGGTGTCACCTCGGCCCCGGACACCAGGCCGGCCCCGGGCTCCACCGCCCCCCCA*GCCCACGGTGTCACCTC*

*GGCCCCGGACACCAGGCCGGCCCCGGGCTCCACCGCCCCCCCA*GCCCACGGTGTCACCTCGGCCCCGGACACCAGGC

CGGCCCCGGGCTCCACCGCCCCCCCAGCCCATGGTGTCACCTCGGCCCCGGACAACAGGCCCGCCTTGGGCTCCACC

GCCCCTCCAGTCCACAATGTCACCTCGGCCTCAGGCTCTGCATCAGGCTCAGCTTCTACTCTGGTGCACAACGGCAC

CTCTGCCAGGGCTACCACAACCCCAGCCAGCAAGAGCACTCCATTCTCAATTCCCAGCCACCACTCTGATACTCCTA

CCACCCTTGCCAGCCATAGCACCAAGACTGATGCCAGTAGCACTCACCATAGCACGGTACCTCCTCTCACCTCCTCC

AATCACAGCACTTCTCCCCAGTTGTCTACTGGGGTCTCTTTCTTTTTCCTGTCTTTTCACATTTCAAACCTCCAGTT

TAATTCCTCTCTGGAAGATCCCAGCACCGACTACTACCAAGAGCTGCAGAGAGACATTTCTGAAATGTTTTTGCAGA

TTTATAAACAAGGGGGTTTTCTGGGCCTCTCCAATATTAAGTTCAGGCCAGGATCTGTGGTGGTACAATTGACTCTG

GCCTTCCGAGAAGGTACCATCAATGTCCACGACGTGGAGACACAGTTCAATCAGTATAAAACGGAAGCAGCCTCTCG

ATATAACCTGACGATCTCAGACGTCAGCGTGAGTGATGTGCCATTTCCTTTCTCTGCCCAGTCTGGGGCTGGGGTGT

GGTGGACATCCGACTGGGGTGTTCTTACTAACTTGGGCATCTTACTACTATTGTCCATAGCTGTCTTGATTGCTCTA

TCCTGTATTTGTCGCCGAAAGAACTACGGGCAGCTGGACATCTTTCCAGCCCGGGATACCTACCATCCTATGAGCGA

GTACCCCACCTACCACACCCATGGGCGCTATGTGCCCCCTAGCAGTACCGATCGTAGCCCCTATGAGAAGGTTTCTG

CAGGTAATGGTGGCAGCAGCCTCTCTTACACAAACCCAGCAGTGGCAGCCACTTCTGCCAACTTGTAG

Corresponding protein sequence (SEQ ID NO:15)

MTPGTQSPFFLLLLLTVLTVVTGSGHASSTPGGEKETSATQRSSVPSSTEKNAVSMTSSVLSSHSPGSGSSTTQGQD

VTLAPATEPASGSAATWGQDVTSVPVTRPALGSTTPP☐*AHDVTSAPDNKPAPGSTAPP*AHGVTSAPDTRPAPGSTAPP*

***AHGVTSAPDTRPAPGSTAPP*AHGVTSAPDTRPAPGSTAPP*AHGVTSAPDTRPAPGSTAPP*☐**AHGVTSAPDNRPALGST

APPVHNVTSASGSASGSASTLVHNGTSARATTTPASKSTPFSIPSHHSDTPTTLASHSTKTDASSTHHSTVPPLTSS

NHSTSPQLSTGVSFFFLSFHISNLQFNSSLEDPSTDYYQELQRDISEMFLQIYKQGGFLGLSNIKFRPGSVVVQLTL

AFREGTINVHDVETQFNQYKTEAASRYNLTISDVSVSDVPFPFSAQSGAGVWWTSDWGVLTNLGILLLLSIAVLIAL

SCIC<u>RRKNYGQLDIFPARDTYHPMSEYPTYHTHGRYVPPSSTDRSPYEKVSAGNGGSSLSYTNPAVAATSANL</u>

Sequence Key:
BOX: Signal Peptide
ITALICS BOX BOLD BOX: Sequential Tandem Repeats
BOLD: Transmembrane Domain
UNDERLINE: Cytoplasmic Tail Align Muc1-1TR_001204285 sequence with GVX-Muc1/4TR.01 and GVX-Muc1_4TRMTm.02

```
CLUSTAL 2.1 Multiple Sequence Alignments
Sequence format is Pearson
Sequence: 1TR     475 aa (SEQ ID NO: 10)
Sequence: 4TR     535 aa (SEQ ID NO: 12)
Sequence: 4TRMtm  535 aa (SEQ ID NO: 14)

1TR      MTPGTQSPFFLLLLLTVLTVVTGSGHASSTPGGEKETSATQRSSVPSSTEKNAVSMTSSV
4TR      MTPGTQSPFFLLLLLTVLTVVTGSGHASSTPGGEKETSATQRSSVPSSTEKNAVSMTSSV
4TRMtm   MTPGTQSPFFLLLLLTVLTVVTGSGHASSTPGGEKETSATQRSSVPSSTEKNAVSMTSSV
         ************************************************************

1TR      LSSHSPGSGSSTTQGQDVTLAPATEPASGSAATWGQDVTSVPVTRPALGSTTPPAHDVTS
4TR      LSSHSPGSGSSTTQGQDVTLAPATEPASGSAATWGQDVTSVPVTRPALGSTTPPAHDVTS
4TRMtm   LSSHSPGSGSSTTQGQDVTLAPATEPASGSAATWGQDVTSVPVTRPALGSTTPPAHDVTS
         ************************************************************

1TR      APDNKPAPGSTAPPAHGVTSAPDTRPAP--------------------------------
4TR      APDNKPAPGSTAPPAHGVTSAPDTRPAPGSTAPPAHGVTSAPDTRPAPGSTAPPAHGVTS
4TRMtm   APDNKPAPGSTAPPAHGVTSAPDTRPAPGSTAPPAHGVTSAPDTRPAPGSTAPPAHGVTS
         ***************************

1TR      ---------------------------GSTAPPAHGVTSAPDNRPALGSTAPPVHNVTS
4TR      APDTRPAPGSTAPPAHGVTSAPDTRPAPGSTAPPAHGVTSAPDNRPALGSTAPPVHNVTS
4TRMtm   APDTRPAPGSTAPPAHGVTSAPDTRPAPGSTAPPAHGVTSAPDNRPALGSTAPPVHNVTS
                                    ********************************

1TR      ASGSASGSASTLVHNGTSARATTTPASKSTPFSIPSHHSDTPTTLASHSTKTDASSTHHS
4TR      ASGSASGSASTLVHNGTSARATTTPASKSTPFSIPSHHSDTPTTLASHSTKTDASSTHHS
4TRMtm   ASGSASGSASTLVHNGTSARATTTPASKSTPFSIPSHHSDTPTTLASHSTKTDASSTHHS
         ************************************************************

1TR      TVPPLTSSNHSTSPQLSTGVSFFFLSFHISNLQFNSSLEDPSTDYYQELQRDISEMFLQI
4TR      TVPPLTSSNHSTSPQLSTGVSFFFLSFHISNLQFNSSLEDPSTDYYQELQRDISEMFLQI
4TRMtm   TVPPLTSSNHSTSPQLSTGVSFFFLSFHISNLQFNSSLEDPSTDYYQELQRDISEMFLQI
         ************************************************************

1TR      YKQGGFLGLSNIKFRPGSVVVQLTLAFREGTINVHDVETQFNQYKTEAASRYNLTISDVS
4TR      YKQGGFLGLSNIKFRPGSVVVQLTLAFREGTINVHDVETQFNQYKTEAASRYNLTISDVS
4TRMtm   YKQGGFLGLSNIKFRPGSVVVQLTLAFREGTINVHDVETQFNQYKTEAASRYNLTISDVS
         ************************************************************

1TR      VSDVPFPFSAQSGAGVPGWGIALLVLVCVLVALAIVYLIALAVCQCRRKNYGQLDIFPAR
4TR      VSDVPFPFSAQSGAGVPGWGIALLVLVCVLVALAIVYLIALAVCQCRRKNYGQLDIFPAR
4TRMtm   VSDVPFPFSAQSGAGVWWTSDWGVLTNLGILLLLSIAVLIALSCICRRKNYGQLDIFPAR
         ****************      .   ::    ::  *  : ::   * **************

1TR      DTYHPMSEYPTYHTHGRYVPPSSTDRSPYEKVSAGNGGSSLSYTNPAVAATSANL
4TR      DTYHPMSEYPTYHTHGRYVPPSSTDRSPYEKVSAGNGGSSLSYTNPAVAATSANL
4TRMtm   DTYHPMSEYPTYHTHGRYVPPSSTDRSPYEKVSAGNGGSSLSYTNPAVAATSANL
         ******************************************************
```

3. Codon optimize DNA sequence for vaccinia virus
2.1. Go to the GeneArt Gene Synthesis tool in LifeTechnolgy website,
Enter GO sequence and follow the instructions.
Optimize the sequence for vaccinia virus.
Copy the optimized sequence and paste into a new SeqBuilber file.
2.2. Save the optimized sequence as well as the report.
Name the optimized sequence as: GVX-Muc1_4TRMTmVVop.03

(SEQ ID NO: 16)
ATGACACCTGGAACACAATCTCCATTTTTTCTACTACTACTATTGACAGT

ACTAACAGTAGTAACAGGATCTGGACATGCGTCTAGTACACCAGGTGGAG

AAAAAGAAACATCTGCGACTCAAAGATCTTCTGTACCATCTTCTACAGAA

AAAAATGCGGTATCTATGACATCTAGTGTACTATCTTCTCATTCTCCTGG

ATCTGGATCTTCTACTACACAAGGACAAGATGTAACACTAGCGCCAGCTA

CAGAACCAGCTTCTGGATCTGCTGCTACTTGGGGTCAAGATGTTACTTCT

GTTCCAGTAACAAGACCAGCGCTAGGATCTACAACACCACCAGCGCATGA

TGTAACAAGTGCGCCAGATAATAAACCAGCGCCTGGTTCTACTGCTCCAC

CAGCTCATGGTGTTACTTCAGCGCCTGATACAAGACCTGCACCTGGATCT

ACAGCTCCTCCTGCACATGGTGTAACATCTGCTCCAGATACAAGACCAGC

TCCAGGTTCAACAGCACCTCCAGCGCATGGTGTTACTAGTGCTCCAGATA

CAAGACCTGCGCCTGGAAGTACTGCACCACCAGCACATGGTGTAACTAGT

GCGCCTGATACAAGACCAGCGCCAGGATCAACTGCTCCTCCTGCTCATGG

TGTTACAAGTGCACCTGATAATAGACCTGCGTTGGGATCTACTGCGCCTC

CAGTTCATAATGTAACATCAGCGTCTGGAAGTGCGTCTGGTTCTGCGTCT

ACATTGGTTCATAATGGTACATCTGCGAGAGCGACAACAACTCCAGCGTC

TAAATCTACACCATTTTCTATTCCATCTCATCATTCTGATACACCAACAA

CATTGGCGAGTCATTCTACAAAAACAGATGCGAGTTCTACACATCATTCT

ACTGTACCACCACTAACATCTTCTAATCATAGTACATCTCCACAACTATC

TACTGGTGTATCTTTTTTTTTTCTATCTTTTCATATTTCTAATCTACAGT

TTAATTCTAGTTTGGAAGATCCATCTACAGATTATTATCAAGAACTACAA

AGAGATATTTCTGAAATGTTTCTACAAATATATAAACAAGGAGGATTTCT

AGGACTATCTAATATTAAGTTTAGACCAGGATCTGTAGTAGTTCAACTAA

CTCTAGCGTTTAGAGAAGGTACTATTAATGTACATGATGTTGAAACACAG

TTTAATCAATATAAAACAGAAGCGGCGTCTAGATATAATCTAACAATTTC

TGATGTATCTGTATCTGATGTTCCATTTCCATTTTCTGCGCAATCTGGTG

CTGGTGTATGGTGGACATCTGATTGGGGAGTACTAACTAATCTAGGAATT

CTACTATTGCTATCTATTGCGGTACTAATTGCGCTATCTTGTATATGTAG

AAGAAAAAATTATGGACAACTAGATATTTTTCCAGCGAGAGATACTTATC

ATCCAATGTCTGAATATCCAACATATCATACACATGGAAGATATGTACCA

CCTTCTTCAACAGATAGATCTCCATATGAAAAAGTATCTGCGGGAAATGG

TGGTTCTTCTCTATCTTATACAAATCCAGCGGTAGCGGCGACTTCTGCGA

ATCTATAA 2.3. Translate the optimized sequence (SEQ ID NO: 17)
MTPGTQSPFFLLLLLTVLTVVTGSGHASSTPGGEKETSATQRSSVPSSTE

KNAVSMTSSVLSSHSPGSGSSTTQGQDVTLAPATEPASGSAATWGQDVTS

VPVTRPALGSTTPPAHDVTSAPDNKPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDNRPALGSTAPPVHNVTSASGSASGSAS

TLVHNGTSARATTTPASKSTPFSIPSHHSDTPTTLASHSTKTDASSTHHS

TVPPLTSSNHSTSPQLSTGVSFFFLSFHISNLQFNSSLEDPSTDYYQELQ

RDISEMFLQIYKQGGFLGLSNIKFRPGSVVVQLTLAFREGTINVHDVETQ

FNQYKTEAASRYNLTISDVSVSDVPFPFSAQSGAGVWWTSDWGVLTNLGI

LLLLSIAVLIALSCICRRKNYGQLDIFPARDTYHPMSEYPTYHTHGRYVP

PSSTDRSPYEKVSAGNGGSSLSYTNPAVAATSANL

4. Interrupt homopolymer sequences (G/C or T/A rich areas) by silent mutations
Search sequence for ≥4 G/C areas:
No multiple Gs or Cs found.
Search sequence for ≥5 A/T areas:
Seven A/T rich areas have been found:
All have been interrupted by single silent mutation.
Table 2 summarizes all the mutations made on Muc1.

TABLE 2

| Muc1 Mutations | | |
|---|---|---|
| Sequence nucleotides | Silent mutation nucleotides | Mutation position in GP gene |
| TTT | TTC | 27 |
| TTT | TTC | 30 |
| GAA | GAG | 102 |
| AAA | AAG | 105 |
| GAA | GAG | 150 |
| AAA | AAG | 153 |
| AAA | AAG | 375 |
| AAA | AAG | 804 |
| TTT | TTC | 816 |
| AAA | AAG | 873 |
| TTT | TTC | 966 |
| TTT | TTC | 969 |
| TTT | TTC | 972 |
| TCT | TCC | 978 |
| TTT | TTC | 1002 |
| AAA | AAG | 1215 |
| TTT | TTC | 1284 |
| AAA | AAG | 1407 |
| TTT | TTC | 1431 |
| GAA | GAG | 1530 |
| AAA | AAG | 1633 |

Save the sequence as GVX-Muc1_4TRMTmVVop.04 (SeqBuilber file).

(SEQ ID NO: 18)
ATGACACCTGGAACACAATCTCCATTcTTcCTACTACTACTATTGACAGT

ACTAACAGTAGTAACAGGATCTGGACATGCGTCTAGTACACCAGGTGGAG

AgAAgGAAACATCTGCGACTCAAAGATCTTCTGTACCATCTTCTACAGAg

AAgAATGCGGTATCTATGACATCTAGTGTACTATCTTCTCATTCTCCTGG

-continued
```
ATCTGGATCTTCTACTACACAAGGACAAGATGTAACACTAGCGCCAGCTA
CAGAACCAGCTTCTGGATCTGCTGCTACTTGGGGTCAAGATGTTACTTCT
GTTCCAGTAACAAGACCAGCGCTAGGATCTACAACACCACCAGCGCATGA
TGTAACAAGTGCGCCAGATAATAAgCCAGCGCCTGGTTCTACTGCTCCAC
CAGCTCATGGTGTTACTTCAGCGCCTGATACAAGACCTGCACCTGGATCT
ACAGCTCCTCCTGCACATGGTGTAACATCTGCTCCAGATACAAGACCAGC
TCCAGGTTCAACAGCACCTCCAGCGCATGGTGTTACTAGTGCTCCAGATA
CAAGACCTGCGCCTGGAAGTACTGCACCACCAGCACATGGTGTAACTAGT
GCGCCTGATACAAGACCAGCGCCAGGATCAACTGCTCCTCCTGCTCATGG
TGTTACAAGTGCACCTGATAATAGACCTGCGTTGGGATCTACTGCGCCTC
CAGTTCATAATGTAACATCAGCGTCTGGAAGTGCGTCTGGTTCTGCGTCT
ACATTGGTTCATAATGGTACATCTGCGAGAGCGACAACAACTCCAGCGTC
TAAgTCTACACCATTcTCTATTCCATCTCATCATTCTGATACACCAACAA
CATTGGCGAGTCATTCTACAAAgACAGATGCGAGTTCTACACATCATTCT
ACTGTACCACCACTAACATCTTCTAATCATAGTACATCTCCACAACTATC
TACTGGTGTATCTTTcTTcTTcCTATCcTTTCATATTTCTAATCTACAGT
TcAATTCTAGTTTGGAAGATCCATCTACAGATTATTATCAAGAACTACAA
AGAGATATTTCTGAAATGTTTCTACAAATATATAAACAAGGAGGATTTCT
AGGACTATCTAATATTAAGTTTAGACCAGGATCTGTAGTAGTTCAACTAA
CTCTAGCGTTTAGAGAAGGTACTATTAATGTACATGATGTTGAAACACAG
TTTAATCAATATAAgACAGAAGCGGCGTCTAGATATAATCTAACAATTTC
TGATGTATCTGTATCTGATGTTCCATTTCCATTTTCTGCGCAATCTGGTG
CTGGTGTATGGTGGACATCTGATTGGGGAGTACTAACTAATCTAGGAATT
CTACTATTGCTATCTATTGCGGTACTAATTGCGCTATCTTGTATATGTAG
```

-continued
```
AAGAAAgAATTATGGACAACTAGATATTTTcCCAGCGAGAGATACTTATC
ATCCAATGTCTGAATATCCAACATATCATACACATGGAAGATATGTACCA
CCTTCTTCAACAGATAGATCTCCATATGAgAAgGTATCTGCGGGAAATGG
TGGTTCTTCTCTATCTTATACAAATCCAGCGGTAGCGGCGACTTCTGCGA
ATCTATAA
```

Translate GVX-Muc1_4TRMTmVVop.04:

(SEQ ID NO: 19)
MTPGTQSPFFLLLLLTVLTVVTGSGHASSTPGGEKETSATQRSSVPSSTE
KNAVSMTSSVLSSHSPGSGSSTTQGQDVTLAPATEPASGSAATWGQDVTS
VPVTRPALGSTTPPAHDVTSAPDNKPAPGSTAPPAHGVTSAPDTRPAPGS
TAPPAHGVTSAPDTRPAPGSTAPPAHGVTSAPDTRPAPGSTAPPAHGVTS
APDTRPAPGSTAPPAHGVTSAPDNRPALGSTAPPVHNVTSASGSASGSAS
TLVHNGTSARATTTPASKSTPFSIPSHHSDTPTTLASHSTKTDASSTHHS
TVPPLTSSNHSTSPQLSTGVSFFFLSFHISNLQFNSSLEDPSTDYYQELQ
RDISEMFLQIYKQGGFLGLSNIKFRPGSVVVQLTLAFREGTINVHDVETQ
FNQYKTEAASRYNLTISDVSVSDVPFPFSAQSGAGVWWTSDWGVLTNLGI
LLLLSIAVLIALSCICRRKNYGQLDIFPARDTYHPMSEYPTYHTHGRYVP
PSSTDRSPYEKVSAGNGGSSLSYTNPAVAATSANL

5. Search GP sequence for vaccinia virus transcription terminator
No TsNT motif found.
6. Add a second stop codon.
Name the optimized sequence as: GVX-Muc1_4TRMTmVVop.05
Modify the sequences of the Tandem Repeats by silent mutation (when possible), to reduce recombination and to increase the insert stability.

First Tandem Repeat (SEQ ID NO: 20)
GCT CAT GGT GTT ACT TCA GCG CCT GAT ACA AGA CCT GCA CCT GGA TCT ACA GCT CCT CCT (SEQ ID NO: 21)
A   H   G   V   T   S   A   P   D   T   R   P   A   P   G   S   T   A   P   P Second Tandem Repeat (SEQ ID NO: 22)
GCA CAT GGT GTA ACA TCT GCT CCA GAT ACA AGA CCA GCT CCA GGT TCA ACA GCA CCT CCA Third Tandem Repeat (SEQ ID NO: 23)
GCG CAT GGT GTT ACT AGT GCT CCA GAT ACA AGA CCT GCG CCT GGA AGT ACT GCA CCA CCA Forth Tandem Repeat (SEQ ID NO: 24)
GCA CAT GGT GTA ACT AGT GCG CCT GAT ACA AGA CCA GCG CCA GGA TCA ACT GCT CCT CCT (SEQ ID NO: 25)
GCT CAT GGT GTT ACT TCA GCG CCT GAT ACA AGA CCc GCA CCc GGA TCT ACc GCT CCg CCT (SEQ ID NO: 26)
GCA CAc GGc GTc ACA TCT GCT CCc GAc ACt cgt CCA GCT CCt GGT agc ACA GCA CCT CCA

```
                                                         (SEQ ID NO: 27)
GCG CAT GGa GTa ACc AGT GCa CCA GAT ACc cga CCt GCG CCg GGc AGT ACT GCc CCA CCg (SEQ ID NO: 28)
GCc CAc GGg GTg ACg AGc GCc CCg GAc ACg cgc CCA GCt CCA GGg TCA ACg GCg CCc CCT (SEQ ID NO: 21)
A   H   G   V   T   S   A   P   D   T   R   P   A   P   G   S   T   A   P   P
```

Name the optimized sequence as: GVX-Muc1_4TRMTmVVop.06

7. Add restriction sites for cloning of the Muc1 into MVA-shuttles plasmids pLW-73.
   Search GVX-Muc1_4TRMTmVVop.06 sequence for SmaI, SalI and PstI sites
   Neither of the sites is present on Muc gene, so any can be used for cloning.
   Add Sma I and Sal I restriction sites at 3' and 5' of Muc1 gene respectively.
   Sma I sequence: cccggg
   Sal I sequence: gtcgac
   Add 5 nucleotides upstream SmaI and 5 nucleotides downstream SalI to facilitate the digestion and cloning: gcgct
   Save the sequence with the cloning sites as GVX-Muc1_4TRMTmVVop.05 (SeqBuilber file).

Final sequence (SeqBuiler file) for Genscript: GVX-Muc4TRMTM (SEQ ID NO: 29)
gcgctcccgggATGACACCTGGAACACAATCTCCATTcTTcCTACTACTA
CTATTGACAGTACTAACAGTAGTAACAGGATCTGGACATGCGTCTAGTAC
ACCAGGTGGAGAgAAgGAAACATCTGCGACTCAAAGATCTTCTGTACCAT
CTTCTACAGAgAAgAATGCGGTATCTATGACATCTAGTGTACTATCTTCT
CATTCTCCTGGATCTGGATCTTCTACTACACAAGGACAAGATGTAACACT
AGCGCCAGCTACAGAACCAGCTTCTGGATCTGCTGCTACTTGGGGTCAAG
ATGTTACTTCTGTTCCAGTAACAAGACCAGCGCTAGGATCTACAACACCA
CCAGCGCATGATGTAACAAGTGCGCCAGATAATAAgCCAGCGCCTGGTTC
TACTGCTCCACCAGCTCATGGTGTTACTTCAGCGCCTGATACAAGACCTG
CACCTGGATCTACAGCTCCTCCTGCACATGGTGTAACATCTGCTCCAGAT -continued ACAAGACCAGCTCCAGGTTCAACAGCACCTCCAGCGCATGGTGTTACTAG
TGCTCCAGATACAAGACCTGCGCCTGGAAGTACTGCACCACCAGCACATG
GTGTAACTAGTGCGCCTGATACAAGACCAGCGCCAGGATCAACTGCTCCT
CCTGCTCATGGTGTTACAAGTGCACCTGATAATAGACCTGCGTTGGGATC
TACTGCGCCTCCAGTTCATAATGTAACATCAGCGTCTGGAAGTGCGTCTG
GTTCTGCGTCTACATTGGTTCATAATGGTACATCTGCGAGAGCGACAACA
ACTCCAGCGTCTAAgTCTACACCATTcTCTATTCCATCTCATCATTCTGA
TACACCAACAACATTGGCGAGTCATTCTACAAAgACAGATGCGAGTTCTA
CACATCATTCTACTGTACCACCACTAACATCTTCTAATCATAGTACATCT
CCACAACTATCTACTGGTGTATCTTTcTTcTTcCTATCcTTTCATATTTC
TAATCTACAGTTcAATTCTAGTTTGGAAGATCCATCTACAGATTATTATC
AAGAACTACAAAGAGATATTTCTGAAATGTTTCTACAAATATATAAACAA
GGAGGATTTCTAGGACTATCTAATATTAAGTTTAGACCAGGATCTGTAGT
AGTTCAACTAACTCTAGCGTTTAGAGAAGGTACTATTAATGTACATGATG
TTGAAACACAGTTTAATCAATATAAgACAGAAGCGGCGTCTAGATATAAT
CTAACAATTTCTGATGTATCTGTATCTGATGTTCCATTTCCATTcTCTGC
GCAATCTGGTGCTGGTGTATGGTGGACATCTGATTGGGGAGTACTAACTA
ATCTAGGAATTCTACTATTGCTATCTATTGCGGTACTAATTGCGCTATCT
TGTATATGTAGAAGAAAgAATTATGGACAACTAGATATTTTcCCAGCGAG
AGATACTTATCATCCAATGTCTGAATATCCAACATATCATACACATGGAA
GATATGTACCACCTTCTTCAACAGATAGATCTCCATATGAgAAgGTATCT
GCGGGAAATGGTGGTTCTTCTCTATCTTATACAAATCCAGCGGTAGCGGC
GACTTCTGCGAATCTATAATAAgtcgacgcgct Corresponding protein sequence (SEQ ID NO:30)
MTPGTQSPFFLLLLLTVLTVVTGSGHASSTPGGEKETSATQRSSVPSSTEKNAVSMTSSVLSSHSPGSGS
STTQGQDVTLAPATEPASGSAATWGQDVTSVPVTRPALGSTTPPAHDVTSAPDNKPAPGSTAPP*AHGV*
*TSAPDTRPAPGSTAPP*AHGVTSAPDTRPAPGSTAPP*AHGVTSAPDTRPAPGSTAPP*AHGVTSAPDTRP
APGSTAPPAHGVTSAPDNRPALGSTAPPVHNVTSASGSASGSASTLVHNGTSARATTTPASKSTPFSIP
SHHSDTPTTLASHSTKTDASSTHHSTVPPLTSSNHSTSPQLSTGVSFFFLSFHISNLQFNSSLEDPSTDYY
QELQRDISEMFLQIYKQGGFLGLSNIKFRPGSVVVQLTLAFREGTINVHDVETQFNQYKTEAASRYNLTIS
DVSVSDVPFPFSAQSGAGVWWTSDWGVLTNLGILLLLSIAVLIALSCICRRKNYGQLDIFPARDTYHPMS
EYPTYHTHGRYVPPSSTDRSPYEKVSAGNGGSSLSYTNPAVAATSANL.

Align final GVX-Muc4TRMTM sequence with Muc1-1TR_001204285

```
CLUSTAL 2.1 Multiple Sequence Alignments
Sequence format is Pearson
Sequence: GVX-Muc4TRMTM 535 aa (SEQ ID NO: 30)
Sequence: Muc1-1TR_001204285 475 aa (SEQ ID NO: 10)
GVX-Muc4TRMTM      MTPGTQSPFFLLLLLTVLTVVTGSGHASSTPGGEKETSATQRSSVPSSTEKNAVSMTSSV
Muc1-1TR_001204285 MTPGTQSPFFLLLLLTVLTVVTGSGHASSTPGGEKETSATQRSSVPSSTEKNAVSMTSSV
                   ************************************************************

GVX-Muc4TRMTM      LSSHSPGSGSSTTQGQDVTLAPATEPASGSAATWGQDVTSVPVTRPALGSTTPPAHDVTS
Muc1-1TR_001204285 LSSHSPGSGSSTTQGQDVTLAPATEPASGSAATWGQDVTSVPVTRPALGSTTPPAHDVTS
                   ************************************************************

GVX-Muc4TRMTM      APDNKPAPGSTAPPAHGVTSAPDTRPAPGSTAPPAHGVTSAPDTRPAPGSTAPPAHGVTS
Muc1-1TR_001204285 APDNKPAPGSTAPPAHGVTSAPDTRPAP--------------------------------
                   ****************************

GVX-Muc4TRMTM      APDTRPAPGSTAPPAHGVTSAPDTRPAPGSTAPPAHGVTSAPDNRPALGSTAPPVHNVTS
Muc1-1TR_001204285 ----------------------------GSTAPPAHGVTSAPDNRPALGSTAPPVHNVTS
                                               ********************************

GVX-Muc4TRMTM      ASGSASGSASTLVHNGTSARATTTPASKSTPFSIPSHHSDTPTTLASHSTKTDASSTHHS
Muc1-1TR_001204285 ASGSASGSASTLVHNGTSARATTTPASKSTPFSIPSHHSDTPTTLASHSTKTDASSTHHS
                   ************************************************************

GVX-Muc4TRMTM      TVPPLTSSNHSTSPQLSTGVSFFFLSFHISNLQFNSSLEDPSTDYYQELQRDISEMFLQI
Muc1-1TR_001204285 TVPPLTSSNHSTSPQLSTGVSFFFLSFHISNLQFNSSLEDPSTDYYQELQRDISEMFLQI
                   ************************************************************

GVX Muc4TRMTM      YKQGGFLGLSNIKFRPGSVVVQLTLAFREGTINVHDVETQFNQYKTEAASRYNLTISDVS
Muc1-1TR_001204285 YKQGGFLGLSNIKFRPGSVVVQLTLAFREGTINVHDVETQFNQYKTEAASRYNLTISDVS
                   ************************************************************

GVX-Muc4TRMTM      VSDVPFPFSAQSGAGVWWTSDWGVLTNLGILLLLSIAVLIALSCICRRKNYGQLDIFPAR
Muc1-1TR_001204285 VSDVPFPFSAQSGAGVPGWGIALLVLVCVLVALAIVYLIALAVCQCRRKNYGQLDIFPAR
                   ***************  .     ::    :: *  : ::    * ***************

GVX-Muc4TRMTM      DTYHPMSEYPTYHTHGRYVPPSSTDRSPYEKVSAGNGGSSLSYTNPAVAATSANL
Muc1-1TR_001204285 DTYHPMSEYPTYHTHGRYVPPSSTDRSPYEKVSAGNGGSSLSYTNPAVAATSANL
                   *******************************************************
```

Align final GVX-Muc4TRMTM sequence with GVX-Muc1_4TRMTm.01

```
CLUSTAL 2.1 Multiple Sequence Alignments
Sequence format is Pearson
Sequence: GVX-Muc4TRMTM 535 aa (SEQ ID NO: 30)
Sequence: GVX-Muc1/4TR.01 535 aa (SEQ ID NO: 12)
GVX-Muc4TRMTM    MTPGTQSPFFLLLLLTVLTVVTGSGHASSTPGGEKETSATQRSSVPSSTEKNAVSMTSSV
GVX-Muc1/4TR.01  MTPGTQSPFFLLLLLTVLTVVTGSGHASSTPGGEKETSATQRSSVPSSTEKNAVSMTSSV
                 ************************************************************

GVX-Muc4TRMTM    LSSHSPGSGSSTTQGQDVTLAPATEPASGSAATWGQDVTSVPVTRPALGSTTPPAHDVTS
GVX-Muc1/4TR.01  LSSHSPGSGSSTTQGQDVTLAPATEPASGSAATWGQDVTSVPVTRPALGSTTPPAHDVTS
                 ************************************************************

GVX-Muc4TRMTM    APDNKPAPGSTAPPAHGVTSAPDTRPAPGSTAPPAHGVTSAPDTRPAPGSTAPPAHGVTS
GVX-Muc1/4TR.01  APDNKPAPGSTAPPAHGVTSAPDTRPAPGSTAPPAHGVTSAPDTRPAPGSTAPPAHGVTS
                 ************************************************************

GVX-Muc4TRMTM    APDTRPAPGSTAPPAHGVTSAPDTRPAPGSTAPPAHGVTSAPDNRPALGSTAPPVHNVTS
GVX-Muc1/4TR.01  APDTRPAPGSTAPPAHGVTSAPDTRPAPGSTAPPAHGVTSAPDNRPALGSTAPPVHNVTS
                 ************************************************************

GVX-Muc4TRMTM    ASGSASGSASTLVHNGTSARATTTPASKSTPFSIPSHHSDTPTTLASHSTKTDASSTHHS
GVX-Muc1/4TR.01  ASGSASGSASTLVHNGTSARATTTPASKSTPFSIPSHHSDTPTTLASHSTKTDASSTHHS
                 ************************************************************
```

| | |
|---|---|
| GVX-Muc4TRMTM | TVPPLTSSNHSTSPQLSTGVSFFFLSFHISNLQFNSSLEDPSTDYYQELQRDISEMFLQI |
| GVX-Muc1/4TR.01 | TVPPLTSSNHSTSPQLSTGVSFFFLSFHISNLQFNSSLEDPSTDYYQELQRDISEMFLQI |
| | ************************************************************ |
| GVX-Muc4TRMTM | YKQGGFLGLSNIKFRPGSVVVQLTLAFREGTINVHDVETQFNQYKTEAASRYNLTISDVS |
| GVX-Muc1/4TR.01 | YKQGGFLGLSNIKFRPGSVVVQLTLAFREGTINVHDVETQFNQYKTEAASRYNLTISDVS |
| | ************************************************************ |
| GVX-Muc4TRMTM | VSDVPFPFSAQSGAGVWWTSDWGVLTNLGILLLLSIAVLIALSCICRRKNYGQLDIFPAR |
| GVX-Muc1/4TR.01 | VSDVPFPFSAQSGAGVPGWGIALLVLVCVLVALAIVYLIALAVCQCRRKNYGQLDIFPAR |
| | ***************  .   ::    ::  *  :  ::    * ************** |
| GVX-Muc4TRMTM | DTYHPMSEYPTYHTHGRYVPPSSTDRSPYEKVSAGNGGSSLSYTNPAVAATSANL |
| GVX-Muc1/4TR.01 | DTYHPMSEYPTYHTHGRYVPPSSTDRSPYEKVSAGNGGSSLSYTNPAVAATSANL |
| | ******************************************************* |

Align final GVX-Muc4TRMTM sequence with GVX-Muc1_4TRMTm.02

```
CLUSTAL 2.1 Multiple Sequence Alignments
Sequence format is Pearson
Sequence 1: GVX-Muc4TRMTM 535 aa (SEQ ID NO: 30)
Sequence 2: GVX-Muc1_4TRMTm.02 535 aa (SEQ ID NO: 15)
```

| | |
|---|---|
| GVX-Muc4TRMTM | MTPGTQSPFFLLLLLTVLTVVTGSGHASSTPGGEKETSATQRSSVPSSTEKNAVSMTSSV |
| GVX-Muc1_4TRMTm.02 | MTPGTQSPFFLLLLLTVLTVVTGSGHASSTPGGEKETSATQRSSVPSSTEKNAVSMTSSV |
| | ************************************************************ |
| GVX-Muc4TRMTM | LSSHSPGSGSSTTQGQDVTLAPATEPASGSAATWGQDVTSVPVTRPALGSTTPPAHDVTS |
| GVX-Muc1_4TRMTm.02 | LSSHSPGSGSSTTQGQDVTLAPATEPASGSAATWGQDVTSVPVTRPALGSTTPPAHDVTS |
| | ************************************************************ |
| GVX-Muc4TRMTM | APDNKPAPGSTAPP*AHGVTSAPDTRPAPGSTAPP*AHGVTSAPDTRPAPGSTAPP*AHGVTS* |
| GVX-Muc1_4TRMTm.02 | APDNKPAPGSTAPP*AHGVTSAPDTRPAPGSTAPP*AHGVTSAPDTRPAPGSTAPP*AHGVTS* |
| | ************************************************************ |
| GVX-Muc4TRMTM | *APDTRPAPGSTAPP***AHGVTSAPDTRPAPGSTAPP*AHGVTSAPDNRPALGSTAPPVHNVTS |
| GVX-Muc1_4TRMTm.02 | *APDTRPAPGSTAPP***AHGVTSAPDTRPAPGSTAPP*AHGVTSAPDNRPALGSTAPPVHNVTS |
| | ************************************************************ |
| GVX-Muc4TRMTM | ASGSASGSASTLVHNGTSARATTTPASKSTPFSIPSHHSDTPTTLASHSTKTDASSTHHS |
| GVX-Muc1_4TRMTm.02 | ASGSASGSASTLVHNGTSARATTTPASKSTPFSIPSHHSDTPTTLASHSTKTDASSTHHS |
| | ************************************************************ |
| GVX-Muc4TRMTM | TVPPLTSSNHSTSPQLSTGVSFFFLSFHISNLQFNSSLEDPSTDYYQELQRDISEMFLQI |
| GVX-Muc1_4TRMTm.02 | TVPPLTSSNHSTSPQLSTGVSFFFLSFHISNLQFNSSLEDPSTDYYQELQRDISEMFLQI |
| | ************************************************************ |
| GVX-Muc4TRMTM | YKQGGFLGLSNIKFRPGSVVVQLTLAFREGTINVHDVETQFNQYKTEAASRYNLTISDVS |
| GVX-Muc1_4TRMTm.02 | YKQGGFLGLSNIKFRPGSVVVQLTLAFREGTINVHDVETQFNQYKTEAASRYNLTISDVS |
| | ************************************************************ |
| GVX-Muc4TRMTM | VSDVPFPFSAQSGAGVWWTSDWGVLTNLGILLLLSIAVLIALSCICRRKNYGQLDIFPAR |
| GVX-Muc1_4TRMTm.02 | VSDVPFPFSAQSGAGVWWTSDWGVLTNLGILLLLSIAVLIALSCICRRKNYGQLDIFPAR |
| | ************************************************************ |
| GVX-Muc4TRMTM | DTYHPMSEYPTYHTHGRYVPPSSTDRSPYEKVSAGNGGSSLSYTNPAVAATSANL |
| GVX-Muc1_4TRMTm.02 | DTYHPMSEYPTYHTHGRYVPPSSTDRSPYEKVSAGNGGSSLSYTNPAVAATSANL |
| | ****************************************************** |

Simplify the name of GVX-Muc4TRMTM to "GVX-Muc1".
  Order synthesized gene with the GVX-Muc4TRMTM DNA sequence.
  Clone GVX-Muc4TRMTM DNA sequence into pLW-73 shuttle plasmid and rename new plasmid pGeo-Muc1 (see FIG. 1).

Example 3: MVA Vaccine Construction and In Vitro Evaluation for Hypoglycosylated Forms of MUC1

Figure 2:
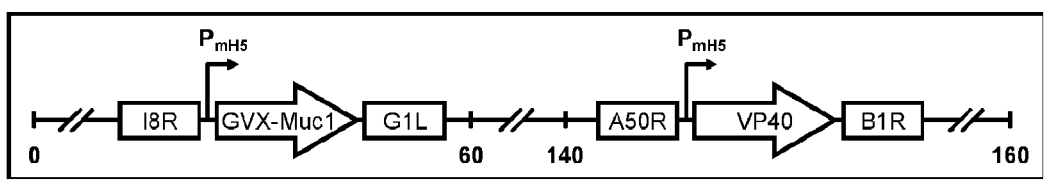
FIG. 2 is a simple line drawing illustrating the design of the MVA vectors.

The recombinant MVA vaccine consists of an MVA vector with two antigen expression cassettes (MVA-Muc1VP40). One expression cassette encodes a chimeric form of human Muc1, the construction of which is described in Example 2 above (hereafter this construction is called GVX-Muc1) and which for the purposes of MVA vaccine construction has had its DNA sequence cloned into a shuttle plasmid entitled pGeo-Muc1 (image of plasmid is seen above). One expression cassette encodes the VP40 protein of Marburgvirus. The expression of GVX-Muc1 and VP40 is sufficient to generate secreted virus-like particles (VLPs). The GVX-Muc1 protein is expressed as a chimeric protein consisting of the extracellular domain of human Muc1, the transmembrane domain of Marburgvirus GP, and the intracellular domain of human Muc1. Marburg VP40 protein is expressed in the cytoplasm of the cells where it associates with the intracellular domain and transmembrane domain of the GVX-Muc1, causing cell-surface budding of VLPs that have GVX-Muc ion their surface and VP40 enclosed in their interior (luminal) space. This novel combination of vector platform and native antigen conformation yields a vaccine that is expected to elicit a strong, broad, and durable immune response. The MVA-Muc1VP40 vaccine candidate was constructed using shuttle vectors developed in the laboratory of Dr. Bernard Moss and are being licensed by the NIAID to GeoVax for use in vaccine development. These shuttle vectors have proven to yield stable vaccine inserts with high, but non-toxic, levels of expression in our work with HIV and hemorrhagic fever virus vaccines. The Muc1 sequence was placed between two essential genes of MVA (I8R and G1L) and VP40 was inserted into a restructured and modified deletion III between the A50R and B 1R genes, illustrated in the following schematic (FIG. 2), wherein the numbers refer to coordinates in the MVA genome:

The GVX-Muc1 and VP40 genes were codon optimized for MVA. Silent mutations have been introduced to interrupt homo-polymer sequences (>4G/C and >4A/T) to reduce RNA polymerase errors that could lead to frameshifts. Inserted sequences have been edited for vaccinia-specific terminators to remove motifs that could lead to premature termination. All vaccine inserts are placed under the modified H5 early/late vaccinia promoter as described previously. Vectors were being prepared in a dedicated room under "GLP-like conditions" at GeoVax, with full traceability and complete documentation of all steps using Bovine Spongiform Encephalopathy/Transmissible Spongiform Encephalopathy (BSE/TSE)-free raw materials.

Figure 3:
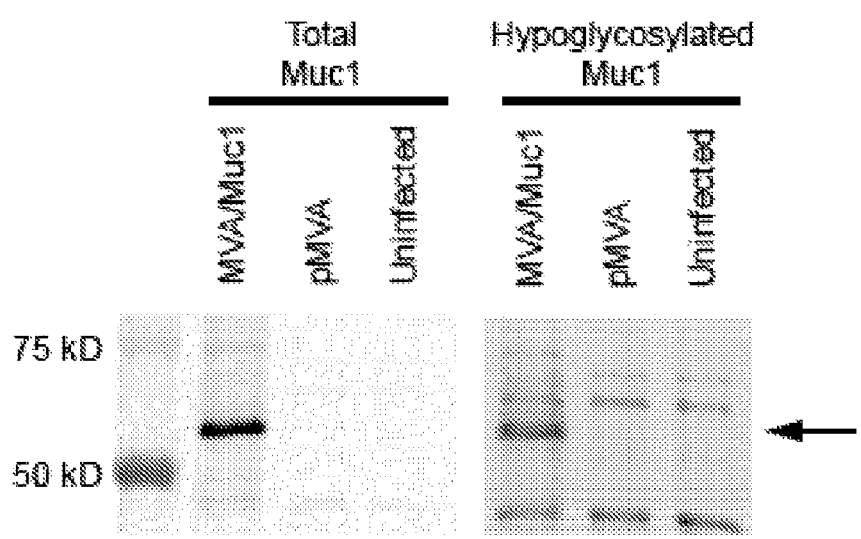
FIG. 3 is a western blot demonstrating that cells infected with the MVA-Muc1VP40 vaccine (1) express Muc1 protein, and (2) express hypoglycosylated Muc1.

The expression of full length and native conformation of GVX-Muc1 protein expressed in cells were assessed by western blotting using Muc1-specific antibodies. The MVA-Muc1VP40 vaccine was used to infect DF1 cells at a multiplicity of infection of 1.0 for 1 hour at 37° C. after which time the medium was exchanged for fresh pre-warmed medium. After 48 hours incubation at 37° C. the supernatant of the cells was harvested and clarified by centrifuging at 500×g for 10 minutes. Once the supernatant was removed from the cells, the cells themselves were harvested from the plate, washed once with cold phosphate-buffered saline (PBS) and were then lysed on ice for 15 minutes in a solution of PBS+1% Triton X-100 detergent. After this incubation, a post-nuclear supernatant was prepared by centrifuging the lysate at 1000×g for 10 minutes and harvesting the liquid layer on top, which is hereafter termed the "cell lysate". The cell lysates were applied to 10% SDS-PAGE gels and were separated by electrophoresis, then transferred to nitrocellulose membranes, blocked with Odyssey blocking buffer, then incubated with a primary antibody that recognizes either (1) the total amount of Muc1 present in the sample, or (2) the total amount of hypoglycosylated Muc1 in the sample. As control, supernatant and cell lysate from DF1 cells infected with parental MVA (a vector control containing none of the antigen expression cassettes). The results of this analysis are seen in the following image of the western blot (FIG. 3):

This demonstrates that the MVA-Muc1VP40 vaccine infects DF1 cells and expresses Muc1 protein and furthermore demonstrates that some proportion of the Muc1 expressed is in hypoglycosylated form.

Figure 4:
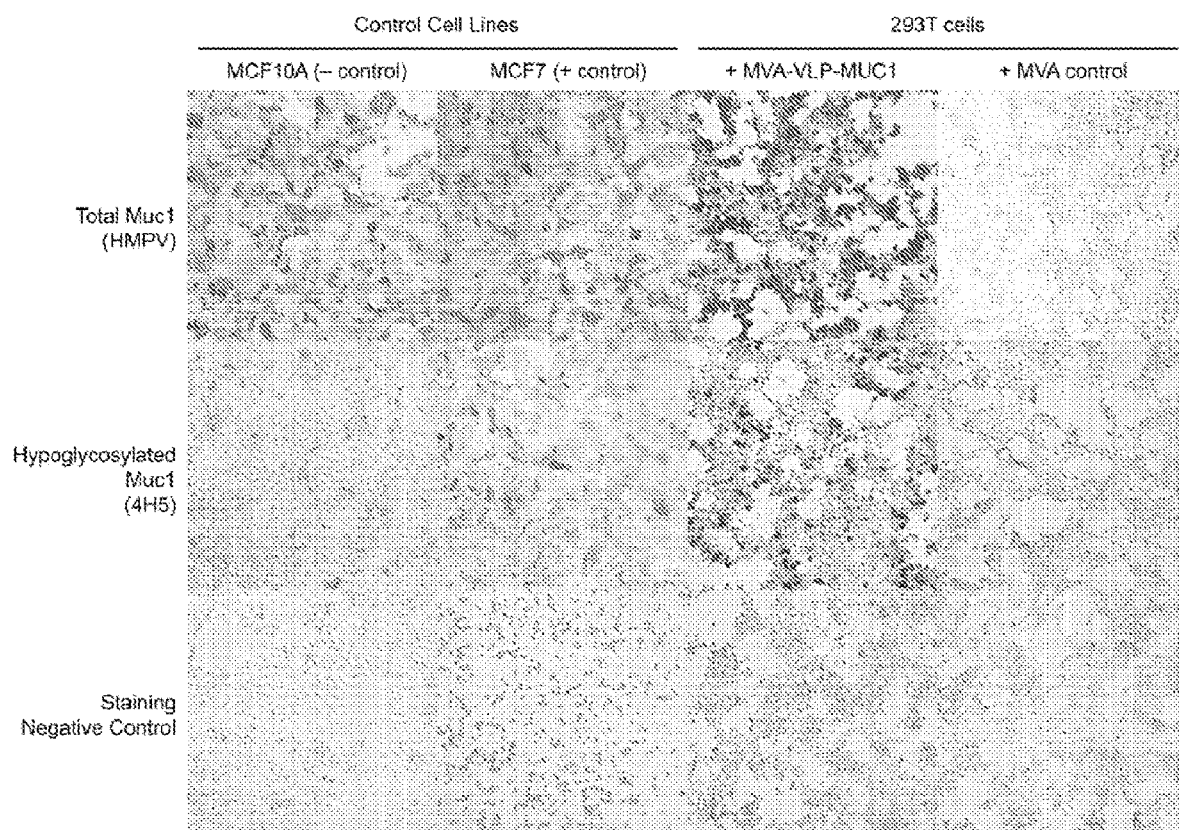
FIG. 4 is an image of cells that have been immunostained for the presence of (1) Muc1 protein, and (2) hypoglycosylated Muc1 protein. Cell samples that were so stained include negative control cells (MCF10A), positive control cells (MCF7), HEK-293T cells that have been infected with the MVA-Muc1VP40 vaccine, and HEK-293T cells that have not been infected with the MVA-Muc1VP40 vaccine.
Figure 5:
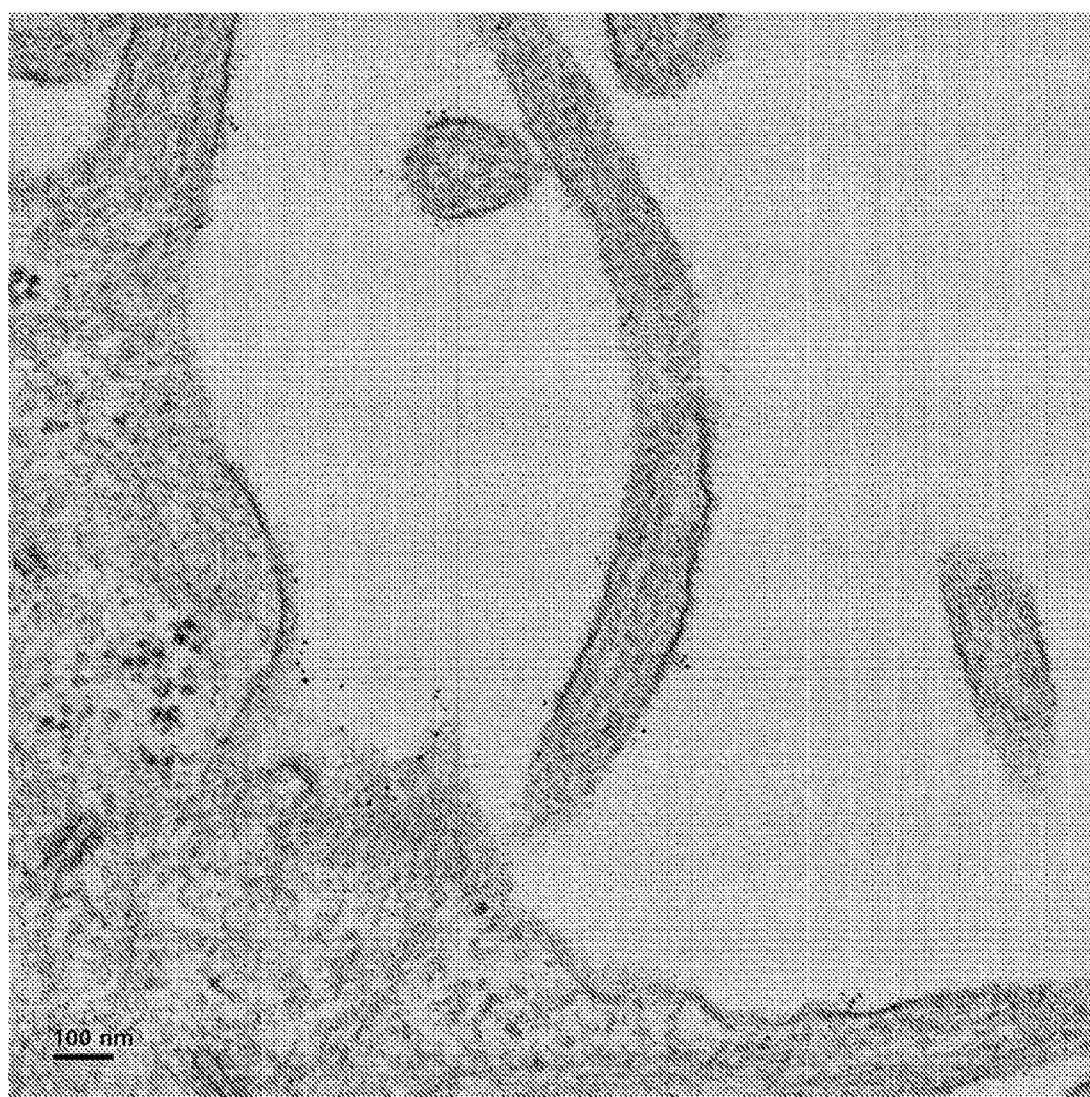
FIG. 5 is an electron micrograph showing virus-like particle (VLP) production by cells infected with MVA-Muc1VP40, an MVA vaccine encoding Muc1 TAA protein.

Evidence of the hypoglycosylated form of Muc1 encoded by the MVA-Muc1VP40 vaccine is seen by immunostaining cells infected with the vaccine or simultaneously staining control cells that are known to express either normally-glycosylated or hypo-glycosylated Muc1, as described here:
  Control cell lines MCF7 and MCF10A both express Muc1. 293T cells do not.
  MCF7 cell express hypo-glycosylated Muc1, recognized by a hypoglycosylated Muc1-specific Ab (4H5).
  MCF10A expresses normal Muc1. A pan-Muc1 Ab (HMPV) is used to detect total Muc1.
  293T cells were infected with MVA-Muc1VP40 or MVA control virus (parental MVA).
  All samples were stained with the indicated Abs.
  Note in the following image (FIG. 4) the negative signal (yellow background) in Staining Negative Control and the MVA control conditions; positive signal is reddish brown above the yellow background:

VLP formation was shown by immune-electron microscopy (EM) using of DF1 cells infected with the MVA-Muc1VP40 vaccine and stained with a monoclonal antibody that recognizes Muc1 (HMPV). In the EM image below (FIG. 5) two thing are clearly illustrated: (1) that the VLPs are filamentous, a phenomenon derivative of the fact that the VP40 protein is used as the matrix protein that drive VLP budding from the surface of cells; and (2) that the VLPs stain positively with the antibody directed against Muc1, demonstrating that this protein is incorporated into the budding VLPs.

Example 4: Targeted Diminution of O-Linked Glycosylation of Muc1

Introduction

Figure 6:
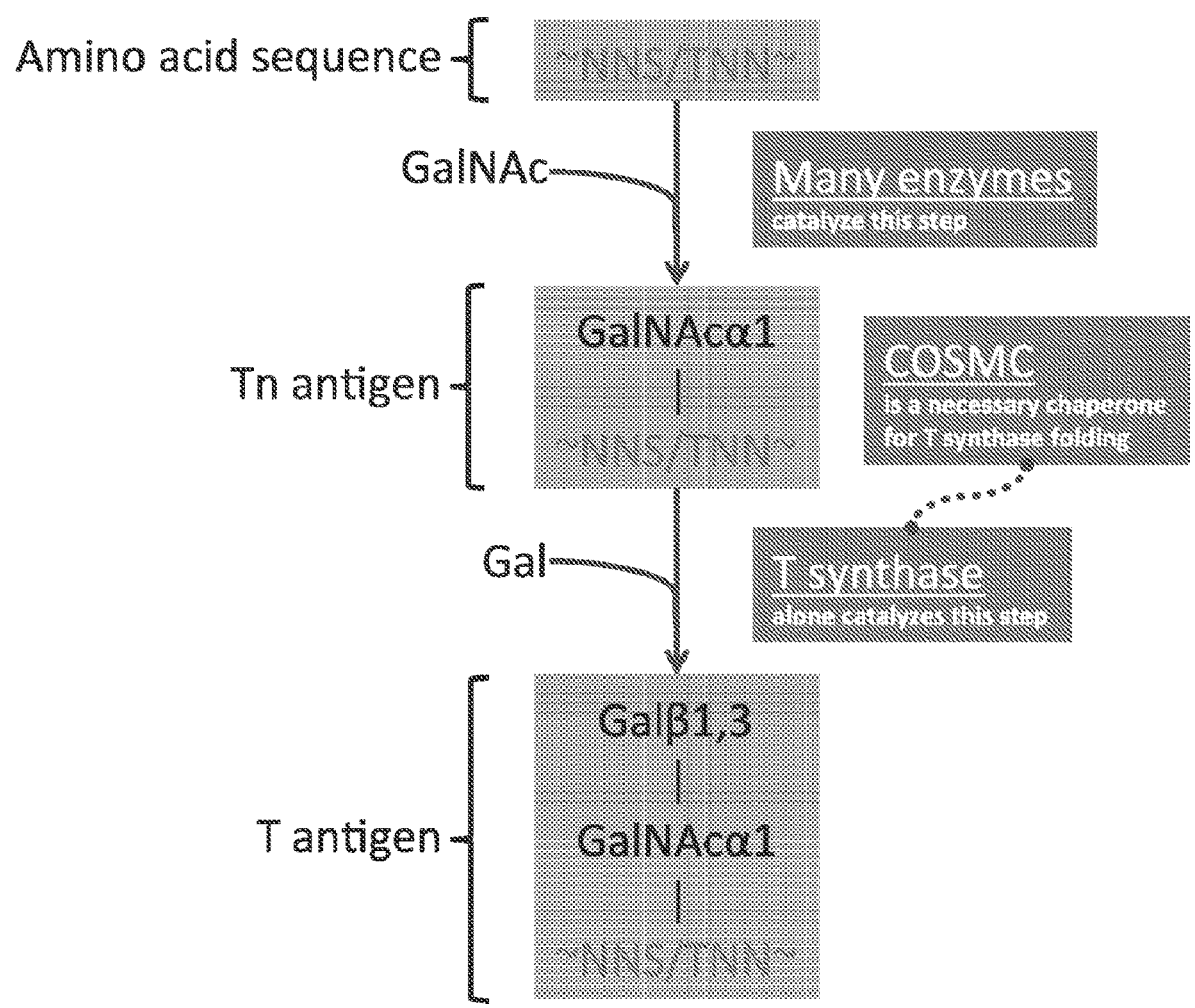
FIG. 6 provides a schematic of an initial modification pathway for the targeted diminution of O-linked glycosylation of Muc1.

Mucin-type O-glycosylation begins with modification of proteins by addition of the core 1 O-glycan Galβ3-GalNAcα1-Ser/Thr. This occurs in two steps: (1) a GalNAc is covalently attached to a Serine or Threonine of the amino acid backbone; (2) a Gal is then added to the GalNAc. An enormous variety of other glycoforms are created from this core structure by the addition of other sugars to the core 1 structure. A schematic of this initial modification pathway is as shown in FIG. 6.

Figure 7:
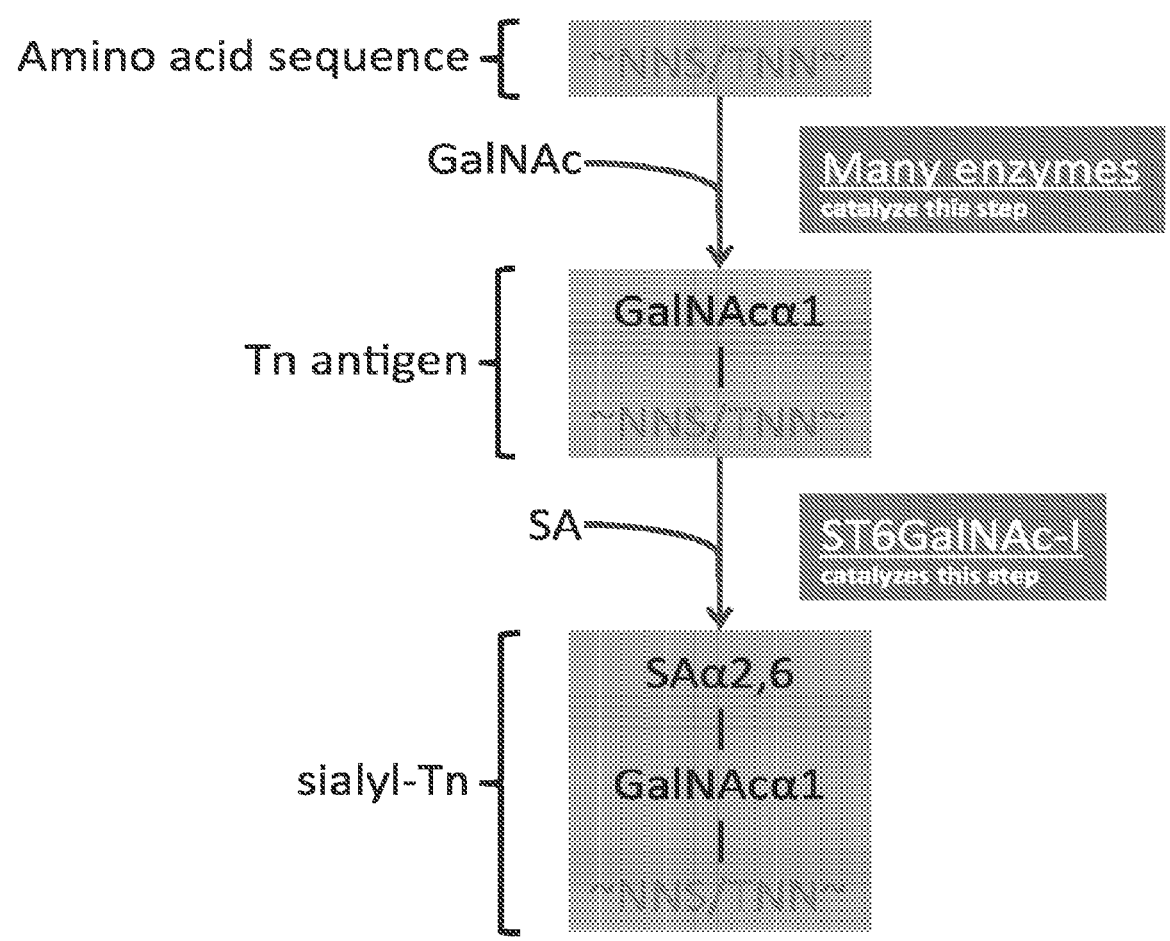
FIG. 7 provides a schematic of another initial modification pathway for the targeted diminution of O-linked glycosylation of Muc1.

This results in the formation of the T antigen carbohydrate on Ser or Thr residues of the protein backbone. Importantly, functional T synthase (also known as core 1 β3-galactosyl transferase, gene symbol C1GALT1) is the only known enzyme responsible for formation of the T antigen from the Tn antigen. Subsequent further modifications of the core 1 carbohydrate structure are completely dependent upon the formation of T antigen. In the absence of T synthase, therefore, O-linked glycosylation that depends on the core 1 structure ceases with the formation of Tn antigen (see Aryal, R. P., Ju, T. & Cummings, R. D., J Biol Chem 289, 11630-11641 (2014)). As a caveat, an additional mechanism for hypoglycosylation involves the addition of a sialic acid onto Tn by α-2,6-sialyl transferase I (gene symbol ST6GALNAC1), resulting in a terminal (non-extendable) sialyl-Tn structure (Siaα2-6GalNAcα1-Ser/Thr), illustrated as shown in FIG. 7.

The goal is to ensure endogenous in vivo production of hypoglycosylated Muc1. While overexpression of Muc1 in cells is likely to overwhelm the glycosylation machinery of many cells, it may be amenable to our purposes to additionally push the biosynthetic pathway toward hypoglycosylation of Muc1 by tampering with the glycosylation machinery. Muc1 structures that terminate O-linked glycosylation with the Tn antigen and sialyl-Tn are predominant species among the known hypoglycosylated forms that are associated with a number of carcinomas. Given what is known about the O-linked glycosylation synthesis pathway, two readily recognizable mechanisms can be envisioned for driving endogenous hypoglycosylation of Muc1:

(1) Prevent the formation of T antigen and promote the abundance of Tn antigen by knocking down the expression of functional T synthase. This can be done by either:

a. Directly targeting transcripts of the T synthase gene by siRNA methods; or

Targeting transcripts of COSMC (gene symbol C1GALT1C1) by siRNA methods, as COSMC is known to be essential and specific for the folding and function of T synthase in the ER, and mutations in this X-linked gene have been associated in humans with Tn syndrome.

(2) Over-express α-2,6-sialyl transferase I (gene symbol ST6GALNAC1, herein abbreviated as 'ST1') to terminate O-linked glycosylation with sialyl-Tn.

Methods

Summary data on the three genes of interest are provided as follows:

T synthase (C1GALT1)

The C1GALT1 gene is 66,104 nt long, composed of 6 exons, and located at human chromosome 7p21.3. This is transcribed and spliced to yield a 6244 nt long mRNA (NM_020156). A start codon is located at nt 224 of the mRNA and the CDS spans 1092 nt from 224 . . . 1315, yielding a 363 amino acid protein (NP_064541) with a calculated molecular weight of 42 kD. Amino acid residues 7 . . . 29 are predicted to encode a transmembrane domain and the ectodomain of the protein is known to reside in the lumen of the ER, indicating that T synthase is a single pass Type II membrane protein.

COSMC (T synthase-specific chaperone; C1GALT1C1)

The C1GALT1C1 gene is 4476 nt long, composed of 3 exons, and located on the human X chromosome at Xq24. This is transcribed and spliced to yield a 1915 nt long mRNA (NM_152692). A start codon is located at nt 412 of the mRNA and the CDS spans 957 nt from 412 . . . 1368, yielding a 318 amino acid protein (NP_689905) with a calculated molecular weight of 36 kD. Amino acid residues 7 . . . 26 are predicted to encode a transmembrane domain and the ectodomain of the protein is known to reside in the lumen of the ER, indicating that COSMC is a single pass Type II membrane protein.

ST1 (α-2,6-sialyl transferase I; ST6GALNAC1)

The ST6GALNAC1 gene is 26,064 nt long, composed of 12 exons, and located at human chromosome 17q25.1. This is transcribed and spliced to yield a 2593 nt long mRNA (NM_018414). A start codon is located at nt 201 of the mRNA and the CDS spans 1803 nt from 201 . . . 2003, yielding a 600 amino acid protein (NP_060884) with a calculated molecular weight of 68 kD. Amino acid residues 15 . . . 35 are predicted to encode a transmembrane domain and the ectodomain of the protein is known to be exposed to the lumen of the ER upon translocation, indicating that ST1 is a single pass Type II membrane protein.

Established methods for siRNA design, to be applied to the human T synthase and COSMC genes, are as follows:

1. Find 21 nt sequences in the target mRNA that begin with an AA dinucleotide.

2. Select 2-4 target sequences, with the following parameters:

siRNAs with 30-50% GC content are more active than those with a higher G/C content.

Since a 4-6 nucleotide poly(T) tract acts as a termination signal for RNA pol III, avoid stretches of >4 T's or A's in the target sequence when designing sequences to be expressed from an RNA pol III promoter.

Since some regions of mRNA may be either highly structured or bound by regulatory proteins, select siRNA target sites at different positions along the length of the gene sequence. No correlation has been observed between the position of target sites on the mRNA and siRNA potency.

Compare the potential target sites to the appropriate genome database (human, mouse, rat, etc.) and eliminate from consideration any target sequences with more than 16-17 contiguous base pairs of homology to other coding sequences.

3. Design appropriate controls.

A negative control siRNA with the same nucleotide composition as the siRNA but which lacks significant sequence homology to the genome. Scramble the nucleotide sequence of the gene-specific siRNA and conduct a search to make sure it lacks homology to any other gene.

Additional siRNA sequences targeting the same mRNA. Perform experiments, using a single siRNA at a time, with two or more different siRNAs targeting the same gene.

MVA-driven expression of the ST1 should be straightforward, as the CDS for this gene product is only ~1800 nt in length.

Cell Lines

HEK-293T cells are known to be negative for expression of Muc1 (see Mehanta, et al, PLoS ONE, 2008). T47D cells (derived from human mammary gland carcinoma) endogenously express Muc1, are grown in standard medium (RPMI), and are transfectable. These cells have been used for Muc1 knockdown (KD) studies in the abovementioned publication and may be amenable to our research/early characterization studies of Muc1 hypoglycosylation. T47D cells are available from ATCC (Cat. No. HTB-133) for $431. Olja Finn mentioned that there is a series of cell lines based on the MCF-7 line that are useful for carcinoma studies. In particular she recommended MCF-10A in this series, as it is known to express high levels of fully-glycosylated Muc1 (see also Olja's paper: Cascio, et al, J Biol Chem, 2011). MCF-10A is a transformed, non-tumorigenic adherent epithelial cell line derived from the mammary gland of a 36-year old Caucasian female with fibrocystic disease. The cell line is suitable as a transfection host, according to ATCC, where the cell line is available for $431 (Cat. No. CRL-10317). This cell line uses Mammalian Epithelial Cell Growth Medium (MEGM) from Lonza, supplemented with the Lonza MEGM Bullet Kit (without the gentamicin/amphotericin-B supplement) and 100 ng/ml cholera toxin (Sigma).

Transient Expression Constructs

In looking at the products available for gene manipulation from Origene (www.origene.com), it was found that they provide both vetted RNAi reagents in ready-to-use formats, as well as vetted ORFs in ready-to-use plasmids. For RNAi methods, the two most appropriate reagents for our purposes would be either synthetic siRNA duplexes, or shRNA constructs that can be expressed from a plasmid. Since, with any success, we would be aiming to express the RNAi products from the MVA vector itself, it would be most amenable to these ends to work with shRNA, which should be easily transferred over to an MVA expression system. Origen offers shRNA products in a number of different formats, but we would want a simple expression vector that is selectable for prepping plasmids (Kan(r) and Cam(r) are offered) and reportable (GFP and RFP are offered). Thus we will order shRNA constructs targeting C1GALT1 (in plasmid pGFP-V-RS, with GFP reporter: Cat. No. TG306064) and C1GALT1C1 (in plasmid pRFP-C-RS, with RFP reporter: Cat. No. TF317130). Both plasmids drive shRNA transcription with a U6 promoter. Maps for these plasmids are shown below.

The abovementioned shRNA products are provided with 4 shRNAs each. Each shRNA will be independently tested for KD. They have target sequences and mRNA coordinates as follows.

Origene shRNA products targeting C1GALT1 (T synthase), with mRNA coordinates (NM_020156):

| Product | SEQ ID NO: | Sequence | Coordinates (mRNA) |
|---|---|---|---|
| TG306064A | 31 | TATGAATGTAGAAGCAGGAGATTCCAGAG | 970-998 |
| TG306064B | 32 | TGGTACTGGAATTACAACTATTATCCTCC | 1076-1104 |
| TG306064C | 33 | CCAAAGAAGGCAGAGATCAACTATACTGG | 630-658 |
| TG306064D | 34 | ACACATAGTTCCTCCATTGAAGACTTAGC | 920-948 |

Origene shRNA products targeting C1GALT1C1 (COSMC), with mRNA coordinates (NM_152692):

| Product | SEQ ID NO: | Sequence | Coordinates (mRNA) |
|---|---|---|---|
| TF317130A | 35 | TAGGATTGGTCATGGAAATAGAATGCACC | 495-523 |
| TF317130B | 36 | AAGGAGACTTGGACCAAACACTGTGACAA | 670-698 |
| TF317130C | 37 | GCAGTTTGCCTGAAATATGCTGGAGTATT | 1081-1109 |
| TF317130D | 38 | CTTACCTCCAAATGGTTCTGACAATGACT | 1338-1366 |

KD of these gene products can be assessed by either RT-PCR or WB.

For driving expression of ST1, a construct is readily available from Origene. The product of interest (Cat. No. RC216697) contains the full-length ST6GALNAC1 gene, driven by the CMV promoter, and tagged on the C-terminal with Myc and DDK (FLAG) tags, all in the Origene pCMV6-Entry vector (see RC216687 below).

Experimental Plan

1. Preliminary Experiments

Make whole cell lysates (WCL) of HEK293T or HeLa cells. Use WCL to optimize WB methods for detection of T-synthase (with rb pAb) and COSMC (with ms mAb). Use anti-ms IR700 dye and anti-rb IR800 dye as secondaries, to allow subsequent simultaneous detection of the two antigens on the same WB and such simultaneous detection will be important when assaying the effects of shRNA KD of transcripts.

Set up and bank MCF 10A cells.

Transfect MCF 10A cells with innocuous GFP-encoding plasmid to determine basal level of transfection efficiency.

Make MCF 10A WCL. Test for expression levels of T-synthase and COSMC by WB.

Test anti-Muc1 Abs for WB and flow cytometry using MCF10A cells.

2. Pivotal Experiments shRNA KD of T-Synthase in MCF10A Cells

Transfect MCF10A cells individually with each of the 4 shRNA plasmids targeting T-synthase.

Make WCL of each transfected population at prescribed time points. Analyze WCL for expression of T-synthase, COSMC, Muc1, and hypoglycosylated Muc1 (hgMuc1).

Select shRNA that yields the best KD response.

Transfect MCF10A cells with optimal shRNA. Use flow cytometry to analyze cells for surface expression of Muc1 and hgMuc1.

shRNA KD of COSMC in MCF10A Cells

Transfect MCF10A cells individually with each of the 4 shRNA plasmids targeting COSMC.

Make WCL of each transfected population at prescribed time points. Analyze WCL for expression of T-synthase, COSMC, Muc1, and hypoglycosylated Muc1 (hgMuc1).

Select shRNA that yields the best KD response.

Transfect MCF10A cells with optimal shRNA. Use flow cytometry to analyze cells for surface expression of Muc1 and hgMuc1.

2. Pivotal Experiments (Continued)

Ectopic expression of ST1 (ST6GALNAC1 sialyl transferase) in MCF10A cells.

Transfect MCF 10A cells with RC216697 plasmid encoding ST1 behind a CMV promoter.

Assess viability and make WCL of transfected cells at prescribed time points. Analyze WCL for expression of ST1 (detected by anti-DDK antibody), Muc1, and hypoglycosylated Muc1 (hgMuc1).

Transfect MCF 10A cells with RC216697 plasmid. Use flow cytometry to analyze cells for surface expression of Muc1 and hgMuc1.

In light of results from the pivotal experiments above, determine whether to proceed with one of the single approaches investigated, or to attempt combining approaches. One could conceive, for instance of attempting a double-KD of both T-synthase and COSMC by shRNA if neither individually yielded sufficient results, or to co-transfect either shRNA along with the RC216697 plasmid driving expression of ST1.

If ST1 will be used, proceed with having this gene synthesized in vaccinia codon-optimized form.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference in their entirety.

We claim:

1. A recombinant modified vaccinia Ankara (MVA) viral vector comprising:
   (i) a first heterologous nucleic acid sequence encoding a chimeric protein comprising (a) a mucin-1 (MUC-1) antigenic peptide and (b) a transmembrane domain of a viral glycoprotein (GP) of Marburg virus, wherein the first heterologous nucleic acid sequence encodes an amino acid sequence comprising the amino acid sequence of SEQ ID NO: 15, or an amino acid sequence 98% identical thereto, and
   (ii) a second heterologous nucleic acid sequence encoding a viral Marburg virus VP40 matrix protein;
   wherein the first heterologous nucleic acid sequence and second heterologous nucleic acid sequence are under the control of one or more promoters compatible with poxvirus expression systems, and wherein upon expression, the chimeric protein and VP40 matrix protein are capable of assembling together to form virus like particles (VLPs).

2. The recombinant MVA viral vector of claim 1, wherein the promoter is selected from the group consisting of Pm2H5, Psyn II, and PmH5, or combinations thereof.

3. The recombinant MVA viral vector of claim 1, wherein the first heterologous nucleic acid sequence-encodes an amino acid sequence comprising the amino acid sequence of SEQ ID NO:15.

4. The recombinant MVA viral vector of claim 2, wherein the first heterologous nucleic acid sequence is under the control of the PmH5 promoter.

5. The recombinant MVA viral vector of claim 2, wherein the second heterologous nucleic acid sequence is under the control of the PmH5 promoter.

6. The recombinant MVA of claim 1, wherein the first heterologous nucleic acid sequence is inserted between essential genes of MVA I8R and G1L.

7. The recombinant MVA of claim 1, wherein the second heterologous nucleic acid sequence is inserted in restructured and modified MVA deletion III region between MVA genes A50R and B1R.

8. The recombinant MVA viral vector of claim 1, wherein the first heterologous nucleic acid sequence comprises the nucleic acid sequence of SEQ ID NO: 16, or a nucleic acid sequence at least 95% identical thereto.

9. The recombinant MVA viral vector of claim 8, wherein the first heterologous nucleic acid sequence comprises the nucleic acid sequence of SEQ ID NO: 16.

10. The recombinant MVA viral vector of claim 1, wherein the first heterologous nucleic acid sequence comprises the nucleic acid sequence of SEQ ID NO: 18, or a nucleic acid sequence at least 95% identical thereto.

11. The recombinant MVA viral vector of claim 10, wherein the first heterologous nucleic acid sequence comprises the nucleic acid sequence of SEQ ID NO: 18.

12. The recombinant MVA viral vector of claim 1, wherein the first heterologous nucleic acid sequence comprises the nucleic acid sequence of SEQ ID NO: 29, or a nucleic acid sequence at least 95% identical thereto.

13. The recombinant MVA viral vector of claim 12, wherein the first heterologous nucleic acid sequence comprises the nucleic acid sequence of SEQ ID NO: 29.

14. A recombinant MVA viral vector comprising:
   (i) a first heterologous nucleic acid sequence comprising the nucleic acid sequence of SEQ ID NO:29 encoding a chimeric protein comprising the amino acid sequence of SEQ ID NO: 15, and (ii) a second heterologous nucleic acid sequence encoding a viral Marburg virus VP40 matrix protein;
wherein the first heterologous nucleic acid sequence and second heterologous nucleic acid sequence are under the control of a PmH5 promoter;
wherein the first heterologous nucleic acid sequence is inserted between essential genes of MVA I8R and G1L;
wherein the second heterologous nucleic acid sequence is inserted in restructured and modified MVA deletion III region between MVA genes A50R and B1R; and,
wherein upon expression, the chimeric protein and VP40 matrix protein are capable of assembling together to form VLPs.

* * * * *

```
                              SEQUENCE LISTING

<160> NUMBER OF SEQ ID NOS: 38

<210> SEQ ID NO 1
<211> LENGTH: 20
<212> TYPE: PRT
<213> ORGANISM: Homo sapiens

<400> SEQUENCE: 1

Ala His Gly Val Thr Ser Ala Pro Asp Thr Arg Pro Ala Pro Gly Ser
1               5                   10                  15

Thr Ala Pro Pro
            20

<210> SEQ ID NO 2
<211> LENGTH: 20
<212> TYPE: PRT
<213> ORGANISM: Homo sapiens

<400> SEQUENCE: 2

Ala His Gly Val Thr Ser Ala Pro Asp Asn Arg Pro Ala Leu Gly Ser
1               5                   10                  15

Thr Ala Pro Pro
            20

<210> SEQ ID NO 3
<211> LENGTH: 40
<212> TYPE: PRT
<213> ORGANISM: Homo sapiens

<400> SEQUENCE: 3

Ala His Gly Val Thr Ser Ala Pro Asp Thr Arg Pro Ala Pro Gly Ser
1               5                   10                  15

Thr Ala Pro Pro Ala His Gly Val Thr Ser Ala Pro Asp Asn Arg Pro
            20                  25                  30

Ala Leu Gly Ser Thr Ala Pro Pro
        35                  40

<210> SEQ ID NO 4
<211> LENGTH: 100
<212> TYPE: PRT
<213> ORGANISM: Homo sapiens

<400> SEQUENCE: 4

Ala His Gly Val Thr Ser Ala Pro Asp Thr Arg Pro Ala Pro Gly Ser
1               5                   10                  15
```

```
                Thr Ala Pro Pro Ala His Gly Val Thr Ser Ala Pro Asp Thr Arg Pro
                         20                  25                  30

Ala Pro Gly Ser Thr Ala Pro Pro Ala His Gly Val Thr Ser Ala Pro
                     35                  40                  45

Asp Thr Arg Pro Ala Pro Gly Ser Thr Ala Pro Pro Ala His Gly Val
                     50                  55                  60

Thr Ser Ala Pro Asp Thr Arg Pro Ala Pro Gly Ser Thr Ala Pro Pro
                65                  70                  75                  80

Ala His Gly Val Thr Ser Ala Pro Asp Asn Arg Pro Ala Leu Gly Ser
                                 85                  90                  95

Thr Ala Pro Pro
                        100

<210> SEQ ID NO 5
<211> LENGTH: 1428
<212> TYPE: DNA
<213> ORGANISM: Homo sapiens

<400> SEQUENCE: 5
atgacaccgg gcacccagtc tcctttcttc ctgctgctgc tcctcacagt gcttacagtt        60
gttacgggtt ctggtcatgc aagctctacc ccaggtggag aaaaggagac ttcggctacc       120
cagagaagtt cagtgcccag ctctactgag aagaatgctg tgagtatgac cagcagcgta       180
ctctccagcc acagccccgg ttcaggctcc tccaccactc agggacagga tgtcactctg       240
gccccggcca cggaaccagc ttcaggttca gctgccacct ggggacagga tgtcacctcg       300
gtcccagtca ccaggccagc cctgggctcc accacccgc cagcccacga tgtcacctca       360
gccccggaca caagccagc cccgggctcc accgccccc cagcccacgg tgtcacctcg       420
gccccggaca ccaggccggc cccgggctcc accgccccc cagcccatgg tgtcacctcg       480
gccccggaca caggccgc cttgggctcc accgcccctc cagtccacaa tgtcacctcg       540
gcctcaggct ctgcatcagg tcagcttct actctggtgc acaacggcac ctctgccagg       600
gctaccacaa ccccagccag caagagcact ccattctcaa ttcccagcca ccactctgat       660
actcctacca cccttgccag ccatagcacc aagactgatg ccagtagcac tcaccatagc       720
acggtacctc ctctcacctc ctccaatcac agcacttctc cccagttgtc tactggggtc       780
tctttctttt tcctgtctt tcacattcca acctccagt ttaattcctc tctgaagat       840 cccagcaccg actactacca agagctgcag agagacattt ctgaaatgtt tttgcagatt       900
tataaacaag ggggtttcct gggcctctcc aatattagt tcaggccagg atctgtggtg       960
gtacaattga ctctggcctt ccgagaaggt accatcaatg tccacgacgt ggagacacag      1020
ttcaatcagt ataaaacgga agcagcctct cgatataacc tgacgatctc agacgtcagc      1080
gtgagtgatg tgccatttcc tttctctgcc cagtctgggg ctggggtgcc aggctgggc      1140 atcgcgctgc tggtgctggt ctgtgttctg gttgcgctgg ccattgtcta tctcattgcc      1200
ttggctgtct gtcagtgccg ccgaaagaac tacgggcagc tggacatctt ccagcccgg      1260 gatacctacc atcctatgag cgagtacccc acctaccaca cccatgggcg ctatgtgccc      1320
cctagcagta ccgatcgtag ccctatgag aaggttctg caggtaatgg tggcagcagc      1380
ctctcttaca caaacccagc agtggcagcc acttctgcca acttgtag                  1428

<210> SEQ ID NO 6
<211> LENGTH: 475
<212> TYPE: PRT
```

<213> ORGANISM: Homo sapiens

<400> SEQUENCE: 6

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
130                 135                 140

Arg Pro Ala Pro Gly Ser Thr Ala Pro Pro Ala His Gly Val Thr Ser
145                 150                 155                 160

Ala Pro Asp Asn Arg Pro Ala Leu Gly Ser Thr Ala Pro Pro Val His
                165                 170                 175

Asn Val Thr Ser Ala Ser Gly Ser Ala Ser Gly Ser Ala Ser Thr Leu
            180                 185                 190

Val His Asn Gly Thr Ser Ala Arg Ala Thr Thr Thr Pro Ala Ser Lys
        195                 200                 205

Ser Thr Pro Phe Ser Ile Pro Ser His His Ser Asp Thr Pro Thr Thr
210                 215                 220

Leu Ala Ser His Ser Thr Lys Thr Asp Ala Ser Ser Thr His His Ser
225                 230                 235                 240

Thr Val Pro Pro Leu Thr Ser Ser Asn His Ser Thr Ser Pro Gln Leu
                245                 250                 255

Ser Thr Gly Val Ser Phe Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Phe Leu Gln Ile Tyr Lys Gln Gly
290                 295                 300

Gly Phe Leu Gly Leu Ser Asn Ile Lys Phe Arg Pro Gly Ser Val Val
305                 310                 315                 320

Val Gln Leu Thr Leu Ala Phe Arg Glu Gly Thr Ile Asn Val His Asp
                325                 330                 335

Val Glu Thr Gln Phe Asn Gln Tyr Lys Thr Glu Ala Ala Ser Arg Tyr
            340                 345                 350

Asn Leu Thr Ile Ser Asp Val Ser Val Ser Asp Val Pro Phe Pro Phe
        355                 360                 365

Ser Ala Gln Ser Gly Ala Gly Val Pro Gly Trp Gly Ile Ala Leu Leu
370                 375                 380

Val Leu Val Cys Val Leu Val Ala Leu Ala Ile Val Tyr Leu Ile Ala
385                 390                 395                 400
```

| Leu | Ala | Val | Cys | Gln | Cys | Arg | Arg | Lys | Asn | Tyr | Gly | Gln | Leu | Asp | Ile |
|---|---|---|---|---|---|---|---|---|---|---|---|---|---|---|---|
| | | | | 405 | | | | 410 | | | | | 415 | | |

| Phe | Pro | Ala | Arg | Asp | Thr | Tyr | His | Pro | Met | Ser | Glu | Tyr | Pro | Thr | Tyr |
|---|---|---|---|---|---|---|---|---|---|---|---|---|---|---|---|
| | 420 | | | | | | 425 | | | | | 430 | | | |

| His | Thr | His | Gly | Arg | Tyr | Val | Pro | Pro | Ser | Ser | Thr | Asp | Arg | Ser | Pro |
|---|---|---|---|---|---|---|---|---|---|---|---|---|---|---|---|
| | | 435 | | | | | 440 | | | | | 445 | | | |

| Tyr | Glu | Lys | Val | Ser | Ala | Gly | Asn | Gly | Gly | Ser | Ser | Leu | Ser | Tyr | Thr |
|---|---|---|---|---|---|---|---|---|---|---|---|---|---|---|---|
| 450 | | | | | 455 | | | | | 460 | | | | | |

| Asn | Pro | Ala | Val | Ala | Ala | Thr | Ser | Ala | Asn | Leu |
|---|---|---|---|---|---|---|---|---|---|---|
| 465 | | | | 470 | | | | 475 | | |

<210> SEQ ID NO 7
<211> LENGTH: 1608
<212> TYPE: DNA
<213> ORGANISM: Homo sapiens

<400> SEQUENCE: 7

| atgacaccgg | gcacccagtc | tcctttcttc | ctgctgctgc | tcctcacagt | gcttacagtt | 60 |
|---|---|---|---|---|---|---|
| gttacgggtt | ctggtcatgc | aagctctacc | ccaggtggag | aaaaggagac | ttcggctacc | 120 |
| cagagaagtt | cagtgcccag | ctctactgag | aagaatgctg | tgagtatgac | cagcagcgta | 180 |
| ctctccagcc | acagccccgg | ttcaggctcc | tccaccactc | agggacagga | tgtcactctg | 240 |
| gccccggcca | cggaaccagc | ttcaggttca | gctgccacct | ggggacagga | tgtcacctcg | 300 |
| gtcccagtca | ccaggccagc | cctgggctcc | accacccgc | cagcccacga | tgtcacctca | 360 |
| gccccggaca | caagccagc | cccgggctcc | accgccccc | cagcccacgg | tgtcacctcg | 420 |
| gccccggaca | ccaggccggc | cccgggctcc | accgccccc | cagcccacgg | tgtcacctcg | 480 |
| gccccggaca | ccaggccggc | cccgggctcc | accgccccc | cagcccacgg | tgtcacctcg | 540 |
| gccccggaca | ccaggccggc | cccgggctcc | accgccccc | cagcccacgg | tgtcacctcg | 600 |
| gccccggaca | ccaggccggc | cccgggctcc | accgccccc | cagcccatgg | tgtcacctcg | 660 |
| gccccggaca | caggcccgc | cttgggctcc | accgcccctc | cagtccacaa | tgtcacctcg | 720 |
| gcctcaggct | ctgcatcagg | ctcagcttct | actctggtgc | acaacggcac | ctctgccagg | 780 |
| gctaccacaa | ccccagccag | caagagcact | ccattctcaa | ttcccagcca | ccactctgat | 840 |
| actcctacca | cccttgccag | ccatagcacc | aagactgatg | ccagtagcac | tcaccatagc | 900 |
| acggtacctc | ctctcacctc | ctccaatcac | agcacttctc | cccagttgtc | tactggggtc | 960 |
| tctttcttt | tcctgtctt | tcacatttca | aacctccagt | ttaattcctc | tctggaagat | 1020 |
| cccagcaccg | actactacca | agagctgcag | agagacattt | ctgaaatgtt | tttgcagatt | 1080 |
| tataaacaag | ggggttttct | gggcctctcc | aatattaagt | tcaggccagg | atctgtggtg | 1140 |
| gtacaattga | ctctggcctt | ccgagaaggt | accatcaatg | tccacgacgt | ggagacacag | 1200 |
| ttcaatcagt | ataaaacgga | agcagcctct | cgatataacc | tgacgatctc | agacgtcagc | 1260 |
| gtgagtgatg | tgccatttcc | tttctctgcc | cagtctgggg | ctggggtgcc | aggctgggc | 1320 |
| atcgcgctgc | tggtgctggt | ctgtgttctg | gttgcgctgg | ccattgtcta | tctcattgcc | 1380 |
| ttggctgtct | gtcagtgccg | ccgaaagaac | tacgggcagc | tggacatctt | tccagcccgg | 1440 |
| gatacctacc | atcctatgag | cgagtacccc | acctaccaca | cccatgggcg | ctatgtgccc | 1500 |
| cctagcagta | ccgatcgtag | ccctatgag | aaggtttctg | caggtaatgg | tggcagcagc | 1560 |
| ctctcttaca | caaacccagc | agtggcagcc | acttctgcca | acttgtag | | 1608 |

<210> SEQ ID NO 8

<211> LENGTH: 535
<212> TYPE: PRT
<213> ORGANISM: Homo sapiens

<400> SEQUENCE: 8

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
        20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Asn
210                 215                 220

Arg Pro Ala Leu Gly Ser Thr Ala Pro Pro Val His Asn Val Thr Ser
225                 230                 235                 240

Ala Ser Gly Ser Ala Ser Gly Ser Ala Ser Thr Leu Val His Asn Gly
                245                 250                 255

Thr Ser Ala Arg Ala Thr Thr Thr Pro Ala Ser Lys Ser Thr Pro Phe
            260                 265                 270

Ser Ile Pro Ser His His Ser Asp Thr Pro Thr Thr Leu Ala Ser His
        275                 280                 285

Ser Thr Lys Thr Asp Ala Ser Ser Thr His His Ser Thr Val Pro Pro
290                 295                 300

Leu Thr Ser Ser Asn His Ser Thr Ser Pro Gln Leu Ser Thr Gly Val
305                 310                 315                 320

Ser Phe Phe Phe Leu Ser Phe His Ile Ser Asn Leu Gln Phe Asn Ser
                325                 330                 335

Ser Leu Glu Asp Pro Ser Thr Asp Tyr Tyr Gln Glu Leu Gln Arg Asp
            340                 345                 350

Ile Ser Glu Met Phe Leu Gln Ile Tyr Lys Gln Gly Gly Phe Leu Gly
        355                 360                 365

Leu Ser Asn Ile Lys Phe Arg Pro Gly Ser Val Val Val Gln Leu Thr
370                 375                 380

Leu Ala Phe Arg Glu Gly Thr Ile Asn Val His Asp Val Glu Thr Gln

```
                385                 390                 395                 400
        Phe Asn Gln Tyr Lys Thr Glu Ala Ala Ser Arg Tyr Asn Leu Thr Ile
                        405                 410                 415

Ser Asp Val Ser Val Ser Asp Val Pro Phe Pro Phe Ser Ala Gln Ser
                    420                 425                 430

Gly Ala Gly Val Pro Gly Trp Gly Ile Ala Leu Leu Val Leu Val Cys
                435                 440                 445

Val Leu Val Ala Leu Ala Ile Val Tyr Leu Ile Ala Leu Ala Val Cys
                450                 455                 460

Gln Cys Arg Arg Lys Asn Tyr Gly Gln Leu Asp Ile Phe Pro Ala Arg
        465                 470                 475                 480

Asp Thr Tyr His Pro Met Ser Glu Tyr Pro Thr Tyr His Thr His Gly
                        485                 490                 495

Arg Tyr Val Pro Pro Ser Ser Thr Asp Arg Ser Pro Tyr Glu Lys Val
                    500                 505                 510

Ser Ala Gly Asn Gly Gly Ser Ser Leu Ser Tyr Thr Asn Pro Ala Val
                515                 520                 525

Ala Ala Thr Ser Ala Asn Leu
                530                 535

<210> SEQ ID NO 9
<211> LENGTH: 2046
<212> TYPE: DNA
<213> ORGANISM: Marburg virus

<400> SEQUENCE: 9
atgtggacta catgcttctt tatcagtctc atcttgatcc aagggataaa aactctccct      60
attttggaga tagccagtaa cgatcaaccc caaaatgtgg attcggtatg ctccggaact     120
ctccagaaaa cagaagacgt ccatctgatg ggatttacac tgagcgggca gaaagttgct     180
gattcccctt tggaggcatc caagcgatgg gctttcagga caggtgtacc tcctaagaat     240
gttgagtata cggaagggga ggaagccaaa acatgctaca atataagtgt aacggatccc     300
tctggaaaat ccttgctgtt agatcctccc accaacgtcc gagactatcc taaatgcaaa     360
actatccatc acattcaagg tcaaaaccct catgcgcagg gatcgccct  ccatttgtgg     420 ggagcatttt tcctatatga tcgcattgcc tccacaacaa tgtaccgagg caaagtcttc     480
actgaaggga catagcagc catgattgtc aataagcag tgcacaaaat gattttctcg      540
aggcaaggac aagggtaccg tcacatgaat ctgacttcta ctaataaata ttggacaagt     600
agcaacggaa cgcaaacaaa tgacactgga tgctttggta ctcttcaaga atacaattct     660
acgaagaacc aaacatgtgc tccgtctaaa acacccccac caccgccac agcccatccg      720 gagatcaaac ccacaagcac cccaaccgat gccactagac tcaacaccac aaacccaaac     780
agtgatgatg aggatctcac aacatccggc tcagggtctg gggaacagga accctatacg     840
acttctgatg cggtcactaa gcaagggctt catcaacaa tgccacccac tctctcaccg      900
caaccaggca cgccacagca aggaggaaac aacacaaacc actcccaaga cgctgcaact     960
gaacttgaca caccaatac aactgcacaa ccgcccatgc cctcccacaa caccaccaca     1020
atctccacca caacaccctc caaacacaac ctcagcaccc tctccgaacc accacaaaac     1080
accaccaatc ccaacacaca aagcatggcc actgaaaatg agaaaaccag tgccccccg      1140 aaaacaaccc tgcctccaac agaaagtcct accacagaaa agagcaccaa caatacaaaa     1200
agccccacca caatggaacc aaatacaaca aacggacatt tcactagtcc ctcctccacc     1260
```

```
cccaactcga ctactcaaca tcttatatat ttcaggagga aacgaagtat cctctggagg    1320
gaaggcgaca tgttcccttt tctagatggg ttaataaatg ctccaattga ttttgatcca    1380
gttccaaata caaagacaat cttttgatgaa tcttctagtt ctggtgcttc agccaggaa    1440 gatcaacatg catcctccaa tatcagttta actttatctt atcttcctca tacaagtgaa    1500
aacactgcct actctggaga aaatgaaaat gattgtgatg cagagctaag aatttggagc    1560
gttcaggagg acgacctggc agcagggctc agttggatac cattttttgg ccctggaatc    1620
gaaggacttt ataccgctgg tttaattaaa aatcaaaaca atttggtctg caggttgagg    1680
cgtctagcca atcaaactgc aaaatctttg gaactcttac taagggtcac aaccgaggaa    1740
agaacatttt ctttaatcaa tagacatgct attgactttc tactcacaag gtggggagga    1800
acatgcaaag tgcttggacc cgattgttgc ataggaatag aggacttgtc agaaatatt    1860 tcagaacaga ttgaccaaat caagaaggac gaacaaaaag aggggactgg ttggggtctg    1920
ggtggtaaat ggtggacatc cgactgggt gttcttacta acttgggcat cttactacta    1980
ttgtccatag ctgtcttgat tgctctatcc tgtatttgtc gtatctttac taaatatatt    2040
ggatag                                                               2046
```

<210> SEQ ID NO 10
<211> LENGTH: 681
<212> TYPE: PRT
<213> ORGANISM: Marburg virus

<400> SEQUENCE: 10

```
Met Trp Thr Thr Cys Phe Phe Ile Ser Leu Ile Leu Ile Gln Gly Ile
1               5                   10                  15

Lys Thr Leu Pro Ile Leu Glu Ile Ala Ser Asn Asp Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Ala Lys Thr Cys Tyr Asn Ile Ser
                85                  90                  95

Val Thr Asp Pro Ser Gly Lys Ser Leu Leu Asp Pro Pro Thr Asn
            100                 105                 110

Val Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Gly Thr Gln Thr Asn Asp
        195                 200                 205

Thr Gly Cys Phe Gly Thr Leu Gln Glu Tyr Asn Ser Thr Lys Asn Gln
    210                 215                 220

Thr Cys Ala Pro Ser Lys Thr Pro Pro Pro Pro Thr Ala His Pro
```

-continued

```
            225                 230                 235                 240
Glu Ile Lys Pro Thr Ser Thr Pro Thr Asp Ala Thr Arg Leu Asn Thr
                245                 250                 255

Thr Asn Pro Asn Ser Asp Asp Glu Asp Leu Thr Thr Ser Gly Ser Gly
                260                 265                 270

Ser Gly Glu Gln Glu Pro Tyr Thr Thr Ser Asp Ala Val Thr Lys Gln
                275                 280                 285

Gly Leu Ser Ser Thr Met Pro Pro Thr Leu Ser Gln Pro Gly Thr
    290                 295                 300

Pro Gln Gln Gly Gly Asn Asn Thr Asn His Ser Gln Asp Ala Ala Thr
305                 310                 315                 320

Glu Leu Asp Asn Thr Asn Thr Thr Ala Gln Pro Pro Met Pro Ser His
                325                 330                 335

Asn Thr Thr Thr Ile Ser Thr Asn Asn Thr Ser Lys His Asn Leu Ser
                340                 345                 350

Thr Leu Ser Glu Pro Pro Gln Asn Thr Thr Asn Pro Asn Thr Gln Ser
                355                 360                 365

Met Ala Thr Glu Asn Glu Lys Thr Ser Ala Pro Pro Lys Thr Thr Leu
                370                 375                 380

Pro Pro Thr Glu Ser Pro Thr Thr Glu Lys Ser Thr Asn Asn Thr Lys
385                 390                 395                 400

Ser Pro Thr Thr Met Glu Pro Asn Thr Thr Asn Gly His Phe Thr Ser
                405                 410                 415

Pro Ser Ser Thr Pro Asn Ser Thr Thr Gln His Leu Ile Tyr Phe Arg
                420                 425                 430

Arg Lys Arg Ser Ile Leu Trp Arg Glu Gly Asp Met Phe Pro Phe Leu
                435                 440                 445

Asp Gly Leu Ile Asn Ala Pro Ile Asp Phe Asp Pro Val Pro Asn Thr
                450                 455                 460

Lys Thr Ile Phe Asp Glu Ser Ser Ser Gly Ala Ser Ala Glu Glu
465                 470                 475                 480

Asp Gln His Ala Ser Ser Asn Ile Ser Leu Thr Leu Ser Tyr Leu Pro
                485                 490                 495

His Thr Ser Glu Asn Thr Ala Tyr Ser Gly Glu Asn Glu Asn Asp Cys
                500                 505                 510

Asp Ala Glu Leu Arg Ile Trp Ser Val Gln Glu Asp Asp Leu Ala Ala
                515                 520                 525

Gly Leu Ser Trp Ile Pro Phe Phe Gly Pro Gly Ile Glu Gly Leu Tyr
    530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
                565                 570                 575

Thr Thr Glu Glu Arg Thr Phe Ser Leu Ile Asn Arg His Ala Ile Asp
                580                 585                 590

Phe Leu Leu Thr Arg Trp Gly Gly Thr Cys Lys Val Leu Gly Pro Asp
                595                 600                 605

Cys Cys Ile Gly Ile Glu Asp Leu Ser Arg Asn Ile Ser Glu Gln Ile
                610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655
```

Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680

<210> SEQ ID NO 11
<211> LENGTH: 1608
<212> TYPE: DNA
<213> ORGANISM: Homo sapiens

<400> SEQUENCE: 11

| | | | | | |
|---|---|---|---|---|---|
| atgacaccgg | gcacccagtc | tcctttcttc | ctgctgctgc | tcctcacagt | gcttacagtt | 60 |
| gttacgggtt | ctggtcatgc | aagctctacc | ccaggtggag | aaaaggagac | ttcggctacc | 120 |
| cagagaagtt | cagtgcccag | ctctactgag | aagaatgctg | tgagtatgac | cagcagcgta | 180 |
| ctctccagcc | acagccccgg | ttcaggctcc | tccaccactc | agggacagga | tgtcactctg | 240 |
| gccccggcca | cggaaccagc | ttcaggttca | gctgccacct | gggacagga | tgtcacctcg | 300 |
| gtcccagtca | ccaggccagc | cctgggctcc | accaccccgc | cagcccacga | tgtcacctca | 360 |
| gccccggaca | caagccagc | cccgggctcc | accgccccc | cagcccacgg | tgtcacctcg | 420 |
| gccccggaca | ccaggccggc | cccgggctcc | accgccccc | cagcccacgg | tgtcacctcg | 480 |
| gccccggaca | ccaggccggc | cccgggctcc | accgccccc | cagcccacgg | tgtcacctcg | 540 |
| gccccggaca | ccaggccggc | cccgggctcc | accgccccc | cagcccacgg | tgtcacctcg | 600 |
| gccccggaca | ccaggccggc | cccgggctcc | accgccccc | cagcccatgg | tgtcacctcg | 660 |
| gccccggaca | acaggcccgc | cttgggctcc | accgcccctc | cagtccacaa | tgtcacctcg | 720 |
| gcctcaggct | ctgcatcagg | ctcagcttct | actctggtgc | acaacggcac | ctctgccagg | 780 |
| gctaccacaa | ccccagccag | caagagcact | ccattctcaa | ttcccagcca | ccactctgat | 840 |
| actcctacca | cccttgccag | ccatagcacc | aagactgatg | ccagtagcac | tcaccatagc | 900 |
| acggtacctc | ctctcacctc | ctccaatcac | agcacttctc | cccagttgtc | tactggggtc | 960 |
| tctttctttt | tcctgtcttt | tcacatttca | aacctccagt | ttaattcctc | tctggaagat | 1020 |
| cccagcaccg | actactacca | agagctgcag | agagacattt | ctgaaatgtt | tttgcagatt | 1080 |
| tataaacaag | ggggttttct | gggcctctcc | aatattaagt | tcaggccagg | atctgtggtg | 1140 |
| gtacaattga | ctctggcctt | ccgagaaggt | accatcaatg | tccacgacgt | ggagacacag | 1200 |
| ttcaatcagt | ataaaacgga | agcagcctct | cgatataacc | tgacgatctc | agacgtcagc | 1260 |
| gtgagtgatg | tgccatttcc | tttctctgcc | cagtctgggg | ctggggtgcc | aggctggggc | 1320 |
| atcgcgctgc | tggtgctggt | ctgtgttctg | gttgcgctgg | ccattgtcta | tctcattgcc | 1380 |
| ttggctgtct | gtcagtgccg | ccgaaagaac | tacgggcagc | tggacatctt | ccagcccgg | 1440 |
| gatacctacc | atcctatgag | cgagtacccc | acctaccaca | cccatgggcg | ctatgtgccc | 1500 |
| cctagcagta | ccgatcgtag | cccctatgag | aaggtttctg | caggtaatgg | tggcagcagc | 1560 |
| ctctcttaca | caaacccagc | agtggcagcc | acttctgcca | acttgtag | | 1608 |

<210> SEQ ID NO 12
<211> LENGTH: 535
<212> TYPE: PRT
<213> ORGANISM: Homo sapiens

<400> SEQUENCE: 12

Met Thr Pro Gly Thr Gln Ser Pro Phe Phe Leu Leu Leu Leu Leu Thr
1               5                   10                  15

```
Val Leu Thr Val Val Thr Gly Ser Gly His Ala Ser Ser Thr Pro Gly
            20              25              30
Gly Glu Lys Glu Thr Ser Ala Thr Gln Arg Ser Ser Val Pro Ser Ser
            35              40              45
Thr Glu Lys Asn Ala Val Ser Met Thr Ser Ser Val Leu Ser Ser His
 50              55              60
Ser Pro Gly Ser Gly Ser Ser Thr Thr Gln Gly Gln Asp Val Thr Leu
 65              70              75              80
Ala Pro Ala Thr Glu Pro Ala Ser Gly Ser Ala Ala Thr Trp Gly Gln
            85              90              95
Asp Val Thr Ser Val Pro Val Thr Arg Pro Ala Leu Gly Ser Thr Thr
            100             105             110
Pro Pro Ala His Asp Val Thr Ser Ala Pro Asp Asn Lys Pro Ala Pro
            115             120             125
Gly Ser Thr Ala Pro Pro Ala His Gly Val Thr Ser Ala Pro Asp Thr
130             135             140
Arg Pro Ala Pro Gly Ser Thr Ala Pro Pro Ala His Gly Val Thr Ser
145             150             155             160
Ala Pro Asp Thr Arg Pro Ala Pro Gly Ser Thr Ala Pro Pro Ala His
            165             170             175
Gly Val Thr Ser Ala Pro Asp Thr Arg Pro Ala Pro Gly Ser Thr Ala
            180             185             190
Pro Pro Ala His Gly Val Thr Ser Ala Pro Asp Thr Arg Pro Ala Pro
            195             200             205
Gly Ser Thr Ala Pro Pro Ala His Gly Val Thr Ser Ala Pro Asp Asn
            210             215             220
Arg Pro Ala Leu Gly Ser Thr Ala Pro Pro Val His Asn Val Thr Ser
225             230             235             240
Ala Ser Gly Ser Ala Ser Gly Ser Ala Ser Thr Leu Val His Asn Gly
            245             250             255
Thr Ser Ala Arg Ala Thr Thr Thr Pro Ala Ser Lys Ser Thr Pro Phe
            260             265             270
Ser Ile Pro Ser His His Ser Asp Thr Pro Thr Thr Leu Ala Ser His
            275             280             285
Ser Thr Lys Thr Asp Ala Ser Ser Thr His His Ser Thr Val Pro Pro
            290             295             300
Leu Thr Ser Ser Asn His Ser Thr Ser Pro Gln Leu Ser Thr Gly Val
305             310             315             320
Ser Phe Phe Phe Leu Ser Phe His Ile Ser Asn Leu Gln Phe Asn Ser
            325             330             335
Ser Leu Glu Asp Pro Ser Thr Asp Tyr Tyr Gln Glu Leu Gln Arg Asp
            340             345             350
Ile Ser Glu Met Phe Leu Gln Ile Tyr Lys Gln Gly Gly Phe Leu Gly
            355             360             365
Leu Ser Asn Ile Lys Phe Arg Pro Gly Ser Val Val Val Gln Leu Thr
            370             375             380
Leu Ala Phe Arg Glu Gly Thr Ile Asn Val His Asp Val Glu Thr Gln
385             390             395             400
Phe Asn Gln Tyr Lys Thr Glu Ala Ala Ser Arg Tyr Asn Leu Thr Ile
            405             410             415
Ser Asp Val Ser Val Ser Asp Val Pro Phe Pro Phe Ser Ala Gln Ser
            420             425             430
```

```
Gly Ala Gly Val Pro Gly Trp Gly Ile Ala Leu Leu Val Leu Val Cys
        435                 440                 445

Val Leu Val Ala Leu Ala Ile Val Tyr Leu Ile Ala Leu Ala Val Cys
    450                 455                 460

Gln Cys Arg Arg Lys Asn Tyr Gly Gln Leu Asp Ile Phe Pro Ala Arg
465                 470                 475                 480

Asp Thr Tyr His Pro Met Ser Glu Tyr Pro Thr Tyr His Thr His Gly
                485                 490                 495

Arg Tyr Val Pro Pro Ser Ser Thr Asp Arg Ser Pro Tyr Glu Lys Val
            500                 505                 510

Ser Ala Gly Asn Gly Gly Ser Ser Leu Ser Tyr Thr Asn Pro Ala Val
        515                 520                 525

Ala Ala Thr Ser Ala Asn Leu
    530                 535

<210> SEQ ID NO 13
<211> LENGTH: 30
<212> TYPE: PRT
<213> ORGANISM: Marburg virus

<400> SEQUENCE: 13

Trp Trp Thr Ser Asp Trp Gly Val Leu Thr Asn Leu Gly Ile Leu Leu
1               5                   10                  15

Leu Leu Ser Ile Ala Val Leu Ile Ala Leu Ser Cys Ile Cys
            20                  25                  30

<210> SEQ ID NO 14
<211> LENGTH: 1608
<212> TYPE: DNA
<213> ORGANISM: Homo sapiens

<400> SEQUENCE: 14
atgacaccgg gcacccagtc tcctttcttc ctgctgctgc tcctcacagt gcttacagtt     60
gttacgggtt ctggtcatgc aagctctacc ccaggtggag aaaaggagac ttcggctacc    120
cagagaagtt cagtgcccag ctctactgag aagaatgctg tgagtatgac cagcagcgta    180
ctctccagcc acagccccgg ttcaggctcc tccaccactc agggacagga tgtcactctg    240
gccccggcca cggaaccagc ttcaggttca gctgccacct ggggacagga tgtcacctcg    300
gtcccagtca ccaggccagc cctgggctcc accaccccgc cagcccacga tgtcacctca    360
gccccggaca acaagccagc cccgggctcc accgcccccc cagcccacgg tgtcacctcg    420
gccccggaca ccaggccggc cccgggctcc accgcccccc cagcccacgg tgtcacctcg    480
gccccggaca ccaggccggc cccgggctcc accgcccccc cagcccacgg tgtcacctcg    540
gccccggaca ccaggccggc cccgggctcc accgcccccc cagcccacgg tgtcacctcg    600
gccccggaca ccaggccggc cccgggctcc accgcccccc cagcccatgg tgtcacctcg    660
gccccggaca acaggcccgc cttgggctcc accgcccctc cagtccacaa tgtcacctcg    720
gcctcaggct ctgcatcagg ctcagcttct actctggtgc acaacggcac ctctgccagg    780
gctaccacaa ccccagccag caagagcact ccattctcaa ttcccagcca ccactctgat    840
actcctacca cccttgccag ccatagcacc aagactgatg ccagtagcac tcaccatagc    900
acggtacctc ctctcacctc ctccaatcac agcacttctc cccagttgtc tactggggtc    960
tctttctttt tcctgtcttt tcacatttca aacctccagt ttaattcctc tctggaagat   1020
cccagcaccg actactacca agagctgcag agagacattt ctgaaatgtt tttgcagatt   1080
```

-continued

```
tataaacaag ggggttttct gggcctctcc aatattaagt tcaggccagg atctgtggtg      1140
gtacaattga ctctggcctt ccgagaaggt accatcaatg tccacgacgt ggagacacag      1200
ttcaatcagt ataaaacgga agcagcctct cgatataacc tgacgatctc agacgtcagc      1260
gtgagtgatg tgccattttcc tttctctgcc cagtctgggg ctgggggtgtg gtggacatcc     1320 gactggggtg ttcttactaa cttgggcatc ttactactat tgtccatagc tgtcttgatt      1380
gctctatcct gtatttgtcg ccgaaagaac tacgggcagc tggacatctt tccagcccgg      1440 gataccctacc atcctatgag cgagtacccc acctaccaca cccatgggcg ctatgtgccc     1500
cctagcagta ccgatcgtag cccctatgag aaggtttctg caggtaatgg tggcagcagc      1560
ctctcttaca caaacccagc agtggcagcc acttctgcca acttgtag                   1608
```

<210> SEQ ID NO 15
<211> LENGTH: 535
<212> TYPE: PRT
<213> ORGANISM: Homo sapiens

<400> SEQUENCE: 15

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Asn
    210                 215                 220

Arg Pro Ala Leu Gly Ser Thr Ala Pro Pro Val His Asn Val Thr Ser
225                 230                 235                 240

Ala Ser Gly Ser Ala Ser Gly Ser Ala Ser Thr Leu Val His Asn Gly
                245                 250                 255

Thr Ser Ala Arg Ala Thr Thr Thr Pro Ala Ser Lys Ser Thr Pro Phe
            260                 265                 270

Ser Ile Pro Ser His His Ser Asp Thr Pro Thr Thr Leu Ala Ser His
        275                 280                 285
```

-continued

```
Ser Thr Lys Thr Asp Ala Ser Ser Thr His His Ser Thr Val Pro Pro
    290                 295                 300
Leu Thr Ser Ser Asn His Ser Thr Ser Pro Gln Leu Ser Thr Gly Val
305                 310                 315                 320
Ser Phe Phe Phe Leu Ser Phe His Ile Ser Asn Leu Gln Phe Asn Ser
            325                 330                 335
Ser Leu Glu Asp Pro Ser Thr Asp Tyr Tyr Gln Glu Leu Gln Arg Asp
            340                 345                 350
Ile Ser Glu Met Phe Leu Gln Ile Tyr Lys Gln Gly Gly Phe Leu Gly
        355                 360                 365
Leu Ser Asn Ile Lys Phe Arg Pro Gly Ser Val Val Val Gln Leu Thr
    370                 375                 380
Leu Ala Phe Arg Glu Gly Thr Ile Asn Val His Asp Val Glu Thr Gln
385                 390                 395                 400
Phe Asn Gln Tyr Lys Thr Glu Ala Ala Ser Arg Tyr Asn Leu Thr Ile
            405                 410                 415
Ser Asp Val Ser Val Ser Asp Val Pro Phe Pro Phe Ser Ala Gln Ser
            420                 425                 430
Gly Ala Gly Val Trp Trp Thr Ser Asp Trp Gly Val Leu Thr Asn Leu
        435                 440                 445
Gly Ile Leu Leu Leu Leu Ser Ile Ala Val Leu Ile Ala Leu Ser Cys
    450                 455                 460
Ile Cys Arg Arg Lys Asn Tyr Gly Gln Leu Asp Ile Phe Pro Ala Arg
465                 470                 475                 480
Asp Thr Tyr His Pro Met Ser Glu Tyr Pro Thr Tyr His Thr His Gly
            485                 490                 495
Arg Tyr Val Pro Pro Ser Ser Thr Asp Arg Ser Pro Tyr Glu Lys Val
            500                 505                 510
Ser Ala Gly Asn Gly Gly Ser Ser Leu Ser Tyr Thr Asn Pro Ala Val
        515                 520                 525
Ala Ala Thr Ser Ala Asn Leu
    530                 535

<210> SEQ ID NO 16
<211> LENGTH: 1608
<212> TYPE: DNA
<213> ORGANISM: Homo sapiens

<400> SEQUENCE: 16
atgacacctg gaacacaatc tccattttt ctactactac tattgacagt actaacagta      60
gtaacaggat ctggacatgc gtctagtaca ccaggtggag aaaaagaaac atctgcgact     120
caaagatctt ctgtaccatc ttctacagaa aaaaatgcgg tatctatgac atctagtgta     180
ctatcttctc attctcctgg atctggatct tctactacac aaggacaaga tgtaacacta     240
gcgccagcta cagaaccagc ttctggatct gctgctactt ggggtcaaga tgttacttct     300
gttccagtaa caagaccagc gctaggatct acaacaccac cagcgcatga tgtaacaagt     360
gcgccagata taaaccagc gcctggttct actgctccac cagctcatgg tgttacttca     420
gcgcctgata caagacctgc acctggatct acagctcctc ctgcacatgg tgtaacatct     480
gctccagata caagaccagc tccaggttca acagcacctc cagcgcatgg tgttactagt     540
gctccagata caagacctgc gcctggaagt actgcaccac cagcacatgg tgtaactagt     600
gcgcctgata caagaccagc gccaggatca actgctcctc ctgctcatgg tgttacaagt     660
```

```
gcacctgata atagacctgc gttgggatct actgcgcctc cagttcataa tgtaacatca    720
gcgtctggaa gtgcgtctgg ttctgcgtct acattggttc ataatggtac atctgcgaga    780
gcgacaacaa ctccagcgtc taaatctaca ccatttccta ttccatctca tcattctgat    840
acaccaacaa cattggcgag tcattctaca aaaacagatg cgagttctac acatcattct    900
actgtaccac cactaacatc ttctaatcat agtacatctc cacaactatc tactggtgta    960 tcttttttt ttctatcttt tcatatttct aatctacagt ttaattctag tttggaagat   1020
ccatctacag attattatca agaactacaa agagatattt ctgaaatgtt tctacaaata   1080
tataaacaag gaggatttct aggactatct aatattaagt ttagaccagg atctgtagta   1140
gttcaactaa ctctagcgtt tagagaaggt actattaatg tacatgatgt tgaaacacag   1200
tttaatcaat ataaaacaga agcggcgtct agatataatc taacaatttc tgatgtatct   1260
gtatctgatg ttccatttcc attttctgcg caatctggtg ctggtgtatg gtggacatct   1320
gattggggag tactaactaa tctaggaatt ctactattgc tatctattgc ggtactaatt   1380
gcgctatctt gtatatgtag aagaaaaaat tatggacaac tagatatttt tccagcgaga   1440
gatacttatc atccaatgtc tgaatatcca acatatcata cacatggaag atatgtacca   1500
ccttcttcaa cagatagatc tccatatgaa aaagtatctg cgggaaatgg tggttcttct   1560
ctatcttata caaatccagc ggtagcggcg acttctgcga atctataa                1608
```

<210> SEQ ID NO 17
<211> LENGTH: 535
<212> TYPE: PRT
<213> ORGANISM: Homo sapiens

<400> SEQUENCE: 17

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Asn
            210                 215                 220

Arg Pro Ala Leu Gly Ser Thr Ala Pro Pro Val His Asn Val Thr Ser
225                 230                 235                 240

Ala Ser Gly Ser Ala Ser Gly Ser Ala Ser Thr Leu Val His Asn Gly
                245                 250                 255

Thr Ser Ala Arg Ala Thr Thr Pro Ala Ser Lys Ser Thr Pro Phe
            260                 265                 270

Ser Ile Pro Ser His His Ser Asp Thr Pro Thr Thr Leu Ala Ser His
            275                 280                 285

Ser Thr Lys Thr Asp Ala Ser Ser Thr His His Ser Thr Val Pro Pro
290                 295                 300

Leu Thr Ser Ser Asn His Ser Thr Ser Pro Gln Leu Ser Thr Gly Val
305                 310                 315                 320

Ser Phe Phe Phe Leu Ser Phe His Ile Ser Asn Leu Gln Phe Asn Ser
                325                 330                 335

Ser Leu Glu Asp Pro Ser Thr Asp Tyr Tyr Gln Glu Leu Gln Arg Asp
            340                 345                 350

Ile Ser Glu Met Phe Leu Gln Ile Tyr Lys Gln Gly Gly Phe Leu Gly
            355                 360                 365

Leu Ser Asn Ile Lys Phe Arg Pro Gly Ser Val Val Val Gln Leu Thr
370                 375                 380

Leu Ala Phe Arg Glu Gly Thr Ile Asn Val His Asp Val Glu Thr Gln
385                 390                 395                 400

Phe Asn Gln Tyr Lys Thr Glu Ala Ala Ser Arg Tyr Asn Leu Thr Ile
                405                 410                 415

Ser Asp Val Ser Val Ser Asp Val Pro Phe Pro Phe Ser Ala Gln Ser
            420                 425                 430

Gly Ala Gly Val Trp Trp Thr Ser Asp Trp Gly Val Leu Thr Asn Leu
            435                 440                 445

Gly Ile Leu Leu Leu Leu Ser Ile Ala Val Leu Ile Ala Leu Ser Cys
450                 455                 460

Ile Cys Arg Arg Lys Asn Tyr Gly Gln Leu Asp Ile Phe Pro Ala Arg
465                 470                 475                 480

Asp Thr Tyr His Pro Met Ser Glu Tyr Pro Thr Tyr His Thr His Gly
                485                 490                 495

Arg Tyr Val Pro Pro Ser Ser Thr Asp Arg Ser Pro Tyr Glu Lys Val
            500                 505                 510

Ser Ala Gly Asn Gly Gly Ser Ser Leu Ser Tyr Thr Asn Pro Ala Val
            515                 520                 525

Ala Ala Thr Ser Ala Asn Leu
530                 535

<210> SEQ ID NO 18
<211> LENGTH: 1608
<212> TYPE: DNA
<213> ORGANISM: Homo sapiens

<400> SEQUENCE: 18
atgacacctg gaacacaatc tccattcttc ctactactac tattgacagt actaacagta    60
gtaacaggat ctggacatgc gtctagtaca ccaggtggag agaaggaaac atctgcgact   120
caaagatctt ctgtaccatc ttctacagag aagaatgcgg tatctatgac atctagtgta   180
ctatcttctc attctcctgg atctggatct tctactacac aaggacaaga tgtaacacta   240

```
gcgccagcta cagaaccagc ttctggatct gctgctactt ggggtcaaga tgttacttct    300
gttccagtaa caagaccagc gctaggatct acaacaccac cagcgcatga tgtaacaagt    360
gcgccagata ataagccagc gcctggttct actgctccac cagctcatgg tgttacttca    420
gcgcctgata caagacctgc acctggatct acagctcctc ctgcacatgg tgtaacatct    480
gctccagata caagaccagc tccaggttca acagcacctc cagcgcatgg tgttactagt    540
gctccagata caagacctgc gcctggaagt actgcaccac cagcacatgg tgtaactagt    600
gcgcctgata caagaccagc gccaggatca actgctcctc ctgctcatgg tgttacaagt    660
gcacctgata tagacctgc gttgggatct actgcgcctc cagttcataa tgtaacatca     720
gcgtctggaa gtgcgtctgg ttctgcgtct acattggttc ataatggtac atctgcgaga    780
gcgacaacaa ctccagcgtc taagtctaca ccattctcta ttccatctca tcattctgat    840
acaccaacaa cattggcgag tcattctaca aagacagatg cgagttctac acatcattct    900
actgtaccac cactaacatc ttctaatcat agtacatctc cacaactatc tactggtgta    960
tctttcttct tcctatcctt tcatatttct aatctacagt tcaattctag tttgaagat    1020 ccatctacag attattatca agaactacaa agagatattt ctgaaatgtt tctacaaata    1080
tataaacaag gaggatttct aggactatct aatattaagt ttagaccagg atctgtagta    1140
gttcaactaa ctctagcgtt tagagaaggt actattaatg tacatgatgt tgaaacacag    1200
tttaatcaat ataagacaga agcggcgtct agatataatc taacaatttc tgatgtatct    1260
gtatctgatg ttccatttcc attttctgcg caatctggtg ctggtgtatg gtggacatct    1320
gattggggag tactaactaa tctaggaatt ctactattgc tatctattgc ggtactaatt    1380
gcgctatctt gtatatgtag aagaaagaat tatggacaac tagatatttt cccagcgaga    1440
gatacttatc atccaatgtc tgaatatcca acatatcata cacatggaag atatgtacca    1500
ccttcttcaa cagatagatc tccatatgag aaggtatctg cgggaaatgg tggttcttct    1560
ctatcttata caaatccagc ggtagcggcg acttctgcga atctataa                 1608
```

<210> SEQ ID NO 19
<211> LENGTH: 535
<212> TYPE: PRT
<213> ORGANISM: Homo sapiens

<400> SEQUENCE: 19

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
```

```
            130                 135                 140
Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
                180                 185                 190

Pro Pro Ala His Gly Val Thr Ser Ala Pro Asp Thr Arg Pro Ala Pro
                195                 200                 205

Gly Ser Thr Ala Pro Pro Ala His Gly Val Thr Ser Ala Pro Asp Asn
        210                 215                 220

Arg Pro Ala Leu Gly Ser Thr Ala Pro Pro Val His Asn Val Thr Ser
225                 230                 235                 240

Ala Ser Gly Ser Ala Ser Gly Ser Ala Ser Thr Leu Val His Asn Gly
                245                 250                 255

Thr Ser Ala Arg Ala Thr Thr Thr Pro Ala Ser Lys Ser Thr Pro Phe
                260                 265                 270

Ser Ile Pro Ser His His Ser Asp Thr Pro Thr Thr Leu Ala Ser His
        275                 280                 285

Ser Thr Lys Thr Asp Ala Ser Ser Thr His His Ser Thr Val Pro Pro
        290                 295                 300

Leu Thr Ser Ser Asn His Ser Thr Ser Pro Gln Leu Ser Thr Gly Val
305                 310                 315                 320

Ser Phe Phe Phe Leu Ser Phe His Ile Ser Asn Leu Gln Phe Asn Ser
                325                 330                 335

Ser Leu Glu Asp Pro Ser Thr Asp Tyr Tyr Gln Glu Leu Gln Arg Asp
                340                 345                 350

Ile Ser Glu Met Phe Leu Gln Ile Tyr Lys Gln Gly Gly Phe Leu Gly
                355                 360                 365

Leu Ser Asn Ile Lys Phe Arg Pro Gly Ser Val Val Val Gln Leu Thr
        370                 375                 380

Leu Ala Phe Arg Glu Gly Thr Ile Asn Val His Asp Val Glu Thr Gln
385                 390                 395                 400

Phe Asn Gln Tyr Lys Thr Glu Ala Ala Ser Arg Tyr Asn Leu Thr Ile
                405                 410                 415

Ser Asp Val Ser Val Ser Asp Val Pro Phe Pro Phe Ser Ala Gln Ser
                420                 425                 430

Gly Ala Gly Val Trp Trp Thr Ser Asp Trp Gly Val Leu Thr Asn Leu
                435                 440                 445

Gly Ile Leu Leu Leu Leu Ser Ile Ala Val Leu Ile Ala Leu Ser Cys
        450                 455                 460

Ile Cys Arg Arg Lys Asn Tyr Gly Gln Leu Asp Ile Phe Pro Ala Arg
465                 470                 475                 480

Asp Thr Tyr His Pro Met Ser Glu Tyr Pro Thr Tyr His Thr His Gly
                485                 490                 495

Arg Tyr Val Pro Pro Ser Ser Thr Asp Arg Ser Pro Tyr Glu Lys Val
                500                 505                 510

Ser Ala Gly Asn Gly Gly Ser Ser Leu Ser Tyr Thr Asn Pro Ala Val
                515                 520                 525

Ala Ala Thr Ser Ala Asn Leu
        530                 535

<210> SEQ ID NO 20
```

```
<211> LENGTH: 60
<212> TYPE: DNA
<213> ORGANISM: Homo sapiens

<400> SEQUENCE: 20
gctcatggtg ttacttcagc gcctgataca agacctgcac ctggatctac agctcctcct    60

<210> SEQ ID NO 21
<211> LENGTH: 20
<212> TYPE: PRT
<213> ORGANISM: Homo sapiens

<400> SEQUENCE: 21

Ala His Gly Val Thr Ser Ala Pro Asp Thr Arg Pro Ala Pro Gly Ser
1               5                   10                  15

Thr Ala Pro Pro
            20

<210> SEQ ID NO 22
<211> LENGTH: 60
<212> TYPE: DNA
<213> ORGANISM: Homo sapiens

<400> SEQUENCE: 22
gcacatggtg taacatctgc tccagataca agaccagctc caggttcaac agcacctcca    60

<210> SEQ ID NO 23
<211> LENGTH: 60
<212> TYPE: DNA
<213> ORGANISM: Homo sapiens

<400> SEQUENCE: 23
gcgcatggtg ttactagtgc tccagataca agacctgcgc ctggaagtac tgcaccacca    60

<210> SEQ ID NO 24
<211> LENGTH: 60
<212> TYPE: DNA
<213> ORGANISM: Homo sapiens

<400> SEQUENCE: 24
gcacatggtg taactagtgc gcctgataca agaccagcgc caggatcaac tgctcctcct    60

<210> SEQ ID NO 25
<211> LENGTH: 60
<212> TYPE: DNA
<213> ORGANISM: Homo sapiens

<400> SEQUENCE: 25
gctcatggtg ttacttcagc gcctgataca agacccgcac ccggatctac cgctccgcct    60

<210> SEQ ID NO 26
<211> LENGTH: 60
<212> TYPE: DNA
<213> ORGANISM: Homo sapiens

<400> SEQUENCE: 26
gcacacggcg tcacatctgc tcccgacact cgtccagctc ctggtagcac agcacctcca    60

<210> SEQ ID NO 27
<211> LENGTH: 60
<212> TYPE: DNA
<213> ORGANISM: Homo sapiens

<400> SEQUENCE: 27
```

```
gcgcatggag taaccagtgc accagatacc cgacctgcgc cgggcagtac tgccccaccg    60
```

<210> SEQ ID NO 28
<211> LENGTH: 60
<212> TYPE: DNA
<213> ORGANISM: Homo sapiens

<400> SEQUENCE: 28

```
gcccacgggg tgacgagcgc cccggacacg cgcccagctc cagggtcaac ggcgccccct    60
```

<210> SEQ ID NO 29
<211> LENGTH: 1633
<212> TYPE: DNA
<213> ORGANISM: Homo sapiens

<400> SEQUENCE: 29

```
gcgctcccgg gatgacacct ggaacacaat ctccattctt cctactacta ctattgacag      60
tactaacagt agtaacagga tctggacatg cgtctagtac accaggtgga gagaaggaaa    120
catctgcgac tcaaagatct tctgtaccat cttctacaga gaagaatgcg gtatctatga    180
catctagtgt actatcttct cattctcctg gatctggatc ttctactaca caaggacaag    240
atgtaacact agcgccagct acagaaccag cttctggatc tgctgctact tggggtcaag    300
atgttacttc tgttccagta acaagaccag cgctaggatc tacaacacca ccagcgcatg    360
atgtaacaag tgcgccagat aataagccag cgcctggttc tactgctcca ccagctcatg    420
gtgttacttc agcgcctgat acaagacctg cacctggatc tacagctcct cctgcacatg    480
gtgtaacatc tgctccagat acaagaccag ctccaggttc aacagcacct ccagcgcatg    540
gtgttactag tgctccagat acaagacctg cgcctggaag tactgcacca ccagcacatg    600
gtgtaactag tgcgcctgat acaagaccag cgccaggatc aactgctcct cctgctcatg    660
gtgttacaag tgcacctgat aatagacctg cgttgggatc tactgcgcct ccagttcata    720
atgtaacatc agcgtctgga agtgcgtctg gttctgcgtc tacattggtt cataatggta    780
catctgcgag agcgacaaca actccagcgt ctaagtctac accattctct attccatctc    840
atcattctga taccaacaca acattggcga gtcattctac aaagacagat gcgagttcta    900
cacatcattc tactgtacca ccactaacat cttctaatca tagtacatct ccacaactat    960
ctactggtgt atctttcttc ttcctatcct ttcatatttc taatctacag ttcaattcta   1020
gtttggaaga tccatctaca gattattatc aagaactaca aagagatatt tctgaaatgt   1080
ttctacaaat atataaacaa ggaggatttc taggactatc taatattaag tttagaccag   1140
gatctgtagt agttcaacta actctagcgt ttagagaagg tactattaat gtacatgatg   1200
ttgaaacaca gttaatcaa tataagacag aagcggcgtc tagatataat ctaacaattt   1260
ctgatgtatc tgtatctgat gttccatttc cattctctgc gcaatctggt gctggtgtat   1320
ggtggacatc tgattgggga gtactaacta atctaggaat tctactattg ctatctattg   1380
cggtactaat tgcgctatct tgtatatgta gaagaaagaa ttatggacaa ctagatattt   1440
tcccagcgag agatacttat catccaatgt ctgaatatcc aacatatcat acacatggaa   1500
gatatgtacc accttcttca acagatagat ctccatatga gaaggtatct gcgggaaatg   1560
gtggttcttc tctatcttat acaaatccag cggtagcggc gacttctgcg aatctataat   1620
aagtcgacgc gct                                                      1633
```

<210> SEQ ID NO 30

-continued

```
<211> LENGTH: 535
<212> TYPE: PRT
<213> ORGANISM: Homo sapiens

<400> SEQUENCE: 30
```

| | | | | | | | | | | | | | | | |
|---|---|---|---|---|---|---|---|---|---|---|---|---|---|---|---|
| Met | Thr | Pro | Gly | Thr | Gln | Ser | Pro | Phe | Phe | Leu | Leu | Leu | Leu | Thr | |
| 1 | | | | 5 | | | | | 10 | | | | | 15 | |
| Val | Leu | Thr | Val | Val | Thr | Gly | Ser | Gly | His | Ala | Ser | Ser | Thr | Pro | Gly |
| | | | 20 | | | | | 25 | | | | | 30 | | |
| Gly | Glu | Lys | Glu | Thr | Ser | Ala | Thr | Gln | Arg | Ser | Ser | Val | Pro | Ser | Ser |
| | | 35 | | | | | 40 | | | | | 45 | | | |
| Thr | Glu | Lys | Asn | Ala | Val | Ser | Met | Thr | Ser | Ser | Val | Leu | Ser | Ser | His |
| | 50 | | | | | 55 | | | | | 60 | | | | |
| Ser | Pro | Gly | Ser | Gly | Ser | Ser | Thr | Thr | Gln | Gly | Gln | Asp | Val | Thr | Leu |
| 65 | | | | | 70 | | | | | 75 | | | | | 80 |
| Ala | Pro | Ala | Thr | Glu | Pro | Ala | Ser | Gly | Ser | Ala | Ala | Thr | Trp | Gly | Gln |
| | | | | 85 | | | | | 90 | | | | | 95 | |
| Asp | Val | Thr | Ser | Val | Pro | Val | Thr | Arg | Pro | Ala | Leu | Gly | Ser | Thr | Thr |
| | | | 100 | | | | | 105 | | | | | 110 | | |
| Pro | Pro | Ala | His | Asp | Val | Thr | Ser | Ala | Pro | Asp | Asn | Lys | Pro | Ala | Pro |
| | | 115 | | | | | 120 | | | | | 125 | | | |
| Gly | Ser | Thr | Ala | Pro | Pro | Ala | His | Gly | Val | Thr | Ser | Ala | Pro | Asp | Thr |
| | 130 | | | | | 135 | | | | | 140 | | | | |
| Arg | Pro | Ala | Pro | Gly | Ser | Thr | Ala | Pro | Pro | Ala | His | Gly | Val | Thr | Ser |
| 145 | | | | | 150 | | | | | 155 | | | | | 160 |
| Ala | Pro | Asp | Thr | Arg | Pro | Ala | Pro | Gly | Ser | Thr | Ala | Pro | Pro | Ala | His |
| | | | | 165 | | | | | 170 | | | | | 175 | |
| Gly | Val | Thr | Ser | Ala | Pro | Asp | Thr | Arg | Pro | Ala | Pro | Gly | Ser | Thr | Ala |
| | | | 180 | | | | | 185 | | | | | 190 | | |
| Pro | Pro | Ala | His | Gly | Val | Thr | Ser | Ala | Pro | Asp | Thr | Arg | Pro | Ala | Pro |
| | | 195 | | | | | 200 | | | | | 205 | | | |
| Gly | Ser | Thr | Ala | Pro | Pro | Ala | His | Gly | Val | Thr | Ser | Ala | Pro | Asp | Asn |
| | 210 | | | | | 215 | | | | | 220 | | | | |
| Arg | Pro | Ala | Leu | Gly | Ser | Thr | Ala | Pro | Pro | Val | His | Asn | Val | Thr | Ser |
| 225 | | | | | 230 | | | | | 235 | | | | | 240 |
| Ala | Ser | Gly | Ser | Ala | Ser | Gly | Ser | Ala | Ser | Thr | Leu | Val | His | Asn | Gly |
| | | | | 245 | | | | | 250 | | | | | 255 | |
| Thr | Ser | Ala | Arg | Ala | Thr | Thr | Thr | Pro | Ala | Ser | Lys | Ser | Thr | Pro | Phe |
| | | | 260 | | | | | 265 | | | | | 270 | | |
| Ser | Ile | Pro | Ser | His | His | Ser | Asp | Thr | Pro | Thr | Thr | Leu | Ala | Ser | His |
| | | 275 | | | | | 280 | | | | | 285 | | | |
| Ser | Thr | Lys | Thr | Asp | Ala | Ser | Ser | Thr | His | His | Ser | Thr | Val | Pro | Pro |
| | 290 | | | | | 295 | | | | | 300 | | | | |
| Leu | Thr | Ser | Ser | Asn | His | Ser | Thr | Ser | Pro | Gln | Leu | Ser | Thr | Gly | Val |
| 305 | | | | | 310 | | | | | 315 | | | | | 320 |
| Ser | Phe | Phe | Phe | Leu | Ser | Phe | His | Ile | Ser | Asn | Leu | Gln | Phe | Asn | Ser |
| | | | | 325 | | | | | 330 | | | | | 335 | |
| Ser | Leu | Glu | Asp | Pro | Ser | Thr | Asp | Tyr | Tyr | Gln | Glu | Leu | Gln | Arg | Asp |
| | | | 340 | | | | | 345 | | | | | 350 | | |
| Ile | Ser | Glu | Met | Phe | Leu | Gln | Ile | Tyr | Lys | Gln | Gly | Gly | Phe | Leu | Gly |
| | | 355 | | | | | 360 | | | | | 365 | | | |
| Leu | Ser | Asn | Ile | Lys | Phe | Arg | Pro | Gly | Ser | Val | Val | Val | Gln | Leu | Thr |
| | 370 | | | | | 375 | | | | | 380 | | | | |
| Leu | Ala | Phe | Arg | Glu | Gly | Thr | Ile | Asn | Val | His | Asp | Val | Glu | Thr | Gln |

```
              385                 390                 395                 400
Phe Asn Gln Tyr Lys Thr Glu Ala Ala Ser Arg Tyr Asn Leu Thr Ile
                405                 410                 415

Ser Asp Val Ser Val Ser Asp Val Pro Phe Pro Phe Ser Ala Gln Ser
            420                 425                 430

Gly Ala Gly Val Trp Trp Thr Ser Asp Trp Gly Val Leu Thr Asn Leu
            435                 440                 445

Gly Ile Leu Leu Leu Leu Ser Ile Ala Val Leu Ile Ala Leu Ser Cys
        450                 455                 460

Ile Cys Arg Arg Lys Asn Tyr Gly Gln Leu Asp Ile Phe Pro Ala Arg
465                 470                 475                 480

Asp Thr Tyr His Pro Met Ser Glu Tyr Pro Thr Tyr His Thr His Gly
                485                 490                 495

Arg Tyr Val Pro Pro Ser Ser Thr Asp Arg Ser Pro Tyr Glu Lys Val
            500                 505                 510

Ser Ala Gly Asn Gly Gly Ser Ser Leu Ser Tyr Thr Asn Pro Ala Val
            515                 520                 525

Ala Ala Thr Ser Ala Asn Leu
        530                 535

<210> SEQ ID NO 31
<211> LENGTH: 29
<212> TYPE: DNA
<213> ORGANISM: Homo sapiens

<400> SEQUENCE: 31
tatgaatgta gaagcaggag attccagag                                       29

<210> SEQ ID NO 32
<211> LENGTH: 29
<212> TYPE: PRT
<213> ORGANISM: Homo sapiens

<400> SEQUENCE: 32

Thr Gly Gly Thr Ala Cys Thr Gly Gly Ala Ala Thr Thr Ala Cys Ala
1               5                   10                  15

Ala Cys Thr Ala Thr Thr Ala Thr Cys Cys Thr Cys Cys
            20                  25

<210> SEQ ID NO 33
<211> LENGTH: 29
<212> TYPE: PRT
<213> ORGANISM: Homo sapiens

<400> SEQUENCE: 33

Cys Cys Ala Ala Ala Gly Ala Ala Gly Gly Cys Ala Gly Ala Gly Ala
1               5                   10                  15

Thr Cys Ala Ala Cys Thr Ala Thr Ala Cys Thr Gly Gly
            20                  25

<210> SEQ ID NO 34
<211> LENGTH: 29
<212> TYPE: DNA
<213> ORGANISM: Homo sapiens

<400> SEQUENCE: 34
acacatagtt cctccattga agacttagc                                       29

<210> SEQ ID NO 35
```

```
<211> LENGTH: 29
<212> TYPE: DNA
<213> ORGANISM: Homo sapiens

<400> SEQUENCE: 35
taggattggt catggaaata gaatgcacc                                    29

<210> SEQ ID NO 36
<211> LENGTH: 29
<212> TYPE: DNA
<213> ORGANISM: Homo sapiens

<400> SEQUENCE: 36
aaggagactt ggaccaaaca ctgtgacaa                                    29

<210> SEQ ID NO 37
<211> LENGTH: 29
<212> TYPE: DNA
<213> ORGANISM: Homo sapiens

<400> SEQUENCE: 37
gcagtttgcc tgaaatatgc tggagtatt                                    29

<210> SEQ ID NO 38
<211> LENGTH: 29
<212> TYPE: DNA
<213> ORGANISM: Homo sapiens

<400> SEQUENCE: 38
cttacctcca aatggttctg acaatgact                                    29
```